(12) United States Patent
Shohat et al.

(10) Patent No.: US 7,776,551 B2
(45) Date of Patent: Aug. 17, 2010

(54) METHODS AND KITS FOR DIAGNOSING AND TREATING MENTAL RETARDATION

(75) Inventors: Mordechai Shohat, Petach-Tikva (IL); Lina Basel, Petach-Tikva (IL)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 121 days.

(21) Appl. No.: 11/484,719

(22) Filed: Jul. 12, 2006

(65) Prior Publication Data

US 2007/0015194 A1 Jan. 18, 2007

Related U.S. Application Data

(60) Provisional application No. 60/698,039, filed on Jul. 12, 2005.

(51) Int. Cl.
*G01N 33/53* (2006.01)
*C07H 21/04* (2006.01)
*C07H 21/02* (2006.01)
*C12Q 1/68* (2006.01)

(52) U.S. Cl. .............................. 435/7.1; 536/23.1; 435/6

(58) Field of Classification Search ....................... None
See application file for complete search history.

(56) References Cited

U.S. PATENT DOCUMENTS

2003/0125289 A1 * 7/2003 Gelb et al. ..................... 514/44
2006/0134663 A1 * 6/2006 Harkin et al. .................. 435/6

OTHER PUBLICATIONS

Basel-Vanagaite et al. Jour Med Genet 43: 203-210, 2006.*
Rogaeva et al. JBC 282: 20897-20905, 2007.*
Toniolo, Am J Med Genet 97: 221-227, 2000.*
Ropers and Hamel, Nature Rev Genet, 6: 46-57, 2005.*
Kilts. Biol Psychiatry 50: 845-855, 2001.*
Einat, J Psycopharmacol 20: 714-722, 2006.*
Mazza et al. Schizo Res 47: 299-308, 2001.*
Ou et al. "Freud-1: A Neuronal Calcium-Regulated Repressor of the 5-HT1A Receptor Gene", The Journal of Neuroscience, 23(19):7415-7425, 2003.
Meirleir et al. "Bilateral Striatal Necrosis With a Novel Point Mutation in the Mitochondrial ATPase 6 Gene", Pediatric Neurology, 13(3):242-246, 1995.
Molinari et al. "Truncating Neurotrypsin Mutation in Autosomal Recessive Nonsyndromic Mental Retardation", Science, 298:1779-1781, 2002.
Cronshaw et al. "The Nuclear Pore Complex Protein ALADIN is Mislocalized in Triple A Syndrome", PNAS, 100(10):5823-5827, 2003.
Thyagarajan et al. "A Novel Mitochondrial A TPase 6 Point Mutation in Familial Bilateral Striatal Necrosis", Ann Neurol, 38:468-472, 1995.
Finlay et al. "A Complex of Nuclear Pore Proteins Required for Pore Function", The Journal of Cell Biology, 114(1):169-183, 1991.
Higgins et al. "Mutation in A Novel ATP-Dependent Lon Protease Gene in A Kindred With Mild Mental Retardation", Neurology, 63:1927-1931, 2004.
Straussberg et al. "Familial Infantile Bilateral Striatal Necrosis: Clinical Features and Response to Biotin Treatment", Neurology, 59:983-989, 2002.
Vanagaite et al. "Infantile Bilateral Striatal Necrosis Maps to Chromosome 19q", Neurology, 62:87-90, 2004.
Matsuda et al. "Large-Scale Identification and Characterization of Human Genes That Activate NF-kB and MAPK Signaling Pathways", Oncogene, 22:3307-3318, 2003.
Hetzer et al. "Pushing the Envelope: Structure, Function, and Dynamics of the Nuclear Periphery", Annu. Rev. Cell Dev. Biol, 21:347-80, 2005.
Vanagaite et al. "Mapping of a New Locus for Autosomal Recessive Non-Syndromic Mental Retardation in the Chromosomal Region 19p13.12-p13.2: Further Genetic Heterogeneity", J. Med. Genet., 40:729-732, 2003.
Pelet et al. "Mutant WD-Repeat Protein in Triple-A Syndrome", Nature Genetics, 26:332-335, 2000.

* cited by examiner

*Primary Examiner*—Jeffrey Stucker
*Assistant Examiner*—Aditi Dutt

(57) ABSTRACT

The present invention provides methods, kits, isolated nucleic acid sequences, antibodies and addressable oligonucleotides microarrays which can be for analyzing sequence alterations and detecting the expression level of CC2D1A or nup62 in cells of an individual and thus diagnose nonsyndromic mental retardation (NSMR) and/or infantile bilateral striatal necrosis (IBSN) in the individual. In addition, the present invention provides methods and pharmaceutical compositions which can be used to treat pathologies associated with mental retardation such as NSMR or IBS.

5 Claims, 27 Drawing Sheets

(9 of 27 Drawing Sheet(s) Filed in Color)

Fig. 1c

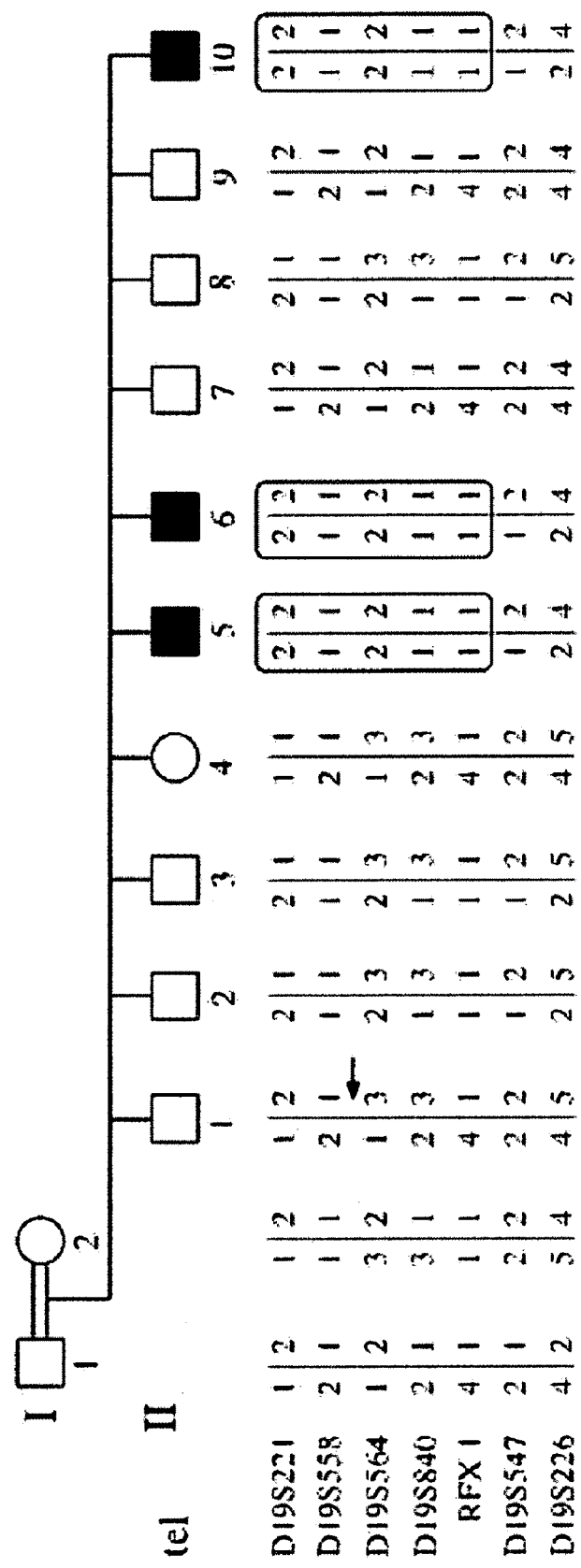

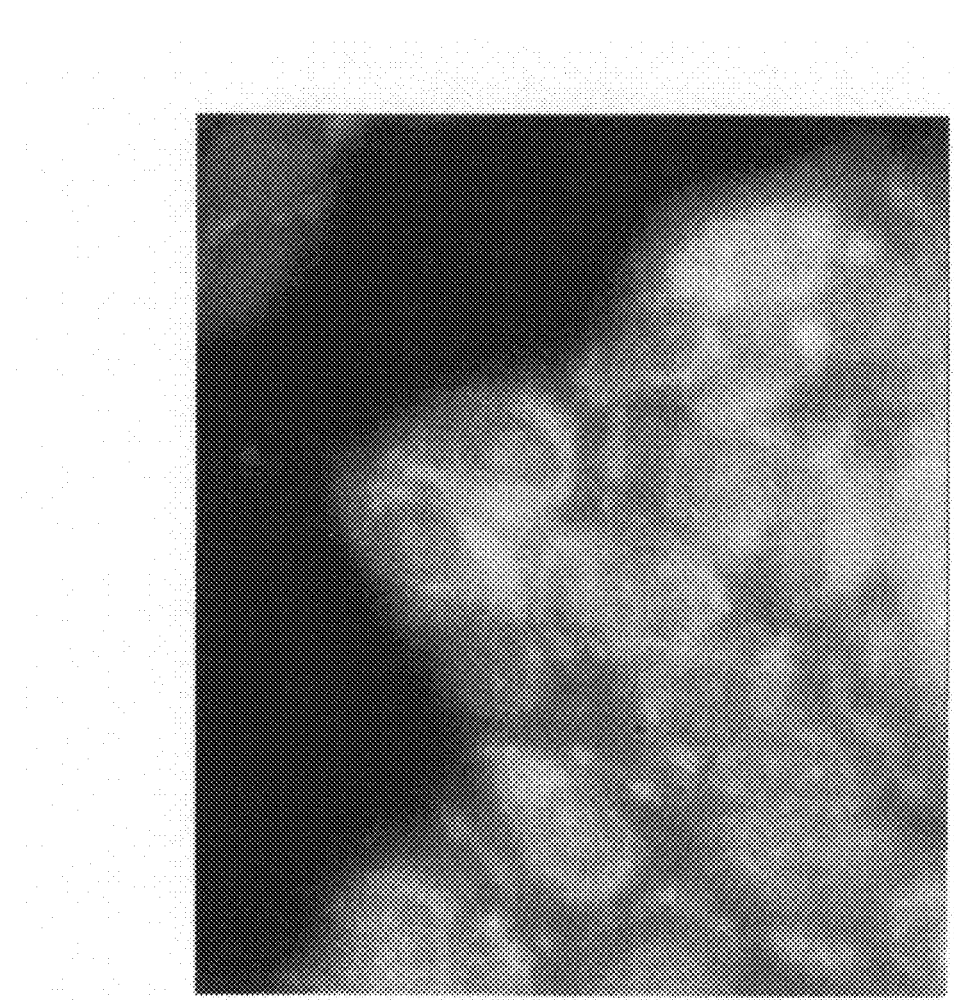
Fig. 7
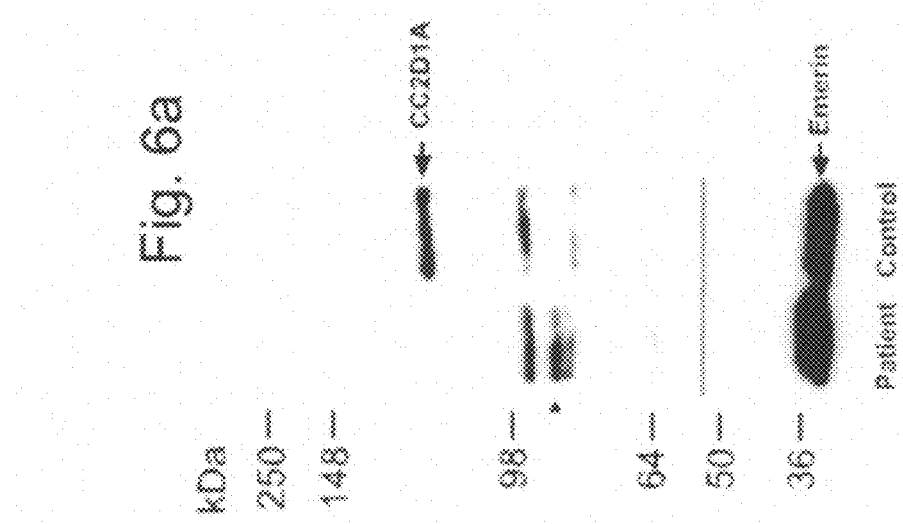
Fig. 6a
Fig. 6b

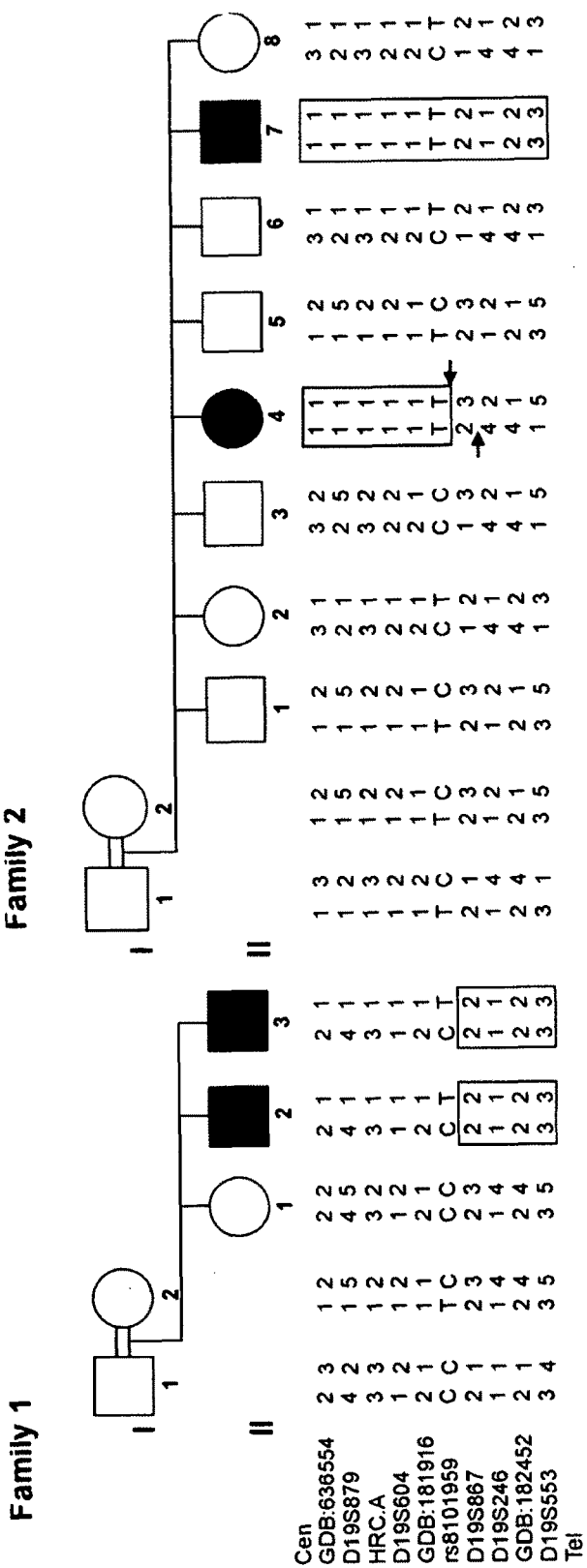

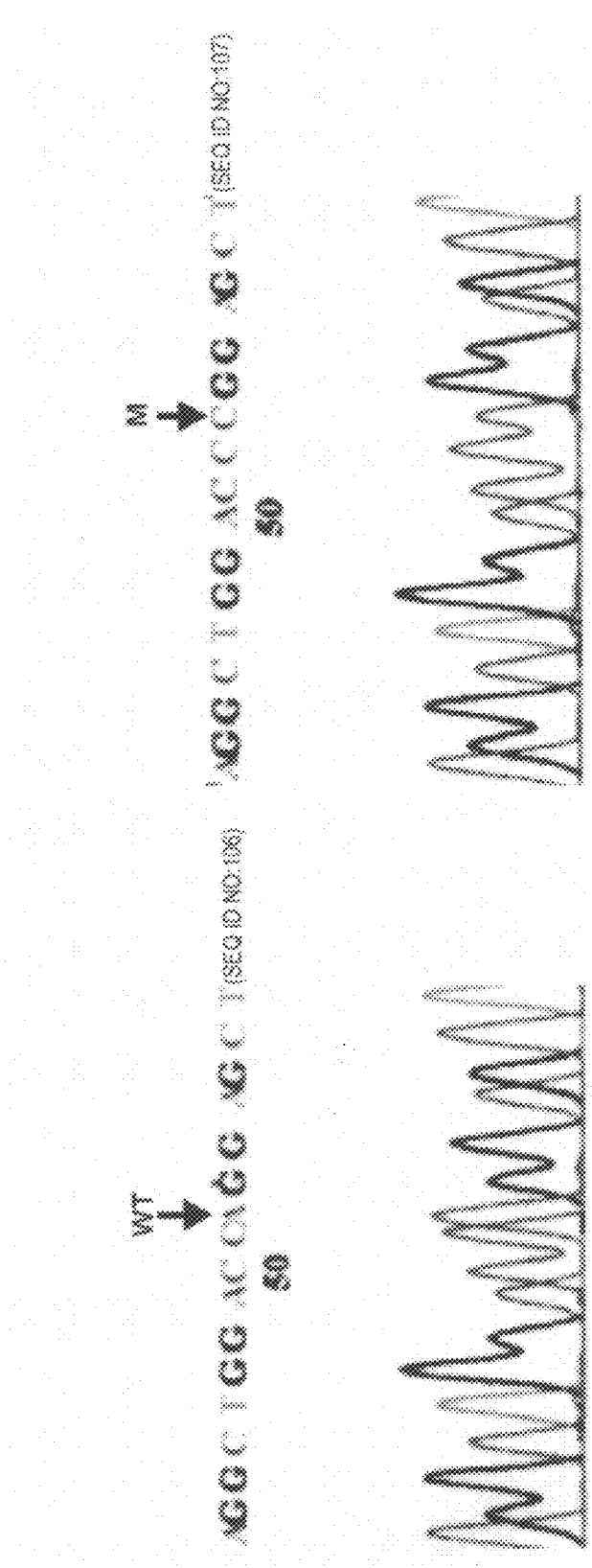

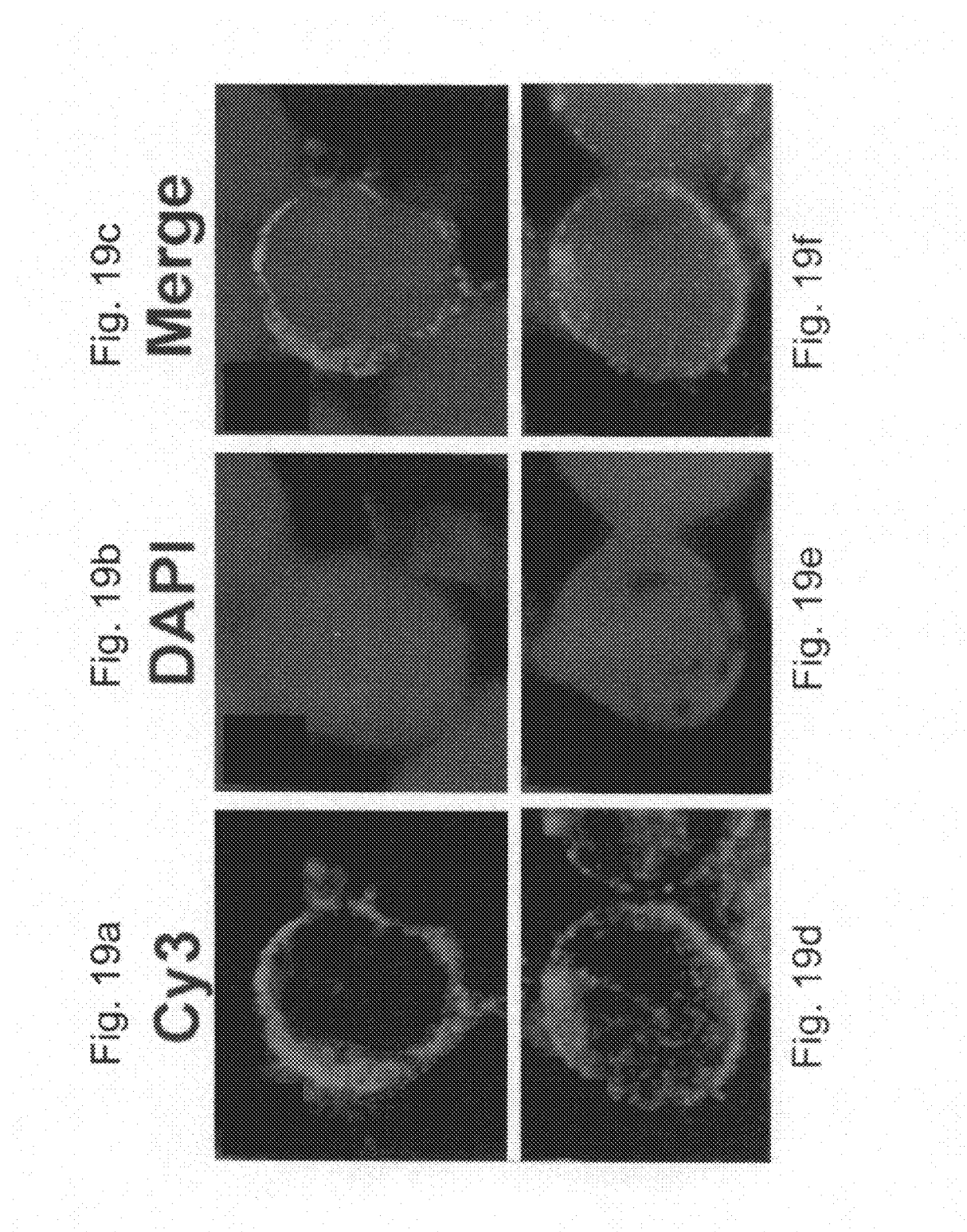

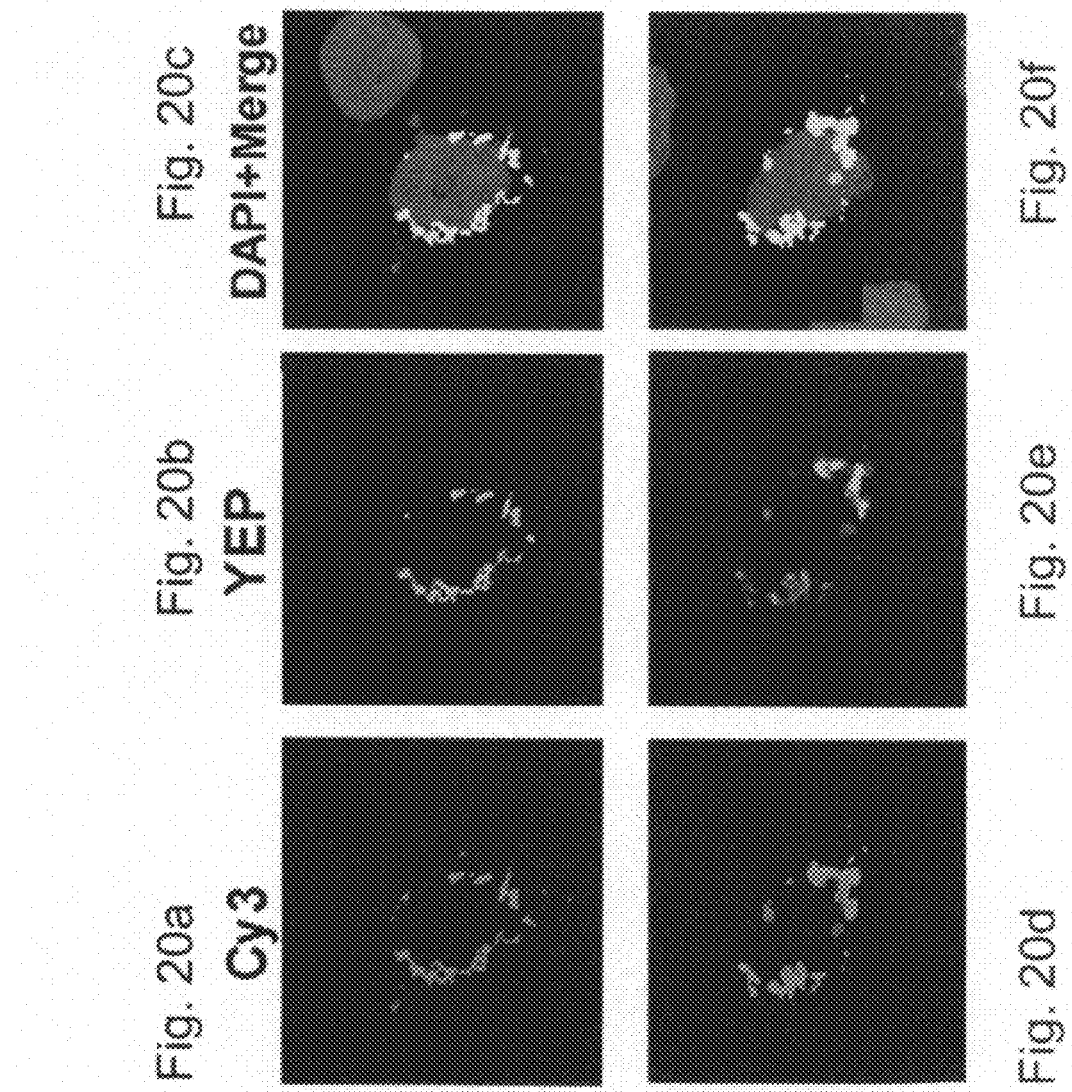

SEQUENCE LISTING

<160> NUMBER OF SEQ ID NOS: 110

<210> SEQ ID NO 1
<211> LENGTH: 3599
<212> TYPE: DNA
<213> ORGANISM: Homo sapiens

<400> SEQUENCE: 1

```
gcgctccggt gcggcggcgc ccgaggcccg aggcggaagt gggacggcca agcagggaag    60
cgagggctcg ggatcgacgg ccgcggggcg ccgacgagga gtgcaggact caggaagggc   120
gagtgcgcgg cgacagagcc cggggaagga ggcagggcaa ggccgggctt gggggcaggt   180
ggtccgggca tccagccttg aagatgcaca agaggaaagg accccgggga cccccgggca   240
gaggcgccgc ggccgcccgc cagctgggcc tgctggttga cctctcccca gatggcctga   300
tgatccctga ggacggggct aacgatgaag aactggaggc tgagttcttg gctttggtcg   360
ggggccagcc cccagccctg agaagctca aaggcaaagg tcccttgccg atggaggcca   420
ttgagaagat ggccagcctg tgcatggaga cccggatga ggatgaggag gagggacgg    480
atgaggacga cttggaggct gatgatgacc tgctggcgga gctaaatgag gtccttggag   540
aggagcagaa ggcttcagag accccacctc ctgtggccca ccgaagcct gaggcccctc    600
atccggggct ggagaccacc ttgcaggaga ggctggcgct ctatcagaca gcaattgaaa   660
gcgccagaca agctggagac agcgccaaga tgcggcgcta cgatcggggg cttaaaacac   720
tggaaaacct gctcgcctcc atccgtaagg gcaatgccat tgacgaagcg gacatcccgc   780
cgccagtggc cataggaaaa ggccgggcgt ccacgcctac ctacagccct gcacccaccc   840
agccggcccc tagaatcgcg tcagccccag agcccagggt caccctggag ggaccttctg   900
ccaccgcccc agcctcatct ccaggcttgg ctaagcccca gatgcccca ggtcctgca    960
gccctggccc tctggcccag ttgcagagcc gccagcgcga ctacaagctg gctgccctcc  1020
acgccaagca gcaggagat accactgctg ccgctagaca cttccgcgtg ctaagagct   1080
ttgatgctgt cttggaggcc ctgagccggg gtgagcccgt ggacctctcc tgcctgcccc  1140
ctccacccga ccagctgccc ccagacccac cgtcaccacc gtcgcagcct ccgacccccg  1200
ctacggcgcc ctccacaaca gaggtgcccc caccccgag gaccctgctg gaggcgctgg  1260
agcagcggat ggagcggtac caggtggccg cagcccaggc caagagcaag ggggaccagc  1320
ggaaagctcg aatgcacgag cgcatcgtca agcaatacca gatgccatc cgagcccaca    1380
aggctggccg agccgtggat gtcgctgaat tgcccgtgcc cccaggcttc ccccaatcc    1440
agggcctgga ggcaccaag cccacccagc agagtctggt gggtgtcctg gagactgcca  1500
tgaagctggc caaccaggat gaaggcccag aggatgaaga ggatgaggtg cctaagaagc  1560
agaacagccc tgtggccccc acagcccagc ccaaagcccc accctcaaga actcccagt   1620
cgggatcagc cccaacagcc aaagcgcccc ccaaagccac atccaccaga gcccagcagc  1680
agctggcctt cctagagggc cgcaagaagc agctcctgca ggccgcactg cgagccaagc  1740
agaaaaacga cgtggagggt gccaagatgc acctgcgcca agccaaggga ctggagccta  1800
tgctggaggc ctcgcgcaat gggctgcctg tggacatcac caaggtgcgc ctgccctg    1860
tcaacaagga cgactttgcc ctggtccagc ggcctggccc gggtctgtct caggaggccg  1920
cccggcgcta tggtgaactc accaagctca tacggcagca gcacgagatg tgcctgaacc  1980
actcaaacca attcacccag ctgggcaaca tcactgaaac caccaagttt gaaaagttgg  2040
```

-continued

```
cggaggactg taagcggagc atggacattc tgaagcaagc cttcgtccgg ggtctcccca    2100
cgcccaccgc ccgctttgag caaaggacct tcagcgtcat caagatcttc cctgacctca    2160
gcagcaacga catgctcctc ttcatcgtga agggcatcaa cttgcccaca cccccaggac    2220
tgtcccctgg cgatctggat gtctttgttc ggtttgactt ccccctatccc aacgtggaag   2280 aagctcagaa agacaagacc agtgtgatca agaacacaga ctcccctgag ttcaaggagc    2340
agttcaaact ctgcatcaac cgcagccacc gtggcttccg aagggccatc cagaccaagg    2400
gcatcaagtt cgaagtggtt cacaaggggg ggctgttcaa gactgaccgg gtgctgggga    2460
cagcccagct gaagctggat gcactggaga tagcatgtga ggtccgggag atccttgagg    2520
tcctggatgg tcgccggccc acagggggc gactggaggt aatggtccgg attcgggagc     2580
cactgacagc ccagcagttg gagacgacga cagagaggtg gctggtcatt gaccctgtgc    2640
cggcagctgt gcccacacag gttgctgggc caaagggaa ggcccctcct gtgcctgccc     2700
ctgcaaggga gtcagggaac agatcagccc ggcccctgca tagcctcagt gtgctggcgt    2760
ttgaccaaga gcgtctggag cggaagatcc tggccctcag gcaggcgcgg cggccggtgc    2820
ccccagaagt ggcccagcag taccaggaca tcatgcaacg cagccagtgg cagagggcac    2880
agctggagca gggggtgtg ggcatccgac gggaatacgc agcccagctg gagcggcagc     2940
tgcagttcta cacggaggct gcccggcgcc tgggcaacga tggcagcagg gatgctgcaa    3000
aggaggcgct ctataggcgg aatctggtag agagtgagct gcagcggctc cgcaggtgag    3060
gagcccatgg ggcgggcagc ccccagaaag cgggcagcag gccccgatac cgggaagagc    3120
cgacacagcc acgaaccaga caagcagaca atcagcggac aatcggttct ggactcaccc    3180
ctcatccggg cccccagccc cgccagagcc tccgtggctg cgggtgttgg gaaccatgcc    3240
tgccagccag tatgtgcccc tcacccaggc ctggctgggc cctggagagt cctgtttgca    3300
cagcccaggg gtgtccggcc tctggcccgc cccggagcag ggagggtggc tggggccaag    3360
ccccgagggc ccctgcaagc actttacttc ctgttcctcc ccagccttaa ccccaaagcc    3420
ctcctgcacc ccaaagaagc cactgaggct ggccgagcca cactgtctcc caggggcgt    3480 cgacctggcc cagctgggtc cccagggcca gcacatggaa taaaatagcc agggccacac    3540 tcaaaaaaa aaaaaaaaa aaaaaaaaa aaaaaaaaa aaaaaaaaa aaaaaaaa          3599
```

<210> SEQ ID NO 2
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 2

```
gtggatgtcg ctgaattgc                                                 19
```

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 3

```
tacagtcctc cgccaacttt                                                20
```

<210> SEQ ID NO 4

```
<211> LENGTH: 951
<212> TYPE: PRT
<213> ORGANISM: Homo sapiens

<400> SEQUENCE: 4
```

| | | | | | | | | | | | | | | |
|---|---|---|---|---|---|---|---|---|---|---|---|---|---|---|
|Met|His|Lys|Arg|Lys|Gly|Pro|Gly|Pro|Gly|Arg|Gly|Ala|Ala|
|1| | | |5| | | |10| | | |15| |
|Ala|Ala|Arg|Gln|Leu|Gly|Leu|Leu|Val|Asp|Leu|Ser|Pro|Asp|Gly|Leu|
| | |20| | | |25| | | |30| | | | |
|Met|Ile|Pro|Glu|Asp|Gly|Ala|Asn|Asp|Glu|Glu|Leu|Glu|Ala|Glu|Phe|
| | | |35| | | |40| | | |45| | | |
|Leu|Ala|Leu|Val|Gly|Gly|Gln|Pro|Pro|Ala|Leu|Glu|Lys|Leu|Lys|Gly|
| |50| | | | |55| | | |60| | | | |
|Lys|Gly|Pro|Leu|Pro|Met|Glu|Ala|Ile|Glu|Lys|Met|Ala|Ser|Leu|Cys|
|65| | | | |70| | | |75| | | | |80|
|Met|Arg|Asp|Pro|Asp|Glu|Asp|Glu|Glu|Gly|Thr|Asp|Glu|Asp|Asp|
| | | | |85| | | |90| | | |95| |
|Leu|Glu|Ala|Asp|Asp|Asp|Leu|Leu|Ala|Glu|Leu|Asn|Glu|Val|Leu|Gly|
| | | |100| | | |105| | | |110| | | |
|Glu|Glu|Gln|Lys|Ala|Ser|Glu|Thr|Pro|Pro|Val|Ala|Gln|Pro|Lys|
| | | |115| | | |120| | | |125| | | |
|Pro|Glu|Ala|Pro|His|Pro|Gly|Leu|Glu|Thr|Thr|Leu|Gln|Glu|Arg|Leu|
| |130| | | | |135| | | |140| | | | |
|Ala|Leu|Tyr|Gln|Thr|Ala|Ile|Glu|Ser|Ala|Arg|Gln|Ala|Gly|Asp|Ser|
|145| | | | |150| | | |155| | | | |160|
|Ala|Lys|Met|Arg|Arg|Tyr|Asp|Arg|Gly|Leu|Lys|Thr|Leu|Glu|Asn|Leu|
| | | |165| | | |170| | | |175| | | |
|Leu|Ala|Ser|Ile|Arg|Lys|Gly|Asn|Ala|Ile|Asp|Glu|Ala|Asp|Ile|Pro|
| | |180| | | |185| | | |190| | | | |
|Pro|Pro|Val|Ala|Ile|Gly|Lys|Gly|Pro|Ala|Ser|Thr|Pro|Thr|Tyr|Ser|
| | |195| | | |200| | | |205| | | | |
|Pro|Ala|Pro|Thr|Gln|Pro|Ala|Pro|Arg|Ile|Ala|Ser|Ala|Pro|Glu|Pro|
| |210| | | | |215| | | |220| | | | |
|Arg|Val|Thr|Leu|Glu|Gly|Pro|Ser|Ala|Thr|Ala|Pro|Ala|Ser|Ser|Pro|
|225| | | | |230| | | |235| | | | |240|
|Gly|Leu|Ala|Lys|Pro|Gln|Met|Pro|Pro|Gly|Pro|Cys|Ser|Pro|Gly|Pro|
| | | |245| | | |250| | | |255| | | |
|Leu|Ala|Gln|Leu|Gln|Ser|Arg|Gln|Arg|Asp|Tyr|Lys|Leu|Ala|Ala|Leu|
| | |260| | | |265| | | |270| | | | |
|His|Ala|Lys|Gln|Gln|Gly|Asp|Thr|Thr|Ala|Ala|Ala|Arg|His|Phe|Arg|
| |275| | | | |280| | | |285| | | | |
|Val|Ala|Lys|Ser|Phe|Asp|Ala|Val|Leu|Glu|Ala|Leu|Ser|Arg|Gly|Glu|
| |290| | | | |295| | | |300| | | | |
|Pro|Val|Asp|Leu|Ser|Cys|Leu|Pro|Pro|Pro|Asp|Gln|Leu|Pro|Pro|
|305| | | | |310| | | |315| | | | |320|
|Asp|Pro|Pro|Ser|Pro|Pro|Ser|Gln|Pro|Pro|Thr|Pro|Ala|Thr|Ala|Pro|
| | | |325| | | |330| | | |335| | | |
|Ser|Thr|Thr|Glu|Val|Pro|Pro|Pro|Arg|Thr|Leu|Leu|Glu|Ala|Leu|
| | | |340| | | |345| | | |350| | | |
|Glu|Gln|Arg|Met|Glu|Arg|Tyr|Gln|Val|Ala|Ala|Gln|Ala|Lys|Ser|
| | |355| | | |360| | | |365| | | | |
|Lys|Gly|Asp|Gln|Arg|Lys|Ala|Arg|Met|His|Glu|Arg|Ile|Val|Lys|Gln|
| |370| | | | |375| | | |380| | | | |
|Tyr|Gln|Asp|Ala|Ile|Arg|Ala|His|Lys|Ala|Gly|Arg|Ala|Val|Asp|Val|

-continued

```
            385                 390                 395                 400
        Ala Glu Leu Pro Val Pro Pro Gly Phe Pro Pro Ile Gln Gly Leu Glu
                        405                 410                 415

Ala Thr Lys Pro Thr Gln Gln Ser Leu Val Gly Val Leu Glu Thr Ala
                        420                 425                 430

Met Lys Leu Ala Asn Gln Asp Glu Gly Pro Glu Asp Glu Glu Asp Glu
                        435                 440                 445

Val Pro Lys Lys Gln Asn Ser Pro Val Ala Pro Thr Ala Gln Pro Lys
                450                 455                 460

Ala Pro Pro Ser Arg Thr Pro Gln Ser Gly Ser Ala Pro Thr Ala Lys
        465                 470                 475                 480

Ala Pro Pro Lys Ala Thr Ser Thr Arg Ala Gln Gln Gln Leu Ala Phe
                        485                 490                 495

Leu Glu Gly Arg Lys Lys Gln Leu Leu Gln Ala Ala Leu Arg Ala Lys
                        500                 505                 510

Gln Lys Asn Asp Val Glu Gly Ala Lys Met His Leu Arg Gln Ala Lys
                        515                 520                 525

Gly Leu Glu Pro Met Leu Glu Ala Ser Arg Asn Gly Leu Pro Val Asp
                        530                 535                 540

Ile Thr Lys Val Pro Pro Ala Pro Val Asn Lys Asp Asp Phe Ala Leu
        545                 550                 555                 560

Val Gln Arg Pro Gly Pro Gly Leu Ser Gln Glu Ala Ala Arg Arg Tyr
                        565                 570                 575

Gly Glu Leu Thr Lys Leu Ile Arg Gln Gln His Glu Met Cys Leu Asn
                        580                 585                 590

His Ser Asn Gln Phe Thr Gln Leu Gly Asn Ile Thr Glu Thr Thr Lys
                        595                 600                 605

Phe Glu Lys Leu Ala Glu Asp Cys Lys Arg Ser Met Asp Ile Leu Lys
                        610                 615                 620

Gln Ala Phe Val Arg Gly Leu Pro Thr Pro Thr Ala Arg Phe Glu Gln
        625                 630                 635                 640

Arg Thr Phe Ser Val Ile Lys Ile Phe Pro Asp Leu Ser Ser Asn Asp
                        645                 650                 655

Met Leu Leu Phe Ile Val Lys Gly Ile Asn Leu Pro Thr Pro Pro Gly
                        660                 665                 670

Leu Ser Pro Gly Asp Leu Asp Val Phe Val Arg Phe Asp Phe Pro Tyr
                        675                 680                 685

Pro Asn Val Glu Glu Ala Gln Lys Asp Lys Thr Ser Val Ile Lys Asn
                        690                 695                 700

Thr Asp Ser Pro Glu Phe Lys Glu Gln Phe Lys Leu Cys Ile Asn Arg
        705                 710                 715                 720

Ser His Arg Gly Phe Arg Arg Ala Ile Gln Thr Lys Gly Ile Lys Phe
                        725                 730                 735

Glu Val Val His Lys Gly Gly Leu Phe Lys Thr Asp Arg Val Leu Gly
                        740                 745                 750

Thr Ala Gln Leu Lys Leu Asp Ala Leu Glu Ile Ala Cys Glu Val Arg
                        755                 760                 765

Glu Ile Leu Glu Val Leu Asp Gly Arg Arg Pro Thr Gly Gly Arg Leu
                        770                 775                 780

Glu Val Met Val Arg Ile Arg Glu Pro Leu Thr Ala Gln Gln Leu Glu
        785                 790                 795                 800

Thr Thr Thr Glu Arg Trp Leu Val Ile Asp Pro Val Pro Ala Ala Val
                        805                 810                 815
```

```
Pro Thr Gln Val Ala Gly Pro Lys Gly Lys Ala Pro Val Pro Ala
            820                 825                 830

Pro Ala Arg Glu Ser Gly Asn Arg Ser Ala Arg Pro Leu His Ser Leu
            835                 840                 845

Ser Val Leu Ala Phe Asp Gln Glu Arg Leu Glu Arg Lys Ile Leu Ala
            850                 855                 860

Leu Arg Gln Ala Arg Arg Pro Val Pro Pro Glu Val Ala Gln Gln Tyr
865                 870                 875                 880

Gln Asp Ile Met Gln Arg Ser Gln Trp Gln Arg Ala Gln Leu Glu Gln
                    885                 890                 895

Gly Gly Val Gly Ile Arg Arg Glu Tyr Ala Ala Gln Leu Glu Arg Gln
            900                 905                 910

Leu Gln Phe Tyr Thr Glu Ala Ala Arg Arg Leu Gly Asn Asp Gly Ser
            915                 920                 925

Arg Asp Ala Ala Lys Glu Ala Leu Tyr Arg Arg Asn Leu Val Glu Ser
930                 935                 940

Glu Leu Gln Arg Leu Arg Arg
945                 950

<210> SEQ ID NO 5
<211> LENGTH: 437
<212> TYPE: PRT
<213> ORGANISM: Homo sapiens
<220> FEATURE:
<221> NAME/KEY: misc_feature
<223> OTHER INFORMATION: Mutant CC2D1A with deleted amino acids 408 to
      547

<400> SEQUENCE: 5

Met His Lys Arg Lys Gly Pro Pro Gly Pro Gly Arg Gly Ala Ala
1               5                   10                  15

Ala Ala Arg Gln Leu Gly Leu Leu Val Asp Leu Ser Pro Asp Gly Leu
            20                  25                  30

Met Ile Pro Glu Asp Gly Ala Asn Asp Glu Glu Leu Glu Ala Glu Phe
            35                  40                  45

Leu Ala Leu Val Gly Gly Gln Pro Ala Leu Glu Lys Leu Lys Gly
    50                  55                  60

Lys Gly Pro Leu Pro Met Glu Ala Ile Glu Lys Met Ala Ser Leu Cys
65                  70                  75                  80

Met Arg Asp Pro Asp Glu Asp Glu Glu Gly Thr Asp Glu Asp
                85                  90                  95

Leu Glu Ala Asp Asp Asp Leu Leu Ala Glu Leu Asn Glu Val Leu Gly
            100                 105                 110

Glu Glu Gln Lys Ala Ser Glu Thr Pro Pro Val Ala Gln Pro Lys
        115                 120                 125

Pro Glu Ala Pro His Pro Gly Leu Glu Thr Thr Leu Gln Glu Arg Leu
            130                 135                 140

Ala Leu Tyr Gln Thr Ala Ile Glu Ser Ala Arg Gln Ala Gly Asp Ser
145                 150                 155                 160

Ala Lys Met Arg Arg Tyr Asp Arg Gly Leu Lys Thr Leu Glu Asn Leu
                165                 170                 175

Leu Ala Ser Ile Arg Lys Gly Asn Ala Ile Asp Glu Ala Asp Ile Pro
            180                 185                 190

Pro Pro Val Ala Ile Gly Lys Gly Pro Ala Ser Thr Pro Thr Tyr Ser
            195                 200                 205
```

-continued

```
Pro Ala Pro Thr Gln Pro Ala Pro Arg Ile Ala Ser Ala Pro Glu Pro
    210                 215                 220
Arg Val Thr Leu Glu Gly Pro Ser Ala Thr Ala Pro Ala Ser Ser Pro
225                 230                 235                 240
Gly Leu Ala Lys Pro Gln Met Pro Pro Gly Pro Cys Ser Pro Gly Pro
                245                 250                 255
Leu Ala Gln Leu Gln Ser Arg Gln Arg Asp Tyr Lys Leu Ala Ala Leu
            260                 265                 270
His Ala Lys Gln Gln Gly Asp Thr Thr Ala Ala Arg His Phe Arg
        275                 280                 285
Val Ala Lys Ser Phe Asp Ala Val Leu Glu Ala Leu Ser Arg Gly Glu
    290                 295                 300
Pro Val Asp Leu Ser Cys Leu Pro Pro Pro Asp Gln Leu Pro Pro
305                 310                 315                 320
Asp Pro Pro Ser Pro Pro Ser Gln Pro Pro Thr Pro Ala Thr Ala Pro
                325                 330                 335
Ser Thr Thr Glu Val Pro Pro Pro Arg Thr Leu Leu Glu Ala Leu
            340                 345                 350
Glu Gln Arg Met Glu Arg Tyr Gln Val Ala Ala Ala Gln Ala Lys Ser
        355                 360                 365
Lys Gly Asp Gln Arg Lys Ala Arg Met His Glu Arg Ile Val Lys Gln
    370                 375                 380
Tyr Gln Asp Ala Ile Arg Ala His Lys Ala Gly Arg Ala Val Asp Val
385                 390                 395                 400
Ala Glu Leu Pro Val Pro Gly Ala Ala Cys Pro Cys Gln Gln Gly
                405                 410                 415
Arg Leu Cys Pro Gly Pro Ala Ala Trp Pro Gly Ser Val Ser Gly Gly
            420                 425                 430
Arg Pro Ala Leu Trp
        435
```

<210> SEQ ID NO 6
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 6
gtggatgtcg ctgaattgc                                            19

<210> SEQ ID NO 7
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 7
caagcgatcc tcccatctt                                            19

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 8

```
tacagtcctc cgccaacttt                                                    20

<210> SEQ ID NO 9
<211> LENGTH: 469
<212> TYPE: DNA
<213> ORGANISM: Artificial sequence
<220> FEATURE:
<223> OTHER INFORMATION: In situ hybridization probe

<400> SEQUENCE: 9
tagagaaact gaaaggccaa ggtcccctgc caatggaagc cattgagaag atggcccggc        60
tctgcatgag agacctggat gaggacgagg aggggacaga cgaggatgat gtggaggctg       120
atgaggacct gctggcagag ctaaatgagg tccttggaga agaacagaag gctgtggagc       180
ccctgatgcc tgtggcccag ccgaagcctt caggccccaa tccaggagta gaggccacgc       240
tgcaggagag gctaaccctc taccagtctg cactggagag tgccaggcaa gctggggaca       300
gtgccaagat gcgacgctat gaccgggggc tcaagacgct ggaaaacctg ctggtctctg       360
caaagaaggg caacatcatc aatgaagcag acattccacc acctgtggca tcggggaagg       420
gagcagcagc tgggcacagc cacacccaag ctacttccca gttggcttc                   469

<210> SEQ ID NO 10
<211> LENGTH: 369
<212> TYPE: DNA
<213> ORGANISM: Artificial sequence
<220> FEATURE:
<223> OTHER INFORMATION: In situ hybridization probe

<400> SEQUENCE: 10
cggaacctgg tggagagcga gctgcagcga ctccgcaggt gaggcccatc ctggactaca        60
ggccccacag cccgatgcta ggcagagctc agggccacc gaacagacaa gcagacaatc       120
agcggacagt tggttctgga ctcgcccgt ccaggccctc ggcccagggg catcgggac         180 agcacagtca ccccagcctg gctggttggg ccttggagag tcctgtttgc acatccagga       240
gcatctggag caaggagggt agctgggatg tgaacccaga gggccctgca agcactttac       300
ttcctgcccc tcccattgtg aacccccacag ccctctccaa agatacctct gaggctgtcc      360
agctcagct                                                              369

<210> SEQ ID NO 11
<211> LENGTH: 3154
<212> TYPE: DNA
<213> ORGANISM: Mus musculus

<400> SEQUENCE: 11
gaattcctgg ctttggtggg gggtcagccc caggccctag agaaactgaa aggccaaggt        60
cccctgccaa tggaagccat tgagaagatg gcccggctct gcatgagaga cctggatgag       120
gacgaggagg ggacagacga ggatgatgtg gaggctgatg aggacctgct ggcagagcta       180
aatgaggtcc ttggagaaga acagaaggct gtggagcccc tgatgcctgt ggcccagccg       240
aagccttcag gccccaatcc aggagtagag gccacgctgc aggagaggct aaccctctac       300
cagtctgcac tggagagtgc caggcaagct ggggacagtg ccaagatgcg acgctatgac       360
cgggggctca agacgctgga aaacctgctg gtctctgcaa agaagggcaa catcatcaat       420
gaagcagaca ttccaccacc tgtggcatcg gggaagggag cagcagctgg gcacagccac       480
acccaagcta cttcccagtt ggcttctgta agcccgccag cccagagtc cagcggcacc         540 ttggaggccc catctaccac tacacccacc tctgctaagc cccagctacc cccagatccc       600
```

```
tgcagccccc tagcccggtt gcagagcctc cagcacgagt acaaactggc tgcccttcgt    660
gccaagcatc aggatgacac tgctacagcc accagacact tgagaatagc taagagcttt    720
gaccctgtct tggaggccct gagccgtggg gaactggtgg acctgtcccg cctgccccct    780
cccctgacc agctgtcccc agagccccc ttgccagctg cccaacctttt gacctctgcc     840
tcaacactca ccaggccaga ggttccccaa ccccgagga acctcctgga ggctctggaa    900
cagcgaatgg agcggtacca tgtggctgca gcccaggcca aggccaaggg tgaccagcgg    960
aaggcacgca tgcatgaacg aattgtcaag caataccaag acgccattcg tgcccacaag   1020
gcaggccgag ctgtggatgt ggcggagctg ccagtgcccc caggcttccc cccaatgcag   1080
ggtttggagt ctgcagagcc ctctcaacag agcctagtgg gtgtcctgga aactgccatg   1140
aggcttgcca accacgacga aggctcggat gacgaagagg aggagactcc taagaagcag   1200
aatacccctg ctgcctccac aacccagctg aagtcctcgc cctccaaagc acctccatca   1260
ggaccagccc cagccggcaa agctgccccc aagggcacat ccaacagagc ccagcagcag   1320
ctggccttcc tggagggccg taagaagcag ctcctgcagg ccgcgctgcg tgccaagcaa   1380
aagaacgacg tagaaggcgc caagatgcac ctgcgccagg ccaaagggct agagcccatg   1440
ctagaggcct ctcgcaatgg actgcctgtg acattgcca aggtgccacc tgctcctgtc    1500
aacaaggacg actttgtgct ggtgcagcgg cctggcccag gcttgtctca ggaagctgtg   1560
cgtcgctatg ggaacttac caagctcctg agacagcaac atgaaatgtg tctaaaccac    1620
tccacacagt tcacccacct gggcaacatt gctgaaacca ttaagttcga aagctggca    1680
gaagactgta gcggagcat ggacaccta aaacaagcct cgcccgcag tctgcccaca      1740
cccgcagccc gctttgagca gaggaccttc agtgtcatca aggtctttcc ggacttgagc   1800
aacagtgaca tgctcctgtt tatcgtgaag ggcatcaact tgcccacacc cacagggctg   1860
tcccccagtg acctggatgc cttttgtccgc tttgacttcc cttatcccaa tgtggaagaa  1920
gctcagaaag acaagaccag tgtgatcaaa aacacagact cccctgaatt taaggagcag   1980
ttcaaactct gcatcaaccg tggccaccgt ggcttccgaa gggccatcca aaccaagggc   2040
atcaagttcg aagtggtcca agggggggg ctgttcaaga cggacagggt gctaggtaca    2100
gcccagctga agctgggtac gttggaaaca gcttgtgaag tccacgagat cctggaggtt   2160
ttggatggac gccgacccac gggggggagg cttgaagtga tggttcgcat ccgggagcca   2220
ctgacagccc agcagttgga aactacaact gagaggtggc tggtcattga tcacatccca   2280
gcagctatgc ccactgtcac tgggcccaaa gcaaaggctc ctctcatacc ggcgtcttca   2340
agggaagcag gcaacagatc agcacggccc ctgcatagcc ttagcgtgtt ggcctttgac   2400
caagagcggc tagaaaggaa gatcctggcc ctgaggcagg cacgccggcc tgtgcctcca   2460
gaagtggccc agcagtacca ggacgtagta cagcgtagcc aatggcagag gcacagctg    2520
gagcagggg gtgctgccct ccgcagggag tatgcaagcc atctggagcg ccagctgcac   2580
ttctatacag aggctgcccg gcgcctgggc tacgatggaa gcaggaggc tgcaaaggag   2640
gcattgtatc ggcggaacct ggtggagagc gagctgcagc gactccgcag gtgaggccca   2700
tcctggacta caggccccac agcccgatgc taggcagagc tccagggcca ccgaacagac   2760
aagcagacaa tcagcggaca gttggttctg gactcgccct gtccaggccc tcggcccag   2820
gggcatcggg acagcacagt caccccagcc tggctggttg ggccttggag agtcctgttt   2880
gcacatccag gagcatctgg agcaaggagg gtagctggga tgtgaaccca gagggccctg   2940
```

-continued

```
caagcacttt acttcctgcc cctcccattg tgaaccccac agccctctcc aaagatacct    3000
ctgaggctgt ccagctcagc tggcttctta ggaactgtac tgacccagct gccctcaccc    3060
cagggccaac acagaatgaa cagccaaggc caaaaaaaaa aaaaaaaaaa aaaaaaaaaa    3120
aaaaaaaaaa aaaaaaaaaa aaaaaaaaaa aaaa                                3154

<210> SEQ ID NO 12
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 12
actgtcgttc cccgtgtgt                                                   19

<210> SEQ ID NO 13
<211> LENGTH: 27
<212> TYPE: DNA
<213> ORGANISM: Artificial sequence
<220> FEATURE:
<223> OTHER INFORMATION: Single strand DNA oligonuclotide

<400> SEQUENCE: 13
ttcagcaaag tataaagaca aatacaa                                          27

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 14
tgtgtggaag gcagaagcta                                                  20

<210> SEQ ID NO 15
<211> LENGTH: 24
<212> TYPE: DNA
<213> ORGANISM: Artificial sequence
<220> FEATURE:
<223> OTHER INFORMATION: Single strand DNA oligonuclotide

<400> SEQUENCE: 15
gctttctcct cctaacattt atcc                                             24

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 16
ctttaaggga ggcagtggtg                                                  20

<210> SEQ ID NO 17
<211> LENGTH: 18
<212> TYPE: DNA
<213> ORGANISM: Artificial sequence
<220> FEATURE:
<223> OTHER INFORMATION: Single strand DNA oligonuclotide

<400> SEQUENCE: 17
tcctggcctc ggtgatct                                                    18
```

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 18
gccaatcctt gcttcctttt                                              20

<210> SEQ ID NO 19
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 19
atgggctgag gtggaggta                                               19

<210> SEQ ID NO 20
<211> LENGTH: 18
<212> TYPE: DNA
<213> ORGANISM: Artificial sequence
<220> FEATURE:
<223> OTHER INFORMATION: Single strand DNA oligonuclotide

<400> SEQUENCE: 20
atgagcgacg caaacacc                                                18

<210> SEQ ID NO 21
<211> LENGTH: 18
<212> TYPE: DNA
<213> ORGANISM: Artificial sequence
<220> FEATURE:
<223> OTHER INFORMATION: Single strand DNA oligonuclotide

<400> SEQUENCE: 21
tacctgtggg gcggagat                                                18

<210> SEQ ID NO 22
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 22
gggactctct ggccatcat                                               19

<210> SEQ ID NO 23
<211> LENGTH: 18
<212> TYPE: DNA
<213> ORGANISM: Artificial sequence
<220> FEATURE:
<223> OTHER INFORMATION: Single strand DNA oligonuclotide

<400> SEQUENCE: 23
ctacccagtg cccccagt                                                18

<210> SEQ ID NO 24
<211> LENGTH: 20
<212> TYPE: DNA
<213> ORGANISM: Artificial sequence
<220> FEATURE:

<223> OTHER INFORMATION: Single strand DNA oligonuclotide

<400> SEQUENCE: 24
gcgagaagtg ggatcaccta                                          20

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 25
ggtgacacag caagactcca                                          20

<210> SEQ ID NO 26
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 26
atggggccga ctgttactg                                           19

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 27
gtttgggaga agccaagagc                                          20

<210> SEQ ID NO 28
<211> LENGTH: 18
<212> TYPE: DNA
<213> ORGANISM: Artificial sequence
<220> FEATURE:
<223> OTHER INFORMATION: Single strand DNA oligonuclotide

<400> SEQUENCE: 28
gcagagggca gggtacag                                            18

<210> SEQ ID NO 29
<211> LENGTH: 18
<212> TYPE: DNA
<213> ORGANISM: Artificial sequence
<220> FEATURE:
<223> OTHER INFORMATION: Single strand DNA oligonuclotide

<400> SEQUENCE: 29 cccccctagag cagcatcc                                           18

<210> SEQ ID NO 30
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 30
catgggcaac agagtgagg                                           19

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 31
gatgcaaatt tgggtgcttt                                               20

<210> SEQ ID NO 32
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 32
aaatggaagg gagggagcta                                               20

<210> SEQ ID NO 33
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 33
gtctctgggc ctgaccaac                                                19

<210> SEQ ID NO 34
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 34
gttggtcagg cccagagac                                                19

<210> SEQ ID NO 35
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 35
ctcggatggc atcttggtat                                               20

<210> SEQ ID NO 36
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 36
gaaagctcga atgcacgag                                                19

<210> SEQ ID NO 37
<211> LENGTH: 19
<212> TYPE: DNA
<213> ORGANISM: Artificial sequence
<220> FEATURE:
<223> OTHER INFORMATION: Single strand DNA oligonuclotide

```
<400> SEQUENCE: 37
gctggaggaa caggagctt                                                19

<210> SEQ ID NO 38
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 38
ggaatctgca tctccaccat                                               20

<210> SEQ ID NO 39
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 39
caagcgatcc tcccatctt                                                19

<210> SEQ ID NO 40
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 40
accctgatcc ttggggact                                                19

<210> SEQ ID NO 41
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 41
cttgcggccc tctaggaag                                                19

<210> SEQ ID NO 42
<211> LENGTH: 23
<212> TYPE: DNA
<213> ORGANISM: Artificial sequence
<220> FEATURE:
<223> OTHER INFORMATION: Single strand DNA oligonuclotide

<400> SEQUENCE: 42
gtaagccaca tccaccagag gta                                           23

<210> SEQ ID NO 43
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 43
acagcagctg gaccttgact                                               20

<210> SEQ ID NO 44
<211> LENGTH: 20
```

```
<212> TYPE: DNA
<213> ORGANISM: Artificial sequence
<220> FEATURE:
<223> OTHER INFORMATION: Single strand DNA oligonuclotide

<400> SEQUENCE: 44
ccctcgtcaa ggaagaatga                                              20

<210> SEQ ID NO 45
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 45
tacagtcctc cgccaacttt                                              20

<210> SEQ ID NO 46
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 46
ctgggcaaca tcactgaaac                                              20

<210> SEQ ID NO 47
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 47
agagcctttg catgctctgt                                              20

<210> SEQ ID NO 48
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 48
ccactggggg aagagaagg                                               19

<210> SEQ ID NO 49
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 49
aggaggcagg aaatctaggg                                              20

<210> SEQ ID NO 50
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 50
```

-continued cggtttgact tccctatcc                                          20

<210> SEQ ID NO 51
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 51
acccggtcag tcttgaacag                                         20

<210> SEQ ID NO 52
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 52
ggttcacaag gggtgagcta                                         20

<210> SEQ ID NO 53
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 53
acaggctcat agagggctca                                         20

<210> SEQ ID NO 54
<211> LENGTH: 21
<212> TYPE: DNA
<213> ORGANISM: Artificial sequence
<220> FEATURE:
<223> OTHER INFORMATION: Single strand DNA oligonuclotide

<400> SEQUENCE: 54
cagtcttgtt ctcccttgtc c                                       21

<210> SEQ ID NO 55
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 55
gaaaggtttt gcagcaggag                                         20

<210> SEQ ID NO 56
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 56
cagcccagtg tgtcttttga                                         20

<210> SEQ ID NO 57
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 57
cagatatgca tccctgagca                          20

<210> SEQ ID NO 58
<211> LENGTH: 18
<212> TYPE: DNA
<213> ORGANISM: Artificial sequence
<220> FEATURE:
<223> OTHER INFORMATION: Single strand DNA oligonuclotide

<400> SEQUENCE: 58
cttggggatg ggcacagt                            18

<210> SEQ ID NO 59
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 59
gtctggttcg tggctgtgt                           19

<210> SEQ ID NO 60
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 60
cgctctatag gcggaatctg                          20

<210> SEQ ID NO 61
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 61
tggggaggaa caggaagtaa                          20

<210> SEQ ID NO 62
<211> LENGTH: 18
<212> TYPE: DNA
<213> ORGANISM: Artificial sequence
<220> FEATURE:
<223> OTHER INFORMATION: Single strand DNA oligonuclotide

<400> SEQUENCE: 62
gggtgttggg aaccatgc                            18

<210> SEQ ID NO 63
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 63
gggtgggtgg gaagaccta                           19

```
<210> SEQ ID NO 64
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 64
acgctgatcg agaatggaga                                              20

<210> SEQ ID NO 65
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 65
ttttctcacg ctcctcatcc                                              20

<210> SEQ ID NO 66
<211> LENGTH: 32
<212> TYPE: DNA
<213> ORGANISM: Artificial sequence
<220> FEATURE:
<223> OTHER INFORMATION: Single strand DNA oligonuclotide

<400> SEQUENCE: 66
gcctcgagcc atgagcgggt ttaattttgg ag                                32

<210> SEQ ID NO 67
<211> LENGTH: 32
<212> TYPE: DNA
<213> ORGANISM: Artificial sequence
<220> FEATURE:
<223> OTHER INFORMATION: Single strand DNA oligonuclotide

<400> SEQUENCE: 67
gctctagagt cgctcagtca aggtgatcc gg                                 32

<210> SEQ ID NO 68
<211> LENGTH: 3253
<212> TYPE: DNA
<213> ORGANISM: Homo sapiens
<220> FEATURE:
<221> NAME/KEY: misc_feature
<222> LOCATION: (1429)..(1429)
<223> OTHER INFORMATION: A to C missense mutation

<400> SEQUENCE: 68
actacttctg cgcctgcgcg accgtgattc cccgctcgcg actccccacc ccccagggct    60
ccctaaagag ggccacgagc tgcgaaaggg cgggaaaggc agttggagaa gaggtaagcg   120
gttactcact ccatggctgc agcaaggaga ggcggcggcg gcctcggctg aagaaagaag   180
aaatcttccc aaggctgcag acaccgacgg atttgctttg ggagccagag tagctgccgc   240
caccagagtc cggagccatg agcgggttta attttggagg cactgggggcc cctacaggcg   300 ggttcacgtt tggcactgca agacggcaa caaccacacc tgctacaggg ttttctttct   360
ccacctctgg cactggaggg tttaattttg gggctccctt ccaaccagcc acaagtaccc   420
cttccaccgg cctgttctca cttgccaccc agactccggc cacacagacg acaggcttca   480
cttttggaac agcgactctt gcttcggggg gaactggatt tcttttgggg atcggtgctt   540
caaagctcaa cttgagcaac acagctgcca ccccagccat ggcaaacccc agcggctttg   600
```

```
ggctgggcag cagcaacctc actaatgcca tatcgagcac cgtcacctcc agccagggca    660
cagcacccac cggctttgtg tttggcccct ccaccacctc tgtggctcca gctaccacat    720
ctggaggctt ctcattcact ggtggaagca cggcccaacc ctccggtttc aacattggct    780
cagcagggaa ttcagcccag cccacggcac ctgccacgtt gcccttcact ccggccacgc    840
cagcagccac cacagcaggt gccacacagc cagctgctcc cacacccaca gccaccatca    900
ccagtactgg gcccagcctc tttgcgtcaa tagcaactgc tccaacctca tctgccacca    960
ctggactctc cctctgtacc cctgtgacca cagcgggcgc ccccactgct gggacacagg   1020
gcttcagctt aaaggcacct ggagcagctt ccggcacctc cacaacaaca tccaccgctg   1080
ccaccgccac cgccaccacc accagcagca gcagcaccac cggctttgcc ttgaatttaa   1140
aaccactggc gccagccggg atcccagca atacagcagc tgccgtgacc gctccacctg   1200
gccctggcgc agctgcaggg gcggctgcca gctccgccat gacctacgcg cagctggaga   1260
gcctgatcaa caaatggagc ctggagctag aggaccagga gcggcacttc ctccagcagg   1320
ccacccaggt caacgcctgg gaccgcacgc tgatcgagaa tggagaaaag atcaccagcc   1380
tgcaccgcga ggtggagaag gtgaagctgg accagaagag gctggaccng agctcgact    1440 tcatcctgtc ccagcagaag gagctggaag acctgctgag cccactggag gagttggtca   1500
aggagcagag cgggaccatc tacctgcagc acgcggatga ggagcgtgag aaaacctaca   1560
agctggctga gaacatcgac gcacagctca gcgcatggc ccaggatctc aaggacatca   1620
tcgagcacct gaacacgtcc ggggcccccg ccgacaccag tgacccactg cagcagatct   1680
gcaagatcct caatgcgcac atggactcac tgcagtggat cgaccagaac tcggccctgc   1740
tgcagaggaa ggtggaggag gtgaccaagg tgtgcgaggg ccggcgcaag gagcaggagc   1800
gcagcttccg gatcacctt gactgagcga cagcagccct ggggcccgca ggtccctagg   1860
gagttcatga ggggaatgcg ccctgttgtc tgtagtttgg ggttgtggca agatacttgt   1920
ttgtttcttt cttctttca catgactgcc cttgacatga tcgctgtgtg ctttgcgttt   1980
ttccatttag gagggtattc tgggccttct gcccaggcag cagcctcatg ggtgtggctt   2040
ctgtggcttt catttgagta tctttggccc cttttcacct actgcgacca cccacctcat   2100
cctggctcag cctggtgatg gagaagtgct gatggtcttg gtcccagcca gggtcgtggg   2160
ggcagccact ctctccaaag catagtcata ggtgtcatga aaaatacca aatgtaagag   2220 aacctccaag tcagggcgca gtggctcacc cctgtaatct cagcactttg ggtggccaag   2280
gcgggcagat gacttgaggt caggagttcg agaccagcct ggccaacatg gtgaaacccc   2340
gtctctacta aaaatacaaa aattagtcag gtgtggtgga cgcctgtgat ctcaatctca   2400
gctactcggg aggctgaggc aggagaatca cttgaaccca ggaggtgttg cagtgaacca   2460
agatcacacc actgcactcc agcctaggca acagagactc tgtctcaaaa aaaaaaaaa   2520 aaaaaaagaa actcccagga gacagcagcc tagttttcga gtgtgagctt gtgcttgtga   2580
aagctaacca tgctaaccac caaggcaaag cagcacagtg tgaatagaac agagcgggat   2640
caagaatttc acagaagaca ggtcagctga ggggcctgca cacacagggt gttgaggaac   2700
cacagatggg cgccgagagg cctgcctttt gcctggccca ggctcacccc cacccttggg   2760
ctcacctcct ccaggaagcc ttcccagcta cccgaagctc aggtggcctt cttgcaggtc   2820
cccgtagcac cctgagcctg taccttgggt ggcacttgtt atgctatcct gtgctagccg   2880
tttgtgcctc gtctcgctgt tagattgtga gttcccatgg gcagagaccc actgtcgttc   2940
```

-continued

```
cccgtgtgtc cccagcccgg tccctgtcac atttgttaaa tgaaagaaca atgaagccca    3000
gtgtaacgtc agtccacaga aatagccaca gcttccagtg gtggccgtag acttggctcg    3060
gaacttagtg gcaccagagt aactctagtc agttacagta aaatccactg tgtgtggaag    3120
gcagaagcta gcggttgtat cccaagcatc ttttgtattt gtctttatac tttgctgaat    3180
tctctgaaat acctattact gtatgttgct tttctaaata aatgtattgt gaaaccaaaa    3240
aaaaaaaaaa aaa                                                       3253
```

<210> SEQ ID NO 69
<211> LENGTH: 522
<212> TYPE: PRT
<213> ORGANISM: Homo sapiens
<220> FEATURE:
<221> NAME/KEY: misc_feature
<222> LOCATION: (391)..(391)
<223> OTHER INFORMATION: Q to P mutation

<400> SEQUENCE: 69

```
Met Ser Gly Phe Asn Phe Gly Gly Thr Gly Ala Pro Thr Gly Gly Phe
1               5                   10                  15

Thr Phe Gly Thr Ala Lys Thr Ala Thr Thr Pro Ala Thr Gly Phe
            20                  25                  30

Ser Phe Ser Thr Ser Gly Thr Gly Gly Phe Asn Phe Gly Ala Pro Phe
        35                  40                  45

Gln Pro Ala Thr Ser Thr Pro Ser Thr Gly Leu Phe Ser Leu Ala Thr
    50                  55                  60

Gln Thr Pro Ala Thr Gln Thr Thr Gly Phe Thr Phe Gly Thr Ala Thr
65                  70                  75                  80

Leu Ala Ser Gly Gly Thr Gly Phe Ser Leu Gly Ile Gly Ala Ser Lys
                85                  90                  95

Leu Asn Leu Ser Asn Thr Ala Ala Thr Pro Ala Met Ala Asn Pro Ser
            100                 105                 110

Gly Phe Gly Leu Gly Ser Ser Asn Leu Thr Asn Ala Ile Ser Ser Thr
        115                 120                 125

Val Thr Ser Ser Gln Gly Thr Ala Pro Thr Gly Phe Val Phe Gly Pro
    130                 135                 140

Ser Thr Thr Ser Val Ala Pro Ala Thr Thr Ser Gly Gly Phe Ser Phe
145                 150                 155                 160

Thr Gly Gly Ser Thr Ala Gln Pro Ser Gly Phe Asn Ile Gly Ser Ala
                165                 170                 175

Gly Asn Ser Ala Gln Pro Thr Ala Pro Ala Thr Leu Pro Phe Thr Pro
            180                 185                 190

Ala Thr Pro Ala Ala Thr Thr Ala Gly Ala Thr Gln Pro Ala Ala Pro
        195                 200                 205

Thr Pro Thr Ala Thr Ile Thr Ser Thr Gly Pro Ser Leu Phe Ala Ser
    210                 215                 220

Ile Ala Thr Ala Pro Thr Ser Ser Ala Thr Thr Gly Leu Ser Leu Cys
225                 230                 235                 240

Thr Pro Val Thr Thr Ala Gly Ala Pro Thr Ala Gly Thr Gln Gly Phe
                245                 250                 255

Ser Leu Lys Ala Pro Gly Ala Ala Ser Gly Thr Ser Thr Thr Thr Ser
            260                 265                 270

Thr Ala Ala Thr Ala Thr Ala Thr Thr Thr Ser Ser Ser Ser Thr Thr
        275                 280                 285

Gly Phe Ala Leu Asn Leu Lys Pro Leu Ala Pro Ala Gly Ile Pro Ser
```

```
            290                 295                 300
Asn Thr Ala Ala Ala Val Thr Ala Pro Pro Gly Pro Gly Ala Ala Ala
305                 310                 315                 320

Gly Ala Ala Ala Ser Ser Ala Met Thr Tyr Ala Gln Leu Glu Ser Leu
                325                 330                 335

Ile Asn Lys Trp Ser Leu Glu Leu Glu Asp Gln Glu Arg His Phe Leu
                340                 345                 350

Gln Gln Ala Thr Gln Val Asn Ala Trp Asp Arg Thr Leu Ile Glu Asn
                355                 360                 365

Gly Glu Lys Ile Thr Ser Leu His Arg Glu Val Glu Lys Val Lys Leu
            370                 375                 380

Asp Gln Lys Arg Leu Asp Xaa Glu Leu Asp Phe Ile Leu Ser Gln Gln
385                 390                 395                 400

Lys Glu Leu Glu Asp Leu Leu Ser Pro Leu Glu Leu Val Lys Glu
                405                 410                 415

Gln Ser Gly Thr Ile Tyr Leu Gln His Ala Asp Glu Glu Arg Glu Lys
            420                 425                 430

Thr Tyr Lys Leu Ala Glu Asn Ile Asp Ala Gln Leu Lys Arg Met Ala
                435                 440                 445

Gln Asp Leu Lys Asp Ile Ile Glu His Leu Asn Thr Ser Gly Ala Pro
            450                 455                 460

Ala Asp Thr Ser Asp Pro Leu Gln Gln Ile Cys Lys Ile Leu Asn Ala
465                 470                 475                 480

His Met Asp Ser Leu Gln Trp Ile Asp Gln Asn Ser Ala Leu Leu Gln
                485                 490                 495

Arg Lys Val Glu Glu Val Thr Lys Val Cys Glu Gly Arg Arg Lys Glu
            500                 505                 510

Gln Glu Arg Ser Phe Arg Ile Thr Phe Asp
            515                 520

<210> SEQ ID NO 70
<211> LENGTH: 903
<212> TYPE: PRT
<213> ORGANISM: Pan troglodytes

<400> SEQUENCE: 70

Met His Lys Arg Lys Gly Pro Pro Gly Pro Gly Arg Gly Ala Ala
1               5                   10                  15

Ala Ala Arg Gln Leu Gly Leu Leu Val Asp Leu Ser Pro Asp Gly Leu
                20                  25                  30

Met Ile Pro Glu Asp Gly Ala Asn Asp Glu Glu Leu Glu Ala Glu Phe
            35                  40                  45

Leu Ala Leu Val Gly Gly Gln Pro Ala Leu Glu Lys Leu Lys Gly
    50                  55                  60

Lys Gly Pro Leu Pro Met Glu Ala Ile Glu Lys Met Ala Ser Leu Cys
65                  70                  75                  80

Met Arg Asp Pro Asp Glu Asp Glu Glu Gly Thr Asp Glu Asp
                85                  90                  95

Leu Glu Ala Asp Asp Asp Leu Leu Ala Glu Leu Asn Glu Val Leu Gly
                100                 105                 110

Glu Glu Gln Lys Pro Ser Glu Thr Pro Pro Val Ala Gln Pro Lys
            115                 120                 125

Pro Glu Ala Pro His Pro Gly Leu Glu Thr Thr Leu Gln Glu Arg Leu
    130                 135                 140
```

```
Ala Leu Tyr Arg Thr Ala Ile Glu Ser Ala Arg Gln Ala Gly Asp Ser
145                 150                 155                 160

Ala Lys Met Arg Arg Tyr Asp Arg Gly Leu Lys Thr Leu Glu Asn Leu
            165                 170                 175

Leu Ala Ser Val Arg Lys Gly Asn Ala Ile Asp Glu Ala Asp Ile Pro
        180                 185                 190

Pro Pro Val Ala Ile Gly Lys Gly Pro Ala Ser Thr Pro Thr Tyr Ser
    195                 200                 205

Pro Ala Pro Thr Gln Pro Ala Pro Gly Ile Ala Ser Ala Pro Glu Pro
210                 215                 220

Arg Val Thr Leu Glu Gly Pro Ser Pro Thr Ala Pro Ala Ser Ser Pro
225                 230                 235                 240

Gly Leu Ala Lys Pro Gln Met Pro Pro Gly Pro Cys Ser Pro Gly Pro
                245                 250                 255

Leu Ala Gln Leu Gln Ser Arg Gln Arg Asp Tyr Lys Leu Ala Ala Leu
            260                 265                 270

His Ala Lys Gln Gln Gly Asp Thr Thr Ala Ala Ala Arg His Phe Arg
        275                 280                 285

Val Ala Lys Ser Phe Asp Ala Val Leu Glu Ala Leu Ser Arg Gly Glu
    290                 295                 300

Pro Val Asp Leu Ser Cys Leu Pro Pro Pro Asp Gln Leu Pro Pro
305                 310                 315                 320

Asp Pro Pro Ser Pro Ser Gln Pro Pro Thr Pro Ala Met Ala Pro
                325                 330                 335

Ser Thr Pro Glu Val Pro Pro Pro Arg Thr Leu Leu Glu Ala Leu
            340                 345                 350

Glu Gln Arg Met Glu Arg Tyr Gln Val Ala Ala Ala Gln Ala Lys Ser
        355                 360                 365

Lys Gly Asp Gln Arg Lys Ala Arg Met His Glu Arg Ile Val Lys Gln
    370                 375                 380

Tyr Gln Asp Ala Ile Arg Ala His Lys Ala Gly Arg Ala Val Asp Val
385                 390                 395                 400

Ala Glu Leu Pro Val Pro Gly Phe Pro Pro Ile Gln Gly Leu Glu
                405                 410                 415

Ala Thr Lys Pro Thr Gln Gln Ser Leu Val Gly Val Leu Glu Thr Ala
            420                 425                 430

Met Lys Leu Ala Asn Gln Glu Glu Gly Pro Glu Asp Glu Glu Asp Glu
        435                 440                 445

Val Pro Lys Lys Gln Asn Ser Pro Val Ala Pro Thr Ala Gln Pro Lys
    450                 455                 460

Ala Pro Pro Ser Arg Ala Pro Gln Ser Gly Ser Ala Pro Ala Ala Lys
465                 470                 475                 480

Ala Pro Pro Lys Ala Thr Ser Thr Arg Ala Gln Gln Gln Leu Ala Phe
                485                 490                 495

Leu Glu Gly Arg Lys Lys Gln Leu Leu Gln Ala Ala Leu Arg Ala Lys
            500                 505                 510

Gln Lys Asn Asp Val Glu Gly Ala Lys Met His Leu Arg Gln Ala Lys
        515                 520                 525

Gly Leu Glu Pro Met Leu Glu Ala Ser Arg Asn Gly Leu Pro Val Asp
    530                 535                 540

Ile Thr Lys Met Cys Leu Asn His Ser Asn Gln Phe Thr Gln Leu Gly
545                 550                 555                 560

Asn Ile Thr Glu Thr Thr Lys Phe Glu Lys Leu Ala Glu Asp Cys Lys
```

-continued

```
                565                 570                 575
Arg Ser Met Asp Ile Leu Lys Gln Ala Phe Ala Arg Gly Leu Pro Thr
            580                 585                 590
Pro Thr Ala Arg Phe Glu Gln Arg Thr Phe Ser Val Ile Lys Ile Phe
        595                 600                 605
Pro Asp Leu Ser Ser Asn Asp Met Leu Leu Phe Ile Val Lys Gly Ile
    610                 615                 620
Asn Leu Pro Thr Pro Pro Gly Leu Ser Pro Gly Asp Leu Asp Val Phe
625                 630                 635                 640
Val Arg Phe Asp Phe Pro Tyr Pro Asn Val Glu Glu Ala Gln Lys Asp
                645                 650                 655
Lys Thr Ser Val Ile Lys Asn Thr Asp Ser Pro Glu Phe Lys Glu Gln
            660                 665                 670
Phe Lys Leu Cys Ile Asn Arg Ser His Arg Gly Phe Arg Arg Ala Ile
        675                 680                 685
Gln Thr Lys Gly Ile Lys Phe Glu Val Val His Lys Gly Gly Leu Phe
    690                 695                 700
Lys Thr Asp Arg Val Leu Gly Thr Ala Gln Leu Lys Leu Asp Ala Leu
705                 710                 715                 720
Glu Thr Ala Cys Glu Val Arg Glu Ile Leu Glu Val Leu Asp Gly Arg
                725                 730                 735
Arg Pro Thr Gly Gly Arg Leu Glu Val Met Val Arg Ile Arg Glu Pro
            740                 745                 750
Leu Thr Ala Gln Gln Leu Glu Thr Thr Thr Glu Arg Trp Leu Val Ile
        755                 760                 765
Asp Pro Val Pro Ala Ala Val Pro Thr Val Ala Gly Pro Lys Gly Lys
    770                 775                 780
Ala Pro Pro Val Pro Ala Pro Ala Arg Glu Ser Gly Asn Arg Ser Ala
785                 790                 795                 800
Arg Pro Leu His Ser Leu Ser Val Leu Ala Phe Asp Gln Glu Arg Leu
                805                 810                 815
Glu Arg Lys Ile Leu Ala Leu Arg Gln Ala Arg Arg Pro Val Pro Pro
            820                 825                 830
Glu Val Ala Gln Gln Tyr Gln Asp Ile Met Gln Arg Ser Gln Trp Gln
        835                 840                 845
Arg Ala Gln Leu Glu Gln Gly Gly Val Gly Ile Arg Arg Glu Tyr Ala
    850                 855                 860
Ala Gln Leu Glu Arg Gln Leu Gln Phe Tyr Thr Glu Ala Ala Arg Arg
865                 870                 875                 880
Leu Gly Asn Asp Gly Ser Arg Asp Ala Ala Lys Glu Ala Leu Tyr Arg
                885                 890                 895
Arg Asn Leu Val Glu Ser Glu
            900

<210> SEQ ID NO 71
<211> LENGTH: 936
<212> TYPE: PRT
<213> ORGANISM: Tetraodon nigroviridis

<400> SEQUENCE: 71

Met Phe Ser Lys Arg Lys Pro Ala Gln Pro Arg Gly Gln Gly Ala Ala
1               5                   10                  15
Ala Ala Gln Gln Met Gly Leu Tyr Leu Glu Leu Asp Pro Glu Gln Met
            20                  25                  30
```

-continued

```
Val Met Glu Gly Asn Leu Asp Asp Pro Asp Leu Glu Ala Glu Leu Ala
         35                  40                  45
Ala Ile Thr Gly Asn Lys Ala Gly Ala Gly Lys Ala Lys Pro Lys
 50                  55                  60
Arg Lys Ser Pro Leu Pro Met Glu Asp Ile Ala Lys Met Ala Asp Glu
 65                  70                  75                  80
Cys Leu Arg Asp Ile Asp Glu Asp Asp Gly Asn Ile Glu Asp
                     85                  90                  95
Asp Gln Asp Leu Leu Ala Glu Leu Gln Glu Val Val Gly Val Asp Glu
                100                 105                 110
Asp Asp Glu Asp Ala Ala Gly Thr Ser Ser Pro Ser Pro Ala Glu
                115                 120                 125
Thr Pro Glu Ser Pro Pro Ser Gln Val Gln Pro Thr Pro Leu Ser Cys
    130                 135                 140
Ser Pro Val Lys Pro Gln Gly Ala Lys Thr Pro Ser Ala Ala Pro Ala
145                 150                 155                 160
Gly Leu Gln His Thr Leu Glu Arg Ile Ser Met Tyr Gln Thr Ala
                    165                 170                 175
Leu Gln Asn Ser Lys Ala Ala Gly Glu Ala Ser Lys Val Arg Arg Tyr
                180                 185                 190
Asp Arg Gly Leu Lys Thr Leu Gln Thr Met Leu Thr Ala Ala Lys Lys
                195                 200                 205
Gly Arg Pro Val Asn Glu Ala Glu Met Pro Pro Val Ala Thr Gly
                210                 215                 220
Ala Gln Gly Pro Asp Gly Gly Ser Ala Ala Pro Arg Arg Pro Ala Pro
225                 230                 235                 240
Pro Ile Pro Ser Pro Pro Ala Pro Ser Ala Ala Pro Ser Pro Glu
                    245                 250                 255
Glu Pro Ala Glu Glu Pro Ala Gly Gln Pro Gln Thr Ala Glu Asp Gln
                260                 265                 270
Ala Lys Lys Thr Ala Leu Arg Glu Thr Gln Lys Glu Tyr Arg Met Ala
                275                 280                 285
Ala Leu Ser Ala Lys Lys Gln Gly Asp Leu Glu Gln Ala Arg Leu Tyr
                290                 295                 300
Leu Met Ala Ser Lys Thr Ile Asp Ala Ala Ile Gln Ala Val Glu Lys
305                 310                 315                 320
Gly Glu Asp Val Arg Leu Gly Ser Leu Pro Pro Leu Pro Gly Gln Gly
                    325                 330                 335
Gly Ser Ala Ala Leu Gln Arg Ser Ser Ser Gly Gln Ser Val Pro Ala
                340                 345                 350
Gly Gln Pro Ala Ala Glu Ala Pro Ala Ala Phe Pro Ala Ala Pro
                355                 360                 365
Ala Ser Pro Gly Asn Val Leu Glu Ala Leu Glu Gln Arg Arg Ala Lys
    370                 375                 380
Tyr Ala Glu Ala Ser Ser Gln Ala Lys Ala Ser Gly Asp Glu Arg Lys
385                 390                 395                 400
Ala Arg Met His Gln Arg Ile Ser Gln Gln Tyr Gln Ser Ala Ile Arg
                    405                 410                 415
Ala His Lys Ala Gly Lys Ala Val Asn Phe Gln Glu Leu Pro Thr Pro
                420                 425                 430
Pro Gly Phe Pro Pro Ile Pro Gly Gln Ser Asn Thr Gly Gly Glu His
                435                 440                 445
Gly Leu Val Ala Ala Leu Val Ala Ala Asp Lys Leu Thr Ala Ala Asp
```

-continued

```
            450                 455                 460
Ala Gly Glu Thr Ala Ala Gly Thr Asp Glu Glu Ser Gln Ser Ala
465                 470                 475                 480

Glu Pro Gly Glu Pro Ile Lys Pro Pro Asp Ala Ser Gly Gly Val Gln
                485                 490                 495

Ser Arg Lys Thr Thr Pro Ser Pro Ser Ser Ser Ser Pro Glu Gln
                500                 505                 510

Ala Val Ser Ala Gly Gln Leu Ser Pro Thr Ala Ala Gln Leu Glu
                515                 520                 525

Leu Leu Glu Gly Arg Arg Lys Gln Tyr Met Arg Ala Ala Leu Gln Ala
530                 535                 540

Lys Gln Lys Gln Asp Val Glu Gln Ala Lys Ala Leu Leu Arg Thr Ala
545                 550                 555                 560

Lys Ser Leu Glu Pro Leu Ile Gln Ala Val His Ala Gly Thr Ala Val
                565                 570                 575

Asp Thr Ser Thr Val Ser Ala Ala Pro Pro Leu Pro His Ser Ser Val
                580                 585                 590

Ala Lys Asp Ser Asp Glu Lys Lys Val Glu Ala Ser Thr Glu Lys Thr
                595                 600                 605

Leu Val Leu Gly Tyr Phe Arg Gly Gly Val Gly Gly Thr Cys Gly
                610                 615                 620

Arg His Thr Val Met Ser Pro Gln Val Pro Ser Pro Gly Asp Glu
625                 630                 635                 640

Asp Glu Asp Phe Ile Leu Val His His Ser Asp Val Gln Leu Ser Asp
                645                 650                 655

Lys Ala Glu Gln Val Tyr Ala Gln Leu Met Lys Ile Leu Arg Glu Gln
                660                 665                 670

Tyr Glu Val Gly Leu Arg Gly Gly Arg Leu Asp Thr Pro Arg Pro Pro
                675                 680                 685

Lys Ser Arg Ser Asp Ser Leu Trp Arg Leu Ser Val Leu Leu Ile Ala
                690                 695                 700

Ala Ser Leu Ser Phe Ser Gln Lys Cys Arg Thr His Ser Glu Gln Phe
705                 710                 715                 720

Thr His Leu Gly Ser Val Ala Glu Thr Thr Lys Phe Glu Gln Met Ala
                725                 730                 735

Glu Ser Cys Lys Lys Ser Leu Glu Val Leu Lys Leu Ala Gln Ser Arg
                740                 745                 750

Gly Leu Pro Pro Pro Lys His Thr Phe Glu Glu Arg Ser Phe His Thr
                755                 760                 765

Val Arg Ile Phe Pro Glu Leu Ser Ser Thr Asp Met Val Val Ile Ile
                770                 775                 780

Val Lys Gly Met Asn Leu Pro Ala Pro Ser Gly Ile Gln Pro Asn Asp
785                 790                 795                 800

Leu Asp Ala Tyr Val Lys Phe Asp Phe Pro Tyr Pro Ser Thr Glu Gln
                805                 810                 815

Pro Gln Lys His Arg Thr Ser Val Ile Lys Asn Thr Asn Cys Pro Glu
                820                 825                 830

Tyr Asn Gln Ser Phe Thr Leu Ser Ile Asn Arg Ser His Arg Gly Phe
                835                 840                 845

Arg Arg Val Val Ala Ser Arg Gly Leu Lys Leu Glu Leu Leu His Lys
                850                 855                 860

Gly Gly Phe Leu Arg Ser Asp Lys Pro Ile Gly Thr Ala Val Val Lys
865                 870                 875                 880
```

Leu Asp Lys Leu Glu Thr Gln Ser Glu Ile Arg Glu Ile Val Glu Val
           885                 890                 895

Met Asn Gly Arg Lys Pro Thr Gly Gly Arg Val Glu Val Lys Val Arg
           900                 905                 910

Leu Arg Glu Pro Leu Ser Gly Gln Asp Met Gln Thr Ser Arg Glu Arg
           915                 920                 925

Trp Leu Val Ile Ser His Ser Gln
           930             935

<210> SEQ ID NO 72
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 72
ccactggaag ctgtggctat                                              20

<210> SEQ ID NO 73
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 73
ccagggctcc ctaaagagg                                               19

<210> SEQ ID NO 74
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 74
catggctctg tagcctcgac                                              20

<210> SEQ ID NO 75
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 75
gaggtggatg tccgtctttt                                              20

<210> SEQ ID NO 76
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 76
cagctactct ggctcccaaa                                              20

<210> SEQ ID NO 77
<211> LENGTH: 20
<212> TYPE: DNA
<213> ORGANISM: Artificial sequence
<220> FEATURE:

<223> OTHER INFORMATION: Single strand DNA oligonuclotide

<400> SEQUENCE: 77
ccaaaactgc catctgacaa                                               20

<210> SEQ ID NO 78
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 78
taaaccctcc agtgccagag                                               20

<210> SEQ ID NO 79
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 79
actgcaaaga cggcaacaac                                               20

<210> SEQ ID NO 80
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 80
gcagctgtgt tgctcaagtt                                               20

<210> SEQ ID NO 81
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 81
atatcgagca ccgtcacctc                                               20

<210> SEQ ID NO 82
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 82
ctgctgagcc aatgttgaaa                                               20

<210> SEQ ID NO 83
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 83
aaccctccgg tttcaacatt                                               20

```
<210> SEQ ID NO 84
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 84
ctccaggtgc ctttaagctg                                                   20

<210> SEQ ID NO 85
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 85
cacctccaca acaacatcca                                                   20

<210> SEQ ID NO 86
<211> LENGTH: 18
<212> TYPE: DNA
<213> ORGANISM: Artificial sequence
<220> FEATURE:
<223> OTHER INFORMATION: Single strand DNA oligonuclotide

<400> SEQUENCE: 86
gtcccaggcg ttgacctg                                                     18

<210> SEQ ID NO 87
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 87
acgctgatcg agaatggaga                                                   20

<210> SEQ ID NO 88
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 88
ttttctcacg ctcctcatcc                                                   20

<210> SEQ ID NO 89
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 89
acatcgatgc acagctcaag                                                   20

<210> SEQ ID NO 90
<211> LENGTH: 19
<212> TYPE: DNA
<213> ORGANISM: Artificial sequence
<220> FEATURE:
<223> OTHER INFORMATION: Single strand DNA oligonuclotide
```

<400> SEQUENCE: 90
aaaggtgatc cggaagctg                                               19

<210> SEQ ID NO 91
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 91
ccctagggag ttcatgagg                                               19

<210> SEQ ID NO 92
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 92
ggtcgcagta ggtgaaaagg                                              20

<210> SEQ ID NO 93
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 93 ttggccccctt ttcacctact                                             20

<210> SEQ ID NO 94
<211> LENGTH: 21
<212> TYPE: DNA
<213> ORGANISM: Artificial sequence
<220> FEATURE:
<223> OTHER INFORMATION: Single strand DNA oligonuclotide

<400> SEQUENCE: 94
tcctgacctc aagtcatctg c                                            21

<210> SEQ ID NO 95
<211> LENGTH: 19
<212> TYPE: DNA
<213> ORGANISM: Artificial sequence
<220> FEATURE:
<223> OTHER INFORMATION: Single strand DNA oligonuclotide

<400> SEQUENCE: 95
cgggcagatg acttgaggt                                               19

<210> SEQ ID NO 96
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 96
ccttggtggt tagcatggtt                                              20

<210> SEQ ID NO 97
<211> LENGTH: 21

```
<212> TYPE: DNA
<213> ORGANISM: Artificial sequence
<220> FEATURE:
<223> OTHER INFORMATION: Single strand DNA oligonuclotide

<400> SEQUENCE: 97
gctaaccatg ctaaccacca a                                        21

<210> SEQ ID NO 98
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 98
cccatgggaa ctcacaatct                                          20

<210> SEQ ID NO 99
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 99
tagcaccctg agcctgtacc                                          20

<210> SEQ ID NO 100
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 100
gggagcttga cattggacat                                          20

<210> SEQ ID NO 101
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 101
ggggtaagga ggacaagcag                                          20

<210> SEQ ID NO 102
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 102
ttggtctcca tcctgacaca                                          20

<210> SEQ ID NO 103
<211> LENGTH: 20
<212> TYPE: DNA
<213> ORGANISM: Artificial sequence
<220> FEATURE:
<223> OTHER INFORMATION: Single strand DNA oligonuclotide

<400> SEQUENCE: 103
```

```
tcccaaagtg ctgggactac                                                   20
```

<210> SEQ ID NO 104
<211> LENGTH: 20
<212> TYPE: DNA
<213> ORGANISM: Artificial sequence
<220> FEATURE:
<223> OTHER INFORMATION: Sequencing information from a normal
      (unaffected with NSMR) individual

<400> SEQUENCE: 104

```
aatcacttga ggccaggagt                                                   20
```

<210> SEQ ID NO 105
<211> LENGTH: 20
<212> TYPE: DNA
<213> ORGANISM: Artificial sequence
<220> FEATURE:
<223> OTHER INFORMATION: Sequencing information from a NSMR affected
      individual

<400> SEQUENCE: 105

```
aatcacttga acccgggagg                                                   20
```

<210> SEQ ID NO 106
<211> LENGTH: 17
<212> TYPE: DNA
<213> ORGANISM: Artificial sequence
<220> FEATURE:
<223> OTHER INFORMATION: Sequencing information from a normal
      (unaffected with IBSN) individual

<400> SEQUENCE: 106

```
aggctggacc aggagct                                                      17
```

<210> SEQ ID NO 107
<211> LENGTH: 17
<212> TYPE: DNA
<213> ORGANISM: Artificial sequence
<220> FEATURE:
<223> OTHER INFORMATION: Sequencing information from an IBSN affected
      individual

<400> SEQUENCE: 107

```
aggctggacc cggagct                                                      17
```

<210> SEQ ID NO 108
<211> LENGTH: 222
<212> TYPE: PRT
<213> ORGANISM: Homo sapiens

<400> SEQUENCE: 108

```
Gly Ile Pro Ser Asn Thr Ala Ala Val Thr Ala Pro Gly Pro
1               5                   10                  15

Gly Ala Ala Ala Gly Ala Ala Ala Ser Ser Ala Met Thr Tyr Ala Gln
                20                  25                  30

Leu Glu Ser Leu Ile Asn Lys Trp Ser Leu Glu Leu Glu Asp Gln Glu
            35                  40                  45

Arg His Phe Leu Gln Gln Ala Thr Gln Val Asn Ala Trp Asp Arg Thr
        50                  55                  60

Leu Ile Glu Asn Gly Glu Lys Ile Thr Ser Leu His Arg Glu Val Glu
65                  70                  75                  80

Lys Val Lys Leu Asp Gln Lys Arg Leu Asp Gln Glu Leu Asp Phe Ile
                85                  90                  95
```

```
Leu Ser Gln Gln Lys Glu Leu Glu Asp Leu Leu Ser Pro Leu Glu Glu
            100                 105                 110

Leu Val Lys Glu Gln Ser Gly Thr Ile Tyr Leu Gln His Ala Asp Glu
        115                 120                 125

Glu Arg Glu Lys Thr Tyr Lys Leu Ala Glu Asn Ile Asp Ala Gln Leu
    130                 135                 140

Lys Arg Met Ala Gln Asp Leu Lys Asp Ile Ile Glu His Leu Asn Thr
145                 150                 155                 160

Ser Gly Ala Pro Ala Asp Thr Ser Asp Pro Leu Gln Gln Ile Cys Lys
                165                 170                 175

Ile Leu Asn Ala His Met Asp Ser Leu Gln Trp Ile Asp Gln Asn Ser
            180                 185                 190

Ala Leu Leu Gln Arg Lys Val Glu Glu Val Thr Lys Val Cys Glu Gly
        195                 200                 205

Arg Arg Lys Glu Gln Glu Arg Ser Phe Arg Ile Thr Phe Asp
    210                 215                 220

<210> SEQ ID NO 109
<211> LENGTH: 3590
<212> TYPE: DNA
<213> ORGANISM: Homo sapiens
<220> FEATURE:
<221> NAME/KEY: misc_feature
<223> OTHER INFORMATION: genomic sequence set forth by nucleotides
      13891337-13894926 of GenBank Accession No. NC_000019.8

<400> SEQUENCE: 109
ggccaggagt tcaagaccag cttgggcaac gtggcaagac cccgtggcta caagaaattt      60
aaaaattagc ctggtgtggt ggtgcacacc tgcagtccca ctctagatca tgccactgta     120
ctccagcctg ggcaacagag cgagatcctg tctcaaaaaa aaaaaaatta attaattaaa     180
aaaagtaaag gcccaagact ctataggtgg gagaggaatc tgcatctcca ccataatggt     240
gtgagttggt ctccatcctg acacacaata accaggcctc gactggccac ccaggcttcc     300
ccccaatcca gggcctggag gccaccaagc cacccagca gagtctggtg ggtgtcctgg     360
agactgccat gaagctggcc aaccaggatg aaggcccaga ggatgaagag gatgaggtgc     420
ctaagaaggt ttgagggttg gggccgggcg cagtggctca cacctgtagt cccagcactt     480
tgggaatcca agatgggagg atcgcttgag gccaggagtt tgagaccatc ctgggccaca     540
cagtgagacc cccgtctcta caaaaaaatt ttttaaaatt agccaggcat ggtgggactc     600
acctgtagtc cctgctactt gggagactga ggtgggagga tcacctgaac taaggagttc     660
aaggctgcag tgagccatgg tcatgccact gtacgccagt ctgggtgaca gagcaagacc     720
tcatctccaa gacaattaaa aaaaaaaaaa agtgtttggt gagaattgct tgaaccggga     780
ggcagaggtt gcagtgagcc aagatcgtgc tactgcactc cagcctggac gatacagtga     840
tactctgtct caaaaagaa aaaaaaaaa aaaaggtgt ttggggccag gggctttgag     900
tgaggcaggg gagtagcaaa gtcctgggag cccactaaat gaccactgtt gtcaccatca     960
gaccctgatc cttggggact ggactcatca caggcgctac gaaatctcta acatcctctc    1020
tcttcctcta cagcagaaca gccctgtggc cccacagcc cagcccaaag ccccacccctc    1080 aagaactccc cagtcgggat cagccccaac agccaaagcg ccccccaaag ccacatccac    1140
cagaggtaag ttccccctcc ccgccccagc tgcctgttgc ctggctgtgg cctgggcagc    1200
acccatagca gctcctatgc ccacagccca gcagcagctg gccttcctag agggccgcaa    1260
```

```
gaagcagctc ctgcaggccg cactgcgagc caagcagaaa aacgacgtgg agggtgccaa    1320
gatgcacctg cgccaagcca agggactgga gcctatgctg gaggcctcgc gcaatgggct    1380
gcctgtggac atcaccaagg tgaaccttct gggcttgtgg gaactgccca ggcacccact    1440
tgtcaggctc ctgcccctta gcagccacgt gaactagaag tgtattagtc aaggtccagc    1500
tgctgtaaca aataggtcct cccaagacaa tggctgaaag gagacagaca tttattatgt    1560
ttcttgcatg taccacccag ggcagtctgg gctctgcaaa tgggaggtcc tccagggcct    1620
gagtttcttc caccttattg ctttgctgca cctgagggg ttgtccttgt ccacatgatc      1680
caagtggatc ctgtcagaag gactagagaa agaggcagag ctagtagtcc cttttaaagg    1740
aagtgacatc actattgctt gtctcccatt ggccagaact aagtaacatg ccacattta     1800
gccacagagg aggctgggac atgtagtctc ttgttggtgc actgtgtgac cagcctgagc    1860
tccattacta gggaagggga ggggatcaga tctggggaga cacttagatt ctgccactta    1920
ggacaggacc attccttttt ctctgagcat cattttctc agagaagtgg ggatggccac     1980
ccctgcctca agaaagaca gccaggattc ctcatgtgat agaatagtac tcataatagg     2040
aaacatttga ggagcttgaa ctgggcgccc agcaaaggcc acccagttta aggaagtgac    2100
atcacttttg cttgcctccc attggcccaa acagtcacat ggctacattt agcctcagag    2160
gagcctggga catgtagtct ttgctggaca ctggagacat ggccttgagc aaaaaaggca    2220
aaaatccaca ctctctctgg acatggtggg tcacacctgt aattccagct acttgggagg    2280
ctgaggtggg aggattcctt gaggccagga gctcgaaact agcctgggaa acacagtgag    2340
actcactgtc atggagtgga tgttctaatt gagagaccac aagaaacaca caaataaata    2400
cagcacctta tcacggccca tgaagactgc accatctgcc ccatcagctc ccttgcctgg    2460
tctcttcctt gttttgttt tgttttgttt tgttttgaga cggagtctcg ccctgtcatc      2520
caggctggaa tgcagtggca cgacctcagc tcactgcaac ctctacctcc caggctcaag    2580
cgattctcct gccttagcct cccgagtagc tggaactaca ggcacacgcc accatgcccg    2640
gctaattttt atatttttag tagagatggg gtttcactat gttggccagg ctgggcttga    2700
actcctgacc tcaggcaatc cacctgcctc gacctcccaa agtgctggga ttacaggcat    2760
gagccactgt gccggcctg ccccttctct ttcacccacc ccctcgctca ctcttcccct     2820
tgctgtctgg tagcctcaaa caccaggcac tctgcaacct cagggccttt gcacatgcag    2880
ttcccactgc ctgaatgctt ttcccacaga cacctgtgtg gttcactttc tcccatcatt    2940
aggtctctgc tcagacatca catctccagg aggcctaccc tgagctgtct aaaatccctc    3000
cctgtcaccc agatccctct gctcctcctc ccagctctgc ctctccctgt ggcatgtatc    3060
accttctact ctctcatatg atttacttat ttccttctgat tattgcccat ctcccccaag    3120
agaatgtcag ccccacgagg gcagggattt tgttctctct tcttcatcct tgtgtcccca    3180
gccccaaagc agagcctagc gcacagtagg ggctccatac atgatttctc aaactcttga    3240
gctcaagcaa tccacccgcc ttagcctccc aaagttctgg gattatagac atgagccact    3300
gcacccggca ccatacatga tttctggggt gactgaagga tgcccttgtt aaatgggaca    3360
atggaaggat caagaagaaa gaacagaggc cgggcatggt ctttcatgcc tgtaatccta    3420
gcaattaagg aggccaaggc cagcggatca cttgaggtca ggagttcgag accagtctgg    3480
ccaacatggt gaaaccctgt ctctactaaa aatacaaaaa ttagccaggt gtggtggcag    3540
gcgcctgtaa ttccagctac tcaggaggct gaggcaggag aatcacttga                3590
```

<210> SEQ ID NO 110
<211> LENGTH: 37700
<212> TYPE: DNA
<213> ORGANISM: Homo sapiens
<220> FEATURE:
<221> NAME/KEY: misc_feature
<223> OTHER INFORMATION: the genomic sequence set forth by nucleotides
      13864993-13902692 of GenBank Accession No. NC_000019.8

<400> SEQUENCE: 110

| | | | | | |
|---|---|---|---|---|---|
| gacggaggag | ccggcaggga | gatcctgttt | cctcatcagg | ggagctatgt | aggaaaagat | 60 |
| aaaactgaag | gagatctgcc | cgggtgcggt | ggctcacacc | tgtaattgca | gcactttggg | 120 |
| cggctgaggc | gggcagatca | ccgaggccag | gagttcgaga | ccaacctggg | aacatggtg | 180 |
| aaaccgtatc | tctactaaaa | atacaaaaat | tagctggatg | tggtggcgca | cgcctgtaat | 240 |
| cccagctact | tgggaggctg | aggcagaatg | gcttgaactc | aggagatggt | gtttgcagtg | 300 |
| agccaagatt | gtgctactgc | attccagcct | aggtgagaga | acaaggttct | gtgtcaaaaa | 360 |
| caaacaaacg | aggggatct | gaaatcctcc | taggttgtca | ctcacctatc | gagacaaacg | 420 |
| caaaacaaaa | tccaacagga | aaccagtgct | aagagtctcc | taggctgggc | gtggtggctc | 480 |
| atccctttaa | tcccagcact | gtgggaagct | gaggtgggtg | gatgcccagg | agtttgagac | 540 |
| cagcctgagc | aacatagtga | dacccctttt | ctacaaaaaa | tttaaaaatt | agctggacgt | 600 |
| ggtgatgtgt | gcctgtggcc | ccagctactt | gagaggctga | aatgtcacga | tcatctgagc | 660 |
| caggggagtt | caggctgcaa | tgagctatga | tcacgccact | gcactccagc | ctgggtgaca | 720 |
| gagcaagacc | ctatctcaaa | aaaaaaaaaa | tgtctgctag | atggaaggcc | ctggaaaacc | 780 |
| tgctttgaaa | gagtgggatg | gggatggaga | agcagtgacc | tgagaacatt | taactgtcaa | 840 |
| ggagggtgca | gagtcccacc | tggagaatac | actgccttaa | caggtgactt | tgttacattt | 900 |
| ataatcccag | gaattgcctt | ctgaactggg | aatagggata | ttctcatttg | gacggacact | 960 |
| ccagccctga | cacggcacat | tctagggaaa | ggaaattgtg | gatgcaagaa | acatagtgtc | 1020 |
| tttaaaaact | agtgaaactt | agggttatat | ttaaataaat | aagggccagg | cgtggtggct | 1080 |
| cacgcctgta | atcccagcac | tttgggaggc | cgaggcgggc | ggatcacctt | aagtcaggag | 1140 |
| ttcgagacca | gcctggccaa | catggtgaaa | ccccgtctct | actaaaaata | caaaaattag | 1200 |
| ttgggtgtgg | tggcgggcgc | ctttcatccc | agctactcag | gaggctgagg | caggagaatc | 1260 |
| gcttgaaccc | gggaggtgga | ggttgcagtg | agccgagatt | gtgccactgc | actccagcct | 1320 |
| gggtgacaga | gaaagaccct | gtctcaaata | aataaataaa | taataagga | tatgtatatc | 1380 |
| gttttgtttt | ggctaattat | tttatttctt | gtagatatgg | ggtcatcctt | gttatgttac | 1440 |
| acaggctcct | cttgaactcc | tgggctcaag | cgatcctctt | gcctcagcct | cccagtgtgc | 1500 |
| tgggattata | ggcatgagcc | actgcactca | gccctgattg | cttttctttt | tttattggtc | 1560 |
| gttagctcac | ataacaacaa | ttcctttgtt | cccttcttga | ttaaggaaga | ggaggaatgt | 1620 |
| ggaagaagga | tgggtttgac | cagcagacag | aatatgagtt | ctgtaaccct | gaaaaatgca | 1680 |
| atgttatctt | tgcccacagt | taaaactttt | ttttcttttt | ttagatggag | tctcgctgtt | 1740 |
| gcccaggctg | gagcgtagtg | gcatgatctc | agcttactgc | aacctctgcc | tcctgggttc | 1800 |
| agtcgattct | cctgccttag | cctcctgagt | atctgggatt | acaggtgcgc | caccacaccc | 1860 |
| agctaatttt | tgtattttta | gtagagacgg | ggttttgcag | tgttggccag | tcttgtctca | 1920 |
| aactcgtgac | ctcaagtgat | cttccccct | cggcctccca | aagtgttggg | attacaggca | 1980 |
| ttagccacca | tgcccggcta | aaacatcaac | ccttcttacc | agcgaggaaa | gctaggagaa | 2040 |

```
gcgagatccg agggccctga gctctgggag ggagtgggtc acagcactag ataggttgtg    2100
ggtctctttc ccaaagcatt gctgtctgct gagctgctgt gctatgtgga ctgtcagtgg    2160
ggagacctgc cggaatgttc agagccacct acctggagac ggcctttcct ggttcctccc    2220
cgtgctgctg tgtagaggga acaggtccca atttgccctc tggctcctca gggtgatgta    2280
aacagcccaa catggaactc tgggggtccc catagaagtc tcctagcctt gggttcttta    2340
ggggttttgg aggacagagt ccctctcctg ttttagagac agaggaagat gaaggggtgg    2400
gggatacagc cactgctcat ggctgacaac tcaggtctcc cccactacaa ccaggctgca    2460
cgcgagaagg ggccgaatcc atttcactct ctgcggggtc ccaagtgcct gtaagagcat    2520
cttgtacact gttggtgctc aataaataaa ttatccatga ctggataaat gcacaccacc    2580
aagggcagac aagactaaat tatgtaccat tctaatgtgc tgagacatct gcaaaatagc    2640
catcctggga aaactgggac tcacagccac cgggtgctga agaggtgatg ctttggccac    2700
gtcctggccc cttgcatttc tgcactaact tccccatcac tgaaagcaat tgcgatgtgt    2760
cttcttctgg catttaagag gctaaagatg cttattgaca tctttgtata tatagcgcag    2820
tggctcacgc ctataatccc agcactttgg gaggccgagg cgggtggatc acctaaggtc    2880
aggagttcaa gaccagcctg gccaacatgg caaaaccccg tctctactga aaatacaaaa    2940
attagccggg catggtggca cccacctata gtcccagcta cttgggaggc tgaggcagga    3000
gaatcgcttg aacctggtag gcggaagttg cagtgagctg agattgcgct actgcactcc    3060
agcctggttg acagagcgag actctgtctc aaaaaaaaat taatatatat tatatatcat    3120 ataaaaata catacatatt catatttaat atatacatac ataaaaata taattata    3180 atgtatttac atattgcata tttataatta taaaatatat tatttaaatt atatatttat    3240
gatatattaa tatattataa acattatatc cttgtattat attatatatt tatatatgat    3300
atatatttat taaatatata ctatatatat tatatatccc attatattgc caggttgttc    3360
catgtgatct aaagccaggc cacgccacct caggattcag cctcagccaa atatgtaaat    3420
atatatattt atacatatgt atttatacat acatatgtat ttatacatac gtatttacat    3480
atatgtattt atgtattata tatactatat atatatttt tctttttta agacagggtc    3540 tggctttgtc tcccaggcta gagtgaggtg gtgcaactgt ggatcactgc agtcttgacc    3600
tcataggctc aagccatcct cccacctcag gccactcaag tagctgggac aaaaggtgtg    3660
tgccaccatg cctggctaag ttttctttg cttttgtttt gttgagacag ggtctcatat    3720
gttgcccagg ctggtcgtga actctggcgc tcaagtgatc ctcttgtctc ggcctcccaa    3780
agtgctggaa ttacaggcat gaaccacttt gcctcgccag aatctatctt ttgaattaag    3840
aaaactccct tacatcgaaa ctttttttt tttttttga acagagtct cgctctgtca    3900 ccaggctgga gtgcaatggc acgatctctg ctcaccgcaa cctctgcctc ccgggttcaa    3960
gtgattctcc tgcctcagcc tcctgagtag ctgagaccaa ggcacgcac caccacccc    4020 agctaatttt tgtattttta gtagagacag ggtttcacca tgttggccag gatggtctcg    4080
atctcttgac ctcatgatcc gcccgcctcg gcctcccaaa gtgctgggat tacagacatg    4140
agccaccgtg cccagccaca tcaaaacttt caatagtggc tggcttgtaa gacttcccca    4200
agcctggccc caacctaatc atgcattcag tgaacaaatg ataagggttg actcagtga    4260 gttccacacc agatgctgtc ctaagaactt gtgtgtgtta agataaaagc tcaaggcagg    4320
gtgctgctgt tatgcctgcc ttacagaagt accttgagca attcaatatt atctttgtcc    4380
atgattaaaa tattggcctt tgccaccagc aaggaaagat gccagcctgt aatcccagga    4440
```

```
ctttgggagg ccgaggcagg tggattgctt aagctcagca gttcaagacc agcctgggca    4500
acatggcgaa accctgtcta aaaagtacga aaattagcca acatggtgg tgcatgcctg     4560 cagtcccaca tacttgggag gctgaagggg gaggatgact tgagcccaga ggaagagatt    4620
gcaatgagtc cagactgtgc cactgcactc cagcctgggc aacagaacta gagcctgtct    4680
caaaaaaaca tttaaattaa acatttaaat taaaataaat aaataaaagg gcaatatggc    4740 aaaacccat ctctactaaa aatgcaaaag ttagctgggc atggtggtgg gcacctgtaa     4800
tcccagctac ttgggaggct gaggcaggag aatcgcttga atccgggggg ctgaggttgc    4860
aatgagccaa gatggcgcca ctgcactcca gcctgggcaa gggagtgaga ttccatctca    4920
aaaaaataaa taattaaatt aaattaaaag gaaaggaaag atgcgagaat tgacacccaa    4980
gggccccaag ttcccagaga ggtgaaaacg ttaaggcaca cagaggccca ggaaccaagg    5040
ctggcacccc gtccaactcc agaaccagca cacttaagaa tacttgagca tttactgaat    5100
gcctactatg tagtagattt ctgccaaggc aggcagaaca aaaagacaaa ccaacagcca    5160
ggtgtggtgg tgcacacctg cagtcccagc tactcaggag gctgagggg taggatcact     5220 tgagtccagg atctcacttg ggtaacacag tgagatccca cctctataaa acatttaaaa    5280
attagctgag ggtggtggca tgcacctgta gtctcagcta ctcaggaggc tgaggcagga    5340
ggattgcttg agccctggag gttgaagctg cagcaagccg tgattgtgcc actgcactct    5400
ggcctcagca acagagctag atcctatctc taaaaaaaac actaaagaat aacactatcc    5460
aggaccaggc gcagtggttc atgcctgtaa tcccagcact ttgggaggct gaggcgggcg    5520
gatcccctga ggtcgggagt ttaagaccag cctgaccaac atggagaaac cctgtctcta    5580
ctaaaaatac aaaattagcc gggcatggtg gctcatgcct gtaatctcag ctactcagga    5640
ggctgaggca ggagaatcgc ttgaacccgg gaggcggagg ttgcagtgag ccgatatcgc    5700
gtcattgcac tccagcctgg gcaacaagag tgaaactcca tctcaaaaaa aaaaaaaaaa    5760
aaaaaagaat aacactatcc aaacccccaga tggactcttt ccaacctcag ctctacatta    5820
cacacttaca catcgtgaag taaacctact gaatgagtct ctctttcctc gacgccaatt    5880
gctagggtct gcatcagtcc ccattcagct gtttgccctc cactaaacca cagcaatctt    5940
cctgtaattg cttctaattc ttcttcttct tcttttttt tttttttgag atggactctc      6000
gctctgttgc ccaggctaga gtacagtggc atgatctcag ctcactgtaa cctctgcctc    6060
ctgggttcaa gcaattctcc tgcctcagcc tcctgattgg ctgcgactac aggtgcaagc    6120
caccatgcct ggttaatttt tttgtatttt cagtagagac gggttttcac cacgttggcc    6180
acactggttt tgaactcctg atctcaagtg atctgtctgc cttggcctcc caaagtgctg    6240
ggaatgcagg tgtgagccat ggcgcacggt aagttgcttg taattctgtc agttacagtt    6300
cgggagtgcc cgtttagaac tttatcccac tgctgtgtat ttgcttagct ctcgctgaga    6360
gaagcatttt cctttgtcct ctgactacag ctggaggatc tccagggcag gaactgagtg    6420
caatgcaccc tttgatctcc ccttcgccct gccctgcccc atcaggtgcc cacctcaaag    6480
gatgtaccac cacaagtaaa gctccgatgg acattgctta tagaaacaca ttcctaaccg    6540
tccgggtgca gtggctcatg cctgtaatct caccacgttg agaggtgag gtgggcagat     6600 tgcttgaggt caggagttca agaccagcct ggccaacatg tgaaaccct gtctctacta     6660 caaatacaaa aaattagcca ggtgtggtgg tgggcacctg tagtcccagc taatcaggag    6720
gctgaggcag gagaatcact tgaacccagg cggcggaggt tgcagtaagc caagactgca    6780
```

```
ccactgcact ccagcctggg tgacagagca agactctgtc tcaaaagaaa cacgaccttg    6840
tggtctgcca gaaaagacaa aatatagctg ctttgtttat ttggtttctt gagattctca    6900
aacacttgct cacttggctg actgaatggc catttgtacc aaataaaaag caaaaaaata    6960
tcaatggcat tgaagagtct tctctttcct tcctgtgatc tgtccacatg ggactaattt    7020
aagaaaaaat aaggcagaac cttgtgttcg acaccaaaga ctaaagacat tgggagggaa    7080
aaggcctctt tcaccacctg ccagaatttt cttcctctct ctccacccett ccagcacaca    7140 cagaaagggt tgtccagggc cagcccagag gtccactgag ctggggagtc taccgccaac    7200
agaggcccca agtgacctgc tgtgggtgga cctggctgtc cccagcttcc ccctccaagg    7260
tcagagaaat tctgatgcct ccaagcagcc tgttgctcat ctctgcacaa aacatgttca    7320
atctgctgat catttcctct cctgtcccat atcttggggg aaaaaacatg cacaccattc    7380
cctaaattca tcagccacta aattaaaaag tcatttcaaa attttgaaga aatttaactt    7440
actttagaaa atgataggca aatggaactc tactacatca tattgggagt ttgtcttttct   7500 gacttggttt gttccttttt ttttttagac agagtctcac tctgtcgccc aggctggagt    7560
gcagtggtgc aatctcagct ctcctgggct caagcgagtc tcgtgtctca gcctcccaag    7620
tagctgggat tacagacaca tgccaccatg cccggctaat ttttgtgttt ttagtacaga    7680
tggggtttca ccatgttgac caggttggtc tcgaaccctg acctcaaatg atccatccac    7740
ctgcctcggc ctcccaaagt gctcagatta caggcatgag ccatcgtgcc caacaatctt    7800 tcttttttttc taagagacag ggttttgttc tgtggcccag gctggagtgc aggcgcaatc    7860
atagctcact gcagcctgga actcctcagc tcaagccatc ctcctgcctc aatctcccaa    7920
gtagccagga ctacaggtag gcaccaccac actggttaat taaaattttt tttttttttt    7980
agagactggg taacattatg ttgctcaggc tggtcatgaa ctcctggtct caggcaatcc    8040
tttcacctcg gcctcccaag tagcctggag tacaggtgcg taccaccaag cctggctatt    8100
ttggggtgtt tttcttttca aatgatgaaa ttgtataggt atgttgacaa gtaaacatgg    8160
tcatgatcta ccacaaagtg aaaaatggag gttgcagatc agtaagtgtg atgattcgat    8220
tttccaataa aaacatttta tctgggccag gcacggtggc tcatgcctgt aatctttggg    8280
aggctgaggc aggcggataa cttgaagtca ggagttagag agcagcctag ccaacatggt    8340
gaaaccccgt ctctactaaa aatgcaaaaa tttgccaggc atggtggcag gtacctgtaa    8400
tcccagctac tcaggaggct gaggcatgag catcacttga acccaggagg cagaggttac    8460
agtgaaccaa atcgtgcca ctgcactcca gcctgggtga cagagtgaga ctgtctccaa     8520
aaaaaaaaaa aagaaaaaag ctcaacactg tatctgtata tatacagaaa aagtctgacc    8580
aggcatggtg gctcatgcct gtaattctga gcacattggg aggccaaggc aggtggactg    8640
ctggagccca gaagttcaag accagcctgg gcaacatagt gaggcctcgt ctcttccaaa    8700
aaatacaaaa attagccagt catggtgcca cacacctgta gtcccagcta ttccggaggc    8760
tgaggtggga agatcacctg agcctgggga ggtcgaggct gcagcgagct atgattgtgc    8820
cactgctctc cagcctgggc gacaaagcaa gactctgtct cgaaaaaaag aaaaaaaaaa    8880
aagctgggta tggtggctca ctccagtaat cccagcactt tggctgaggc gggcagatca    8940
tgtgaggcca ggagttcaag atcagcctgg gcaacatggt gaaacccccat ctctactaca   9000 aatacaaaaa ttatctgagc gtggtggcag acacctgtaa tcccagctac tcaggaggct    9060
gatgcaagag aatcgcttga aaccaggagg cggaggctgc agtgagtcaa gatcgtgcca    9120
ctgcactcca gtctgggcaa cagagtgaga catcatctta aaaaaaagtc tgagctgggc    9180
```

```
gcgctggctc atgcctgtaa tcccagcact ttgggaggcc gagatgggcg gatcacctga   9240
ggttgggagt tcgagaccag cctgaccaac atggagaaac cccatctcta ctaaaaatac   9300
aaaaaaatta gctgggcatg gtggcatatg cctgtaatct cagttacttg ggaggctgag   9360
gcaggagaat tgcttgaatc taggaggcag aggttgcggt gagccgagat cgcgccagcc   9420
tgggcaacaa gatcaagact ctgtctcaaa acaaaaaca aaaagtctg ggctgggcgc    9480
ggtggcctac tcctgtatcc ccagcacttt gggacaccaa gacgggcaga tcacctgagg   9540
ttgggagttc aagaccagcc tgaccaaacc ctgactctac taaaaaaata caaaaattag   9600
ctcagcatgg tggtgggtgc ctgtaatccc agctacttgg gaggctgagg caggagaatc   9660
gcctgaactt gggaggtgga ggttgcagta agccgagatc gcgccactgc actccagcct   9720
gggcaacaag agcgaaactc cgtctcaaaa aaaaaaaaa aagtctagaa gcagtgtacc   9780
gaggttagag tcctgtcctg tttttcatgc tgttctacag ttgatcactg tcctatggct   9840
atgctagatg tcaacattag ggaaagcttg gagaagggta gctagaactc tctgaattat   9900
ttttgcaact tttctttaag tcccagatta cttcaaaata aaagttttct taaaagtctg   9960
gaagaagaat tgttaacagc agtgtacatt tgtgtactac cttaggtcag ttctgggtgc  10020
tttacagata ctaatccaca tgtgagctct aagggcagga ttcttcacct tggaggacat  10080
ttggggctgg atcattctct gtggctgggg ggcatcctat gcatggtagg atatttgagc  10140
agcatccctg gcctccaccc actagatgtc agtataattt ccccagttat gaaaaccaaa  10200
aaaagtctct aggccgggca cggtggctcc cacctgtaat cccagcactt gggaggctg   10260
aggcaggcag atcacctgag gtcaggagtt tgagaccagc ctggccaaca ttgtgaaacc  10320
ctatccctac taaaaataca aaaattaggc gggcgtggtg gtgcacatct gtagtcccag  10380
ctacttagga ggctgaggct gcagaatcgc ttgaacccag gaggtggagg ctgcagtgag  10440
ccaagatctt gctactgcac tccagcctgg acgacagagt cagacttggt ctccaaaaaa  10500
aaaaaaata aagtctccaa acattgccag ctgtctctgg aggtcaaaat cccttcctct  10560
cacctagtta agaaacactg ctctaaagga aagggtagtg gcttttatta tccccaattt  10620
acaaaagggg aaactgtggc acagaggaaa tcatccacca ccacacactg agcagaactg  10680
ggatgaaccc aggttttggg ccccagagta aaacactcag ccacataccg agtgccttg  10740
tagtacatca agcattattc caggggtcat ctctgggact ggttccgcag ggaggctgtc  10800
ccgctgccct gaagcccggg gaggcctcct ctaagctgtg ggaccccacc agaggcttgc  10860
agaagctcca gaaaactttc acttttactt ttcctgtatg ccctctccgt tatttctatt  10920
tttctttctt tcttttttt tttgagacag ggcctcaatc tatcagtcag gatggagtgc  10980
agtggtacga tctggattca ctgcaacctc cacctcccag ttcaagcaat cttcctgcct  11040
caacctcctg agtagctggg actacaggtg cctgccacca cgcccagcta atttccttac  11100
tttacattgt agagacagga tctcgctatg ttgcccaggc tggtcttgaa ctcctggact  11160
caagcgatcc gccacctcg gcctcccaaa gtgctaggat tacaggcgtg agccaccaca  11220
ccggccttct atttttctta ccagcatgaa ttaaatcctt tttgtctttt tcttttttt   11280
gagacagagt cttgctctgt tgcccaggct agagtgcagt ggcaccatct ggctcactg   11340
caacatcgga ctcccaggtt caaacgattc tcctgcctca gtctcccgag taggtgggac  11400
tacaggcatg tgccacaaca cctggctaat ttttgtattt ttagtagaga cggggtttca  11460
ccatgttggt caggctggtc ttgaactcct gaccttgtga tctgcccgcc tcggcctccc  11520
```

```
aaagtgctga gattacaggt gtgagccacc gcacccggcc aatccttgct tcctttttaag   11580 gaggttaagg cagtcgtgtt agccagatct gcaataaaca agcccacatt cttcccacaa   11640
gcagaagcag aaatcaacaa gtgtccattt gaatgaacgt acctgaggtc cgcagcttct   11700
tcctcttagt cattttatct tccccttgag aaatctgaaa acaagcaaaa tctctcatca   11760
ttataagcag tctctgtctc tgtttatatc cagtggcttt ggctgagagc agaggttacc   11820
cctacctcca cctcagccca tttggctgcc ccaggggtca gatggctccc actgggacac   11880
aggatgggac acagagtcac agccactttg ggccatggcc aggtaggaat tcaaacctcc   11940
tccaaactga agatcttatg cccaggacct gaaagacaaa tgggccctgg ggggtcctta   12000
tagatagccc cggggaccca gactctggtc cctaggatga acagcctgt gtgaagcccc   12060 tccctccaga ctgggtatc tggggccct tccaaggaca cttgaggact ctccagggc   12120 ctctggagac cagcctggcc aatatggtga acccctct ctattaaaaa cacaaaaatt   12180
agcctgggca tcgtgacgca cacctgtaat cccagctact tgggaggctg agacagtaga   12240
attccttgaa cccatgaggc agaggttgca gtgagccgag atcgctctac tgcactccag   12300
cctgggcgac agagcgagac tccgtctcaa aaaaaaaaa aaaaattagt caggtgcggt   12360
ggcacacacc cgtaatccca gctactcagg aggctgtggt acaaggccag gaggcagagg   12420
ttgcaatgag ccaagatcgt gccacttaa aggggacagc tgggtccttg gaggggaaag   12480
agctgccata ggccggtttc tcccagcctt ggggcgagg caaaccagaa cggacctggg   12540
ccacagaagt cgttgaggac cctctgtcct tatcagaaac gagctctgcc tggatcagtt   12600
gggaataagt cgcttgaatt atccgcgtta ctcttttgg aaaaaataaa tggccaaatt   12660
ggccctcaca gaacgctgga ggcctcgagt ccggaggtga aagatggaaa ggcctgaggg   12720
tgggcgctgt agacccgct cccggtgaca agccccacac tgacactacg ccgaccaccg   12780
agaagtgagg actccacagg ccgagagccc acgtgaagcc ggagcccgtc ggtgactgac   12840
agacgctctg aaccccacag atgtcgccgc ccctcacacc tgcgcgcgct ctgcctcttt   12900
cccgcgcccc gcgaggtccc gccccgcgca tgagcgacgc aaaaccgcc ctcgcagccc   12960 gcgacagtca gcaccgcccc agccaggcgc ctgcgcgccc acgcactacc tgccgggagt   13020
tgtagtttcg gctcggcaga cccggcgagc ccagtggccg cgctccggtg cggcggcgcc   13080
cgaggcccga ggcggaagtg ggacggccaa gcagggaagc gagggctcgg gatcgacggc   13140
cgcggggcgc cgacgaggag tgcaggactc aggaagggcg agtgcgcggc gacagagccc   13200
ggggaaggag gcagggcaag gccgggcttg ggggcaggtg gtccgggcat ccagccttga   13260
agatgcacaa gaggaaagga cccccgggac ccccgggcag aggcgccgcg gccgcccgcc   13320
aggtgagttt gcgccccacg gcccgacctg gggatccctc ccacccccg tcactcgctc   13380 agggaagggc ccacccccc agggaagccc gatctccgcc ccacaggtaa gccccggtcc   13440
ccgcctcccc ccaggtgagg ctccaacacc acccaagtgt ggcctactgg ccttggctcc   13500
ccagctcctg ggccctgcc ccgggttcgg ggccacctgt tgccacagct gctccagtcg   13560 aggagggca gtcctcggac ttgacacatc aaacccttgc atcagtcggg ccatgtcaga   13620
ctctttttat tccattgtac agatgaggac tttgagactc agagacgtga agacatctgc   13680
ccaaggtcat agggattaac agcttggcca gggctaagca caaatccagg gctgcagcca   13740
taagcttatg gcactgtggc tggacccctt ctcactctcc cgacttcttt gccccaggca   13800
ccagatagtt tgattttct cagtttgat ggaaggagcc caggacatag cttggtgttc   13860
agatattaga gtctggctga cctgaagttc cctcctggcc tctgtacatc ggacacttga   13920
```

-continued

```
ctttacagct ctgagcctca gctttctcat ctgtaaaatg gagatctcta taatcccagc   13980
acttcaggag atggaggcgg aggcagaggt gggagagtca tttgaggcca gagtttgaga   14040
ccagcctggg caaaagcaag accccgtct cgacaaaaaa agactaactg ggcatggtgg    14100
catgtgcctg tagtactact acttgggagg ctaagaaggg aggattgctt gagcccagga   14160
gttcaagacc gcagtgagct atgattgcgc tacttctgct ccagcctggg tgacagaaca   14220
agactctttc tctaaaataa agataaaaaa ttaaaaatgg aagtccgggg tggtgtctca   14280
cacctgtaat cccagcactt tgggaggcca tggcgaaacc ccatctctac taaaaataca   14340
aaaattagct gggcatggtg gcgggcacct gtaatcccag ctactcggga ggctgaggtg   14400
ggagaatcgc ttgaaccgag aggcggaggt tgcagtgagc tgagatcgcg ccactgcatt   14460
ccagactggg tgacagagca aggctccttc tcaaaataaa taaataaatt ccttctgaaa   14520
ataaataaat aaataaaaaa ttaaaaatgg agacctccaa gagacctac attacaggac    14580
agttgtagag agtcattgag atagtttatg gaaagtgcta gaacatagca ctcaataaat   14640
gttactatta tcattattac tagttggtgg aaccatacat aattgccaat atttggccat   14700
ttttttaccta caggaaaggc aatttcatat ggttaaacac gatgttatca catcatgatt   14760
ggtcattagc caagatagga agacgggtct gcatggcaaa cctgcattgt ggttaggggt   14820
tcttttttg tttgtttgtt tttgagacag agtcttgctc tctcgcccca ggctggagtg    14880
cagtggcgca atctcggccc actgcaacct ccgcttccg ggttcaagcg attctcctgc    14940
ctcagcctcc cgagtagctg ggattacagg catgcgccac catgcctggt taattttgta   15000
tttttagta gagacggggt ttctccctgt tggtcaggct ggtctgtctc gaactcccca    15060
tctcaggtga cccgcctgcc tcggcctccc aaagtgctgg ggtacaggc gtgagccacc    15120
gtgcccggcc taattttgt attttagta gtgatgggat ttcaccatgt tggccaggct     15180
agtctcgaac tgctgacctc aggtgatccc cccaccttgg tctcccaaag tgctgggatt   15240
acaagcgtga gccactgcac ctggccctgt cgtcagggct tctaattgct cttctttttt   15300
ttttggagac agagtcttgc tctgttgccc aggctggagt tggtggcgc aatctcagct    15360
cactgcaacc tccacctccc aggttcaagc aattctcctg cctcagcctc ccgagtagct   15420
gggattgcag acaccgccag cactcccagc taattttgt attttagta gagacgggt     15480
ttcaccatgt tggctaggct ggtctcgaac tcctggatta caggcgtgag ccaccgcatg   15540
cagccatcat gctcttgaag cccaaccttc ccacacagcc cctctgctga ggatgctgga   15600
aagaaaagcc caagtgtaca gagtagcttt gctttgggca aagtgtggag cctgcttcct   15660
tccctccttc cctccctccc tcgcttcctt cttttttttcc ttccttccct ccttcctccc   15720
tccctctctc cctccccggc tccatctctc tttctttctt tcctttcaac agggctttac   15780
tctgttgccc aggcggagtg ccgtagcaca gtcatggctc actgcagcct tgatctcccc   15840
aggctcaagt gatcctcctg cctcagcctc ccgagtagct gggaccacag gcacacagca   15900
caactcccag ctaattttaa aaagttttt ttcctgtaat cccagcactt tgggaggccg    15960
aggcgggcag atcatgaggt caggagatcg agaccatcct ggctaacaag gtgaaacccc   16020
gtctctgcta aaaatacaaa aaaaaatta gccgggcgtg gtggcgggcg cctgtagtcc    16080
cagctactcg ggatgttgag gcaggagaat ggcatgaacc ccgaggcgg aggttgcagt    16140
gagctgagac tgcaccactg cactccagcc tgggtgacag agcgagactc tgtgtcaaaa   16200
aaaaacaaaa aacaaaaaac tttttttttt tttgtagagt tgggggtctc actgtattgc   16260
```

```
ccaggctggt ctggaactcc cagacacaag ccatcctctt gccttggcct cccaaagtgc    16320
tgggatgaca ggcgtgagcc actgcgccca gccaggggcc tgcttttccc actgaacttg    16380
gcccagcagc acatcataag tgtggattca gatcagagag ctgggtctct tgcccttttgc   16440 cccaggttga actgtgccag agggcctggc ctatcttgga acacctgttc tgggcttgtt    16500
ccagcctcct ggcactcccc agggaaatgg cttttccctgg gagaccttgt ttccttcctc   16560 ccaagggggac tctctggcca tcatggctgc ctctagccat gtggtgaacc aaaggtctga   16620
ctgaaccctt gctgttcccc tagctgggcc tgctggttga cctctcccca gatggcctga   16680
tgatccctga ggacggggct aacgatgaag aactggaggc tgagttcttg gctttggtcg    16740
ggggccagcc cccagccctg gagaagctca aggcaaagg tgagatggtt aacacaccct    16800
cagaacattt tctgatctcc tgcaagtggt tcgggcgcag aactgggggc actgggtagg    16860
taggggaaag aagacagaga agaccctgt tctcctggag ccaatgatct gggtaagaga    16920
gtcaagatcg actctgaggc cgggcacggt ggctcacgcc tgtaatccca gcactttggg    16980
aggccgaggc aggcagatca tgaggtcagg agattgagac catcccggct aacacggtga    17040
aactctgtct ctactaaaaa tacaaaaaaa aaaaaaaaat tagccgggcg tggtggcggg    17100
cgcctgtagt cccagctact caggaggctg aggcagaaga atggcgtgaa ccaggaggc    17160 ggagcttgca gtgagccgag atcgcaccac tgcgctacag cctgggcgac agagcaagac    17220
tccgtctcaa aaaaaaaaa aaaaaaaaa agatcaagtc tggaccgaga ctgagagttg     17280
gaatccgagc tctgccactt actggttatg tgacttgatg agtcacatca tgtgctttgg    17340
cctcagtttc accatctgta aaactggaat aataaccatg ttataggagt taatctggag    17400
tccataagta tttcacccag ggcccccctca cacacaataa gctcatgtca gccaggcaca   17460
ttggctcatg catgtaatcc cagcactctg ggaggccaag gtggacagat cacttgggggc   17520 caggagttcg agaccagcct ggccaacatg gtgaaaccct gtctttacta aaaatacaaa   17580
aattagccaa gcttggtggc gaacacctgt aatcccagct acttgggggag ctgaggcatg   17640 agaatcgctt gaatccagga ggcagcagtt gcagtgggca gagattgcgc cactgcactc    17700
cagcctgggt gacagagcaa gatcctgttt ccaaaaaaca aaaagagag aagcttcatt     17760 caggcatgaa ctactgtgct gttggctgtg aattcaaagt taatgaatga acgatatcta    17820
ttcaggaagg tgtcttcaaa cagaaacaca catagagcaa ggttgtgtat tgatcagttg    17880
attaaaattt tgtgaccaga gctgggtgtg gtggtgcatg cctgtaatcc cagctactcg    17940
ggaggctgag gcaggaagat cacttgaggc caagagtttg aggctgcagt gagctctgat    18000
tgggccactg cactccagcc tgggtgacag agcaagatcc tgtctccaaa aaaggttatg    18060
actggagatt cacaggaacc taagcttaaa tttcccctag gagcaacagt cttatagtca    18120
ttaatttagt cttcaaagca gctttatagaa atgtaacata actaataaca agatattggc    18180
aatatgctat tctaagagct tcattgacct tctctgctcc aacctaccta tgaaggagga    18240
actgttgtca tccccgtgtc acagagggag aaactgaggc tcagagaggt gacatcactt    18300
gccgaagttc tcacagagag aaagttgcag agctgggggtt ttttttgttg ttgttgtgtg    18360
tgtgtgtttt ttttttttt tttggagaca aacccttgct ctgttgccca ggctgcagtg    18420
cagtggcgca atctcagctc actgcgacct ctgcctcctg ggcttaagtg attctcctgc    18480
ctcagcctct ttagcagcgg ggattacacg ccaccatgcc cagctaattt tttttttttt    18540
tttttttttt ttttgagacg gagtctcgct ctgtcgccca ggctggagta cagtggcgcg    18600
atcttggctc accgcaagct ccgcctccta ggttcacgcc attccccctgc ctcaggctcc    18660
```

```
cgagtagctg ggaccacagg cgcccgccag catgcctggc taatttttg tatttgtagt   18720 agagacgggg tttcaccgtg ttagccagga tggtctcgat ctcctgacct tgtgatccac   18780
ccgcctcggc ctcccaaagt gctggggtta caggcgtgag ccactgcgcc cagcctaatt   18840
tttgtatttt tagtagagac agggtttcac catgttggcc aggctggtct tgaacgcctg   18900
acttcaagtg atccttctgc ctcggcctcc caaagtgctg ggattatagg cgtgagtcac   18960
tgtgcccggt ctgcagagct gggttttgaa ttcaggtagc caggccccag acctgaggct   19020
gaataaggaa gagatgaaat ggggaagtca gcgagaagtg ggatcaccta gcgtgtccag   19080
gatgggaaat gggggctctt ggtgtacgac cctggtccac ctggggcatc ccctaccgc   19140 caggtccctt gccgatggag gccattgaga agatggccag cctgtgcatg agagacccgg   19200
atgaggatga ggaggagggg acggatgagg acgacttgga ggctgatgat gacctgctgg   19260
tgagcactga gggcggggtg ggggctctga tccggttgcc cccatccagc aggcccttat   19320
atcctgccct ggctgtgtgt ccctgcaggc ggagctaaat gaggtccttg agaggagca   19380 gaaggcttca gagccccac ctcctgtggc ccaggtacag tttggatgac tccactccct   19440
tgaaccacaa cccaacggac agcccggggt tcaagaccta gcctttttta tgagatggag   19500
tcttgctgtg tcacccaggc tggagtgcag tggtgccatc tcagctcact acaacctctg   19560
cctcccaggt tcaagggatc ctcccacctc agcctcccca gtagctggga ttacaggtgt   19620
gtgccaccac gcctggctaa tttttgtatt ttttggtaga gatggtgttt ctctgtgttg   19680
gccaggctgg tcctgacctc aagtgatcca cctgccttgg cctcccaaag tgttgggatt   19740
acaggcgtga gccaccgcgc ctggcccacc cttatccttc acagccatgt gacccatatc   19800
aggtgggtga catgatgctt ctgaaacccc attccctcca ctgggaaatg gggaccatga   19860
tttctgcctc actggggcag gggaggctgg tccaggggatg acatggggcc gactgttact   19920
gcagaagggg ctaacagggg catcccaagt ggggtcacca cccacactgt gcccctgccc   19980
tcccacagcc gaagcctgag gcccctcatc cggggctgga gaccaccttg caggagaggc   20040
tggcgctcta tcagacagca attgaaagcg ccagacaagc tggagacagc gccaagatgc   20100
ggcgctacga tcgggggctt aaagtaagtg ggcagagggc agggtacagg gacccccgc   20160 caacccgat gccctgcacc aagctcttgg cttctcccaa accaatactc acgccttatc   20220
ttagacactg gaaaacctgc tcgcctccat ccgtaagggc aatgccattg acgaagcgga   20280
catcccgccg ccagtggcca taggaaaagg cccggcgtcc acgcctacct acagccctgc   20340
acccacccag ccggccccta gaatcgcgtc agccccagag cccagggtca ccctggaggg   20400
accttctgcc accgcccag cctcatctcc aggcttggct aagccccaga tgccccagg   20460 taggtgatgg gcagggccgg gctgatatgg gatccgagtg ggccatctgg caggatgctg   20520
ctctaggggg gtgccggctg tgcactgatt gtgagatatt ttcaacaccc tgagtcctgg   20580
ggtcttcaag cccctggagt tcatgaatac ctcccaagca ggacatggat acccagagag   20640
ttttttttgt tgttattatg atattatgat aaaatataga tcacatttgc cattaaaaat   20700
tattttagtt ctttttttg agatggagtt tcgttcttgt tgcccaggct ggagcgcagt   20760
ggcacgatct cagctcatta caacctccac ctcccaagtt caagcgattc tcctgcctca   20820
gcctcccaag tagctgggat tacaggcata tgccacactt ggctaatttt gtattttgag   20880
tagagatggg gtttcacctt gttggccagg ctggtcttga attcctgacc tcaggtgatc   20940
cacccacttc ggcctcccaa tttgctggga ttacaggcat gagccactgt gcccggcttt   21000
```

```
ttttaattct tgagacagg gtcttactcc atcacccagg ctggagtgca gtgatgtgat   21060
catagctcag tgtagcctca acctcctggg ctcaagggat cttccctcac cttcaccagt   21120
agctgggact acaggcatgc accacacact tggctaattt ttttttttt tttgagtcgg    21180
agtctcgctc tgtcacccag gctggagtgc agtggtgcga tctcggctca ctgcaacctt   21240
tgcctcctgg gttcaagcaa ttctcctgcc tcagcctcct gagtagctgg cattacaggt   21300
gcatgccacc acacctggct aattttttgt attttagta gagacggggt ttcactgtgt     21360
tagccaggat ggtctcgatc tcctgacctt gtgatctgcc tgcctcggcc tcccaaagtg   21420
ttaggattac aagcatgagc caccacgcca ggcctcatcg cctttttttt tttttttgaaa  21480
cagagtctca ctctattgcc caggctggag tgcagtagca tgatcctagt tcactgcaac   21540
ctgcctccca ggctcaagca atcctcccgc ctcagcctcc tgagtagctg ggattacagg   21600
catatgccac cgtgcccat gcccagctaa tttttgtact ttttgtagag gtgccatgtt    21660
gcccaagcta gaacatatct tctaagaggt ttttcttcct aacctccccc taggaaagga   21720
aggcctccct ccctctcttt gtgatatgaa cacggggctt tgccccaggt ccaaacactt   21780
ccctggcagg aagcaaagag acaactcaaa atactggcat gggtttgaga aagcaaacac   21840
tgggtcacta atccttctg caaccaagct agtttccaag ccattgtttt tgacaaagtt     21900
caaggattac tggaattgtc acctgaaatt gtcaactgaa acgaccaaaa attttttcaca  21960
atggaagttt ggcataaaac ttgtcaggag ttcaaagaat acaaagacat cacagtaaca   22020
aaattctgtg tcttccaatc tatttgttaa tgtgaagtag gtttctcaat actttaattt    22080
ttttgagacg gagtctcgct cttgtttcca ggctggagtg cgatggcgtg atctcggctc   22140
actgcaacct ccgcctccca ggttcaagtg attcacctgc ctcagcttct cgagtagctg   22200
ggattacaag cgcccaccac caagcccggc taatttttgt attttagta gagacggggt    22260
ttcaccatgt tgctgcccag gctggtctcg aactcctgac ctcaggtgat ccgcctgctc    22320
cgcctcccaa agtgcgggga ttacaggcgt gagccaccac ccctggcctc aacactttaa   22380
aaaagaaaaa aagtgcagat gtagtggctc atgcctgtaa tcccagcact ctgggaggcc   22440
aggagttcaa gagcagtcta ggcaacatag caagaaccca tctctacata aaaattaaga   22500
aattagccgg gtgtggtagt gcatgccttt agtcccagct cctcgagaag ctgaggtggg   22560
aggttcgctt gagtccagga gttcaaggct gcagtgagcc gtgatcgtgc cactccaagt   22620
ctgggcaaca gagcaagatc ttatctctaa aaaagaaaa aacagaagag gattgaatgg     22680
gagaaacgag ttgattgtta gggattggac ccagctccaa ttatgtcagc aagaggtaca   22740
tttctggtag aattttgctc ttggtgtacc aaaactatca aatagctcag caggggctgg   22800
gcgtggtggt tcacacctgt aatcccagca ctttgggaca ccaaagcggg cggatcactt    22860
gaggccagga gttcaagacc agccctggcc aacatggtga gacctcatct ctactaaaaa   22920
tacaaaaatt agctgggcgt ggtggtgcat gctggtagtc ccagccactc gggtggatga   22980
ggcaagagaa tcacttgaac ccagaaggca ggggttgcag tgagccacga tcacaccact   23040
gcactccagt ctgggcgaca gagcaagact ctgtctcaac aaacaaacca acccaaaaag   23100
ctcagctggg tgtggtggct cacacctata attccagcac tctgggaggc caaggtggga   23160
ggatcgcttg aacccggag ttcgagatct gtctgggcaa catagggaaa ctgcgtctct    23220
ataaaaaatt aaaaattagc cagccatggt ggtgcatgcc tgtagtccca gctacttggg   23280
aggctgaggg ggagaatca cttgagcctg aaggttgag gctgaagtga gctgtgattg     23340
caccactgca ctccagcctg ggtgacagaa tgagaccctg tctccaaaaa aataaaataa  23400
```

```
aataagcttg atgtatttac gttttgctca attacatgct agtaataatt ataacaataa  23460
ttcaacccgg aaaaacattg ttttaacaa tgaaagattt ataatcacag gaaataaaac  23520
caatacaatg tcaaggtgt gtcacttcta cctccaaaca tattttcagg gaagtaagcc  23580
taagtttaaa gcaatgggtc cagttgttag tctgaaaaaa agatactgcg tgccattttc  23640
tgggtgtttc cagattttgc agacactggg tggtgtcttt attgtactgt gttattttat  23700
actaagaatt gcacttatag ctttaaacat tgaggtactt ccccagaaaa catactgagc  23760
atattatttg aaactgtaac taacacactg tttaaaaagc actgaatact gggtttccta  23820
actttgcaaa cacactgcat aaatatattt tggttgtata aatatacaat agggtaggca  23880
aaaaaggctt tcaaacacac agctatatca tgttagcata aatttctgtg ggggacgtgg  23940
atggaaataa gagaagactc aaaattccca actgcttaaa gtgagtccca ggatatattt  24000
aaaaagtgag ttgggcatgg tggcacatgc ctgtaatctc tgcactttgg gaagctgagg  24060
tgggaggatc acttgagccc aggagtttga gactagcctg gacaacatag taagacccca  24120
tctctacaaa aaaaaataaa aaaccagccg ggcatgcagg tgcatgctct gtagccccag  24180
ctactcagga agctgagatg ggaggatcgc ctaagcccgg tgtctgaggc tatagtgagc  24240
agcagagcaa gactctatct cttaaaaaa aaatacatta aatatggcca ggcacggtaa  24300
ctcacacctg taatcctact tgggaggcc aaggtgagca gatcacttga ggtcaggagt  24360
ttgagaccag cctggccaac atggtgaaac cccgtctcta ctaagaatac aaaaattagc  24420
cagaaattgg gaggcggagg ttgcagtgag ccaagattgt gccactgcac tccagtctgg  24480
gcaacagagc aagacccagt ctcaaaaaat acattaaagc caggcgcggt ggttcacacc  24540
tataatccca gcactttggg agtccaaggt gggcggatca cctgaggtca ggactttgag  24600
accagcctgg ccaacacggc gaaaccctgt ctctactaaa aacataaaaa ttagccgggc  24660
atgtgcctgt aatcccagct actcaggagg ctgaggcagg agaatcactt gaacccagga  24720
ggcggaagtt gcagtgagct gagattgcgc cactgtaccc cagcatgggc aacagagtga  24780
ggctctgtct gaaaaagaaa aaaaaatta aataaataaa taacaaatgg tttacacggt  24840
gaacttggcc caggccctgg aggcttcctg tatgttgttc tcccttccag gtccctgcag  24900
ccctggccct ctggcccagt tgcagagccg ccagcgcgac tacaagctgg ctgccctcca  24960
cgccaagcag cagggagata ccactgctgc cgctagacac ttccgcgtgg ctaaggtgcg  25020
tccagcctga cggacaggac tggagggatg ggcaggatg cttcccacgt ggcctggtgg  25080
caaagcaccc aaatttgcat cctagcttgg tcactcccta gcaatagttt gctgtaagtc  25140
ttggagcctg agtttacccc ctctgtgaaa tgggcacgtg tgttggaaga ggattaagca  25200
agatggcaca aatggaaggg agggagctag aagtcctcgg tggcatggaa gggcccggag  25260
gctccccaca gggtccaagc ccccaactgc acctcttctt ctaatctcct cttccttctc  25320
ccagagcttt gatgctgtct tggaggccct gagccggggt gagcccgtgg acctctcctg  25380
cctgccccct ccacccggtg agaaccctgc catgcccact ctctgggatg gtttcaggca  25440
tacactaagt tctccttgat gctgccaccc ctgttggtca ggcccagaga ccaccctcag  25500
gccagaccag cttgtcgggg gtgcagctaa caagcccctc attggcctgg acctctctgt  25560
ccccagacca gctgcccca gacccaccgt caccaccgtc gcagcctccg accccgcta  25620 cggcgccctc cacaacaggt aggttctggg accctctggg gttgggggca ggctggagcc  25680
agactgtcta cccatccgtt gactcttaac cttgtccccc tgtccggccc agaggtgccc  25740
```

```
ccaccccga  ggaccctgct  ggaggcgctg  gagcagcgga  tggagcggta  ccaggtggcc   25800
gcagcccagg  ccaagagcaa  gggggaccag  cggaaagctc  gaatgcacga  gcgcatcgtc   25860
aaggtgccct  gggggttccg  ggggaggtgg  ggcgagtggg  cagcccggga  gccctcccac   25920
aggcagccct  aacacctgtg  gccctcgcag  caataccaag  atgccatccg  agcccacaag   25980
gctggccgag  ccgtggatgt  cgctgaattg  cccgtgcccc  caggtaggcc  ttgcccctgt   26040
aggcctcgcc  ccagtaggcc  ccgccccgt   aggccccgcc  cccagaggcc  ccgccgctgg   26100
caggctgtgc  cccaagctcc  tgttcctcca  gcctctgagc  cttggcagat  gctattactc   26160
cccatagcac  aggctcaggg  agctgaatac  aacatattca  agggttttgt  aaacttgtta   26220
atcagtggga  gcttgacatt  ggacatgatg  tgtctgcact  gtagaaattg  gcaaaccggc   26280
tggacgaggt  ggtcatgtct  gtaatcccag  cactttggga  ggctgaggtg  ggaaaatcac   26340
ttgaggccag  gagttcaaga  ccagcttggg  caacgtggca  agaccccgtg  gctacaagaa   26400
atttaaaaat  tagcctggtg  tggtggtgca  cacctgcagt  cccactctag  atcatgccac   26460
tgtactccag  cctgggcaac  agagcgagat  cctgtctcaa  aaaaaaaaa   attaattaat   26520 taaaaaagt   aaaggcccaa  gactctatag  gtgggagagg  aatctgcatc  tccaccataa   26580
tggtgtgagt  tggtctccat  cctgacacac  aataaccagg  cctcgactgg  ccacccaggc   26640 ttcccccaa   tccagggcct  ggaggccacc  aagcccaccc  agcagagtct  ggtgggtgtc   26700
ctggagactg  ccatgaagct  ggccaaccag  gatgaaggcc  cagaggatga  agaggatgag   26760
gtgcctaaga  aggtttgagg  gttggggccg  ggcgcagtgg  ctcacacctg  tagtcccagc   26820
actttgggaa  tccaagatgg  gaggatcgct  tgaggccagg  agtttgagac  catcctgggc   26880
cacacagtga  ccccccgtc   tctacaaaaa  aattttttaa  aattagccag  gcatggtggg   26940
actcacctgt  agtccctgct  acttgggaga  ctgaggtggg  aggatcacct  gaactaagga   27000
gttcaaggct  gcagtgagcc  atggtcatgc  cactgtacgc  cagtctgggt  gacagagcaa   27060
gacctcatct  ccaagacaat  taaaaaaaaa  aaaagtgtt   tggtgagaat  tgcttgaacc   27120
gggaggcaga  ggttgcagtg  agccaagatc  gtgctactgc  actccagcct  ggacgataca   27180
gtgatactct  gtctcaaaaa  agaaaaaaaa  aaaaaaaag   gtgtttgggg  ccaggggctt   27240
tgagtgaggc  aggggagtag  caaagtcctg  ggagcccact  aaatgaccac  tgttgtcacc   27300
atcagaccct  gatccttggg  gactggactc  atcacaggcg  ctacgaaatc  tctaacatcc   27360
tctctcttcc  tctacagcag  aacagccctg  tggcccccac  agcccagccc  aaagccccac   27420
cctcaagaac  tccccagtcg  ggatcagccc  caacagccaa  agcgccccc   aaagccacat   27480 ccaccagagg  taagttcccc  ctccccgccc  cagctgcctg  ttgcctggct  gtggcctggg   27540
cagcacccat  agcagctcct  atgcccacag  cccagcagca  gctggccttc  ctagagggcc   27600
gcaagaagca  gctcctgcag  gccgcactgc  gagccaagca  gaaaacgac   gtggagggtg   27660 ccaagatgca  cctgcgccaa  gccaagggac  tggagcctat  gctggaggcc  tcgcgcaatg   27720
ggctgcctgt  ggacatcacc  aaggtgaacc  ttctgggctt  gtgggaactg  cccaggcacc   27780
cacttgtcag  gctcctgccc  cttagcagcc  acgtgaacta  gaagtgtatt  agtcaaggtc   27840
cagctgctgt  aacaaatagg  tcctcccaag  acaatggctg  aaaggagaca  gacatttatt   27900
atgtttcttg  catgtaccac  ccagggcagt  ctgggctctg  caaatgggag  gtcctccagg   27960
gcctgagttt  cttccacctt  attgctttgc  tgcacctgag  ggggttgtcc  ttgtccacat   28020
gatccaagtg  gatcctgtca  gaaggactag  agaaagaggc  agagctagta  gtccctttta   28080
aaggaagtga  catcactatt  gcttgtctcc  cattggccag  aactaagtaa  catggccaca   28140
```

```
tttagccaca gaggaggctg ggacatgtag tctcttgttg gtgcactgtg tgaccagcct   28200
gagctccatt actagggaag gggaggggat cagatctggg gagacactta gattctgcca   28260
cttaggacag gaccattcct tttctctga gcatcatttt tctcagagaa gtggggatgg    28320
ccacccctgc ctcaaagaaa gacagccagg attcctcatg tgatagaata gtactcataa   28380
taggaaacat tgaggagct tgaactgggc gcccagcaaa ggccacccag tttaaggaag    28440
tgacatcact tttgcttgcc tcccattggc ccaaacagtc acatggctac atttagcctc   28500
agaggagcct gggacatgta gtctttgctg gacactggag acatggcctt gagcaaaaaa   28560
ggcaaaaatc cacactctct ctggacatgg tgggtcacac ctgtaattcc agctacttgg   28620
gaggctgagg tgggaggatt ccttgaggcc aggagctcga aactagcctg ggaaacacag   28680
tgagactcac tgtcatggag tggatgttct aattgagaga ccacaagaaa cacacaaata   28740
aatacagcac cttatcacgg cccatgaaga ctgcaccatc tgccccatca gctcccttgc   28800
ctggtctctt tcttgttttt gttttgtttt gttttgtttt gagacggagt ctcgccctgt   28860
catccaggct ggaatgcagt ggcacgacct cagctcactg caacctctac ctcccaggct   28920
caagcgattc tcctgcctta gcctcccgag tagctggaac tacaggcaca cgccaccatg   28980
cccggctaat ttttatattt ttagtagaga tggggtttca ctatgttggc caggctgggc   29040
ttgaactcct gacctcaggc aatccacctg cctcgacctc ccaaagtgct gggattacag   29100
gcatgagcca ctgtgcccgg cctgccccctt ctctttcacc cacccccctcg ctcactcttc   29160
cccttgctgt ctggtagcct caaacaccag gcactctgca acctcagggc ctttgcacat   29220
gcagttccca ctgcctgaat gcttttccca cagacacctg tgtggttcac tttctcccat   29280
cattaggtct ctgctcagac atcacatctc caggaggcct accctgagct gtctaaaatc   29340
cctccctgtc acccagatcc ctctgctcct cctcccagct ctgcctctcc ctgtggcatg   29400
tatcaccttc tactctctca tatgatttac ttatttcttc tgattattgc ccatctcccc   29460
caagagaatg tcagccccac gagggcaggg attttgttct ctcttcttca tccttgtgtc   29520
cccagcccca aagcagagcc tagcgcacag tagggctcc atacatgatt tctcaaactc    29580
ttgagctcaa gcaatccacc cgccttagcc tcccaaagtt ctgggattat agacatgagc   29640
cactgcaccc ggcaccatac atgatttctg gggtgactga aggatgccct tgttaaatgg   29700
gacaatggaa ggatcaagaa gaaagaacag aggccgggca tggtctttca tgcctgtaat   29760
cctagcaatt aaggaggcca aggccagcgg atcacttgag gtcaggagtt cgagaccagt   29820
ctggccaaca tggtgaaacc ctgtctctac taaaaataca aaaattagcc aggtgtggtg   29880
gcaggcgcct gtaattccag ctactcagga ggctgaggca ggagaatcac ttgaacccgg   29940
gaggtggaag ttgcagtgag ctgagatccc gccattgcac tccagcctgg gcaacagagc   30000
gagactccat ctcaaaaaaa aaaaagacc agagaagggt gacagagccg tggtcaggga   30060
atgcccctcg tcaaggaaga atgacatttc tgcagagccc taggtgggcc tgcttgtcct   30120
ccttaccccc gccaccagcc tcgtcctccc caggtgccgc ctgcccctgt caacaaggac   30180
gactttgccc tggtccagcg gcctggcccg ggtctgtctc aggaggccgc ccggcgctat   30240
ggtgaactca ccaagctcat acggcagcag cacgaggtga gggggaggcc cccagcccat   30300
cccccaggag cgtgaccctc cttcccctct cttcccttcc ctcgactcac tgccttctgt   30360
ttccccagat gtgcctgaac cactcaaacc aattcaccca gctgggcaac atcactgaaa   30420
ccaccaagta agtgccctga cctgtgccag acacttgcac ccccagccac ccatccccag   30480
```

-continued

```
ggccagggac atgagcaggg ccctcccacc ggcaggtttg aaaagttggc ggaggactgt    30540
aagcggagca tggacattct gaagcaagcc ttcgtccggg gtctcccacc gcccaccgcc    30600
cgctttgagc aaaggacctt cagcgtcatc aagtaaggct cctgatctac gccccaccac    30660
gtggcccag  tggcccttg  gtggcggtgg ggcgggttgt gctccccaga agctggcaca    30720
agatttacat ctggaagaaa ttttggatag gtggaagagc acagagcatg caaaggctct    30780
ggggcaggca tgagatacaa gtgaaggatg gtgagggtgc agtcacagtg acgcatttgg    30840
gaaagatcta gagagtgcaa aggtgtatct tgtcccaggg cctgggtgag tccacggggg    30900
accagagatg agtcacggct ttggtgggtg ttagtcttgg tactatcaag tcttcccatg    30960
cccagaggag cggggattgt tttctccact ttattttat ttttattttg agacagagtc    31020
tcactctgtt gcccaggctg gagtgcaggg gtgtgatctc tgctcactgc aagctccacc    31080
tcctggattc atgccattct cctgcctcag cctcccgaga agctgggact acagccgccc    31140
accaccacgc ctggctaatt ttttgtattt ttagtagaga cgggatttca ccgtgttagc    31200
caggatggtc tcgatctctt gacctcgtga tccgcccacc tcggcctccc aaagtgctgg    31260
gattacaggc gtgagccacc actcccggcc ttttttaaaa ttttttttct gagacagtct    31320
cactttgtca cccaggcggg agtacagtgg cgcaatctca gctcacttca acctctgcct    31380
cccaggttca agcaattctc ctgcctcagc ctcccaaata gctgggacta caggtgccca    31440
ccaccatgcc cagctaattt ttgtattttt agtagagacg gggtttcatt cagttggcca    31500
ggctggtctc cttaaatgat ccgcctgcct tggcctccca aaattctggg gttacaggag    31560
tgagccactg cgtccggccc atttctcca  ctttctaaat gaggttaggt gcagccacta    31620
gccctccggt ggttcccagc tgcccttggg ataaccccca ccccttaccc tggctccccc    31680
atctccacac agcctggctc cttgtcacct cttctctgcc tcctgtcccc gcttcactca    31740
gctttggcca caagggactc ttttggtcc  ctcctacaaa caaagtgtgt tcctacccca    31800
agcctctgca tcagctattt cttccgcctt caccctcttc ctcaggtctc catgtggcag    31860
ctccctcttg acatctagag tcacctatga tgtcaccttc cctctaagag gccctcccta    31920
tctatccgag cagtctcttc tgagcacact ccactctccc ctctctgctg agttttttat    31980
tgttttcta  tttatgtact tatgctcatc tgtccactca gctagattga gcacagggta    32040
tgggtattta cttctagatc cccagcagct agggtactga ctggcacata gtaggtgctc    32100
aagaaatatt gtgaaatgag gccaggcgtg ctggctcacg cctgtaatcc cagcactttg    32160
ggaggctgag gtgggtggat cacgaggtca ggagatcgag accattctgg ctaacatggt    32220
gaaatcccgt ctctactaaa aatacacaaa attatccggg cgtggtggta ggcgcccata    32280
gtcccacctt cttaggaggc tgaggcagga gaatggcatg aacctgggag gcagagcttg    32340
cagtgagcag agatcgcact gcactccagc ctgggcgaca gagtgagact gtctcaaaaa    32400
aaaaagaaat attgtgaaat gaatagaagg tcccccagca actaggacac tagctggtgc    32460
tttaatagga ctcaaaaaat attaagtgag gccaggctgg gaggccaagg caggcggatc    32520
atttgaggtc gggagttcga gaccagcctg gccaacatgt tgaaacccca tctctactaa    32580
aaatataaaa attatccagc agtggtggcg ggcagctgta atcccagcta ctcaggaggc    32640
tgaggcagaa gaatctcttg aatctgggag gtggaggttg cagtgggctg aggtcgtacc    32700
attgtactcc agcctgggcg acagagcaag actctgtcta aaaaaaaaa  aaaaatatat    32760
atatatatat atatatatat acacgtatat atatgtgtat atatatatac atatatgtgt    32820
gtatatatat atatacgtat atatatgtgt atatatatat atatacacgt atatatatgt    32880
```

```
atatatacac acacacacac acacacacat atatattaag tgaaaagaag gtcccccagc    32940
agctggggta ctggctggca catagtaggt gctcaagaaa cattgggaaa tgaaggaaag    33000
atctcccagc agctagggca ctggctgatg cttagtagga ctcaacaact gttaagtgaa    33060
gggaatatca cccagcagct agggtaccta gcacacagta gataccaaat aaatatacac    33120
agactgaaga aaagactcga aagtgatcca ttgccaacct gaacagagaa ctctagtctg    33180
tctgattcta aaatgagccc aggagctgag acaccccga aggccagggt ggggtttgtt    33240
ccctgccccc actgggggaa gagaaggcag gcgggcagtg ggactgaggt gcctctgttt    33300
ccctgcccac ctgcctgccc acctgcccac ccggaaggat cttccctgac ctcagcagca    33360
acgacatgct cctcttcatc gtgaagggca tcaacttgcc cacaccccca ggtgaggggg    33420
ctgtaggcaa gggtcagggt catggggacc ccctctctgc ccagctctga ccgttgtttg    33480
cccacaggac tgtcccctgg cgatctggat gtctttgttc ggtttgactt ccctatccc    33540
aacgtggtac gtggggagct gaggagggga gggctgcagc ctcagtgggc caaagccagg    33600
tcccaggccc cctagatttc ctgcctcctc tctggtcata ggaagaagct cagaaagaca    33660
agaccagtgt gatcaagaac acagactccc ctggtgagcc tcggctggaa gcaccctacc    33720
cctactccct tgcagcagaa gggacataag acaatggcct gaccccaccc aacttcctct    33780
ccctccttcc tcctgcagag ttcaaggagc agttcaaact ctgcatcaac cgcagccacc    33840
gtggcttccg aagggccatc cagaccaagg catcaagtt cgaagtggtt cacaaggggt    33900
gagctagaga gagccatggc cgctgggtgg gctccagggg aggggagctc ctctgaacca    33960
accatcctgt ccccactata cacacatgca cacaggggc tgttcaagac tgaccgggtg    34020
ctggggacag cccagctgaa gctggatgca ctggagatag catgtgaggt ccgggagatc    34080
cttgaggtga gaggtggaca ttcatccgcg tgctccggta tggccatgct actcgttaac    34140
attattaaaa cacttcctgc cttgagccct ctatgagcct gtctgttgac ccagcccctc    34200
ccctcagagc ctcagacctc cctactgccc agccctaaat acttgcagta ccccactcca    34260
ttatgatcaa ctggtatctc agccatacca tgggctcata ttttagaaac cactcttggc    34320
caggcatggt ggctcatgcc tgtaatccca gcactttggg aggctgaggc gggcagatca    34380
cgaggtcagg agatcgagac catcctggct aacatggtga aaccctgttt ctactaaaat    34440
acaaaaaaat tagccaggca tggtggcggg cgcctgtagt cccagctact cgggaggctg    34500
aggcaggaga atggcgtaag taaacccagg aggcggagct tgcagtgagc ccagattgca    34560
ccactgcact ccagcctgga caacagagcg agactctatc tcagaaaaaa aaaaaaccaa    34620
aaaaaaaaac cagtcttgtt ctcccttgtc ctggccctgg gcctctagtc acttcctgct    34680
tcccaccaac agtttctcct tacccccacc caggtcctgg atggtcgccg gcccacaggg    34740
gggcgactgg aggtaatggt ccggattcgg gagccactga cagcccagca gttggagacg    34800
acgacagaga ggtggctggt cattgaccct gtgccggcag ctgtgcccac agtgagaccc    34860
cccaccccca cccatcagca accccaggga gggaagcttg gttcagggc ccaggactca    34920
caggactggt tctctcctct gaagcaggtt gctgggccca aagggaaggc ccctcctgtg    34980
cctgcccctg caagggagtc agggaacagg taggtatctg ggccaggca tgctggaaa     35040
aacacccaat tcccctctca gccccacctg gacagtttcc caccaggcac aaattggacc    35100
acgtccctct cctgctgcaa aacctttctt ggcacccctt ttcccagagg atccagttta    35160
aactccttgg tttggtcttt aaaacctttt gtgatctgac cattgtcaac atatccaggc    35220
```

-continued

```
ttctctctcc ctactccctc ctgtggttca tgtccatgaa tagttttcac tggcctctgg    35280
acttctgtgg gttccagtgc cctgaacacc cctacctagg gtagggtgt tccttgttcc     35340 tctgcccacc tctgattcct tctttggatc ccaacttggc tgttacctcc tccaggaagc    35400
cctccctgac cactaggcat catagtttcc tgggtgtgca gccatcatcc ccgctaggtt    35460
ttgggatcag taacaccggg tggttctcgg ctgtctccca ccatacccc agtgcccagt     35520 gtgtcttttt ttttttttt tttttttgag acagagtcta gctctgtcgc ccaggctaga     35580
gtgcaatggc gcgatctcag ctcacagcaa cctccgcctc tggggttcaa gcgattctcc    35640
tgcctcagcc tcctgagtag ctgggattac aggcatgcgc caccacccc agctaatttt     35700 tctattttta gtagagatgg gtttctcca tgttggtcag gctggtctcg aactcccgac     35760
ctcaggtgat ctgcctgcct cggcctccca aagtgctggg attacaggca tgagctacca    35820
tgctcggctt ttttttttt ttgagacaga atcttgctct gtcacccagg ttggagtgca    35880
gtggtgtgat ctcggctcat tgcaacctcc agctcccagg ttcaagcaat tcttctgcct    35940
cagcctccca agtagctggg actacaggag cacaccacca tgcccagcta attttttttc    36000 tattttagt agagacgggg tttcaccata ttggccaggc tggtctcgaa ctcctgacct    36060
catgatccac tcacctccgc ctcccaaagt gcagggatta caggcgtgag ccactgtgcc    36120
cagcccagtg tgtcttttga attaacaggg ttgggctggg ggaatctctg cagtcccta    36180 tccttcctcc accccttaga tcagcccggc ccctgcatag cctcagtgtg ctggcgtttg    36240
accaagagcg tctggagcgg aaggtgggta tccatcctgc cgggctacat ggggcaggac    36300
tggggagtct gcaggcccag gcaggatcct cacaggaccc tctgtatcct ctagatcctg    36360
gccctcaggc aggcgcggcg gccggtgccc ccagaagtgg cccagcagta ccaggacatc    36420
atgcaacgca gccagtggca gagggcacag ctggagcagg ggggtgtggg catccgacgg    36480 ggtagggtt tggagatggg catctggtgg gggaggagct ccaggatagg catgggggg     36540 gaggtgctca gggatgcata tctggtgggg gaggggctcg gggatgggca tctggagagg    36600
gaggggctcg gggatgggca cctggagggg gaggggctcg gggatgggca cctggagggg    36660
gaggggctcg gggatgggca tctggagagg gaggggctcg gggatgggca cctggagggg    36720
gaggggctcg gggatgggca cctggagggg gaggggctcg gggatgggca cctggagggg    36780
gaggggctcg gggatgggca cctggcgggg gacgggcttg gggatgggca cagtccagga    36840
gggttgtggg cagtgaggcc ccaccctaag cctccattcc cccgccatcc attctcagaa    36900
tacgcagccc agctggagcg gcagctgcag ttctacacgg aggctgcccg gcgcctgggc    36960
aacgatggca gcagggtgag ctggtcgcgg gccgggtggg cactgggcag cgggcagggt    37020
ggggcctgca gggactacct gctgaatgcc catcccccac aggatgctgc aaaggaggcg    37080
ctctataggc ggaatctggt agagagtgag gtaagcagct taggagatgg ggtggttggg    37140
ggatcactgt ggtcgtagcc cacctccatg accccagtgg cctcctctcc cccagctgca    37200
gcggctccgc aggtgaggag cccatgggc gggcagcccc cagaaagcgg gcagcaggcc    37260
ccgataccgg gaagagccga cacagccacg aaccagacaa gcagacaatc agcggacaat    37320
cggttctgga ctcacccctc atccgggccc ccagcccgc cagagcctcc gtggctgcgg    37380
gtgttgggaa ccatgcctgc cagccagtat gtgcccctca cccaggcctg gctgggccct    37440
ggagagtcct gtttgcacag cccaggggtg tccggcctct ggcccgcccc ggagcaggga    37500
gggtggctgg ggccaagccc cgagggcccc tgcaagcact ttacttcctg ttcctcccca    37560
gccttaaccc caaagccctc ctgcacccca aagaagccac tgaggctggc cgagccacac    37620
```

```
tgtctcccca ggggcgtcga cctggcccag ctgggtcccc agggccagca catggaataa    37680
aatagccagg gccacactca                                                37700
```

METHODS AND KITS FOR DIAGNOSING AND TREATING MENTAL RETARDATION

RELATED APPLICATION

This application claims the benefit of U.S. Provisional Patent Application No. 60/698,039 filed Jul. 12, 2005, the contents of which is incorporated herein by reference.

FIELD AND BACKGROUND OF THE INVENTION

The present invention relates to methods and kits for diagnosing and treating pathologies associated with mental retardation such as nonsyndromic mental retardation (NSMR) and/or infantile bilateral striatal necrosis (IBSN).

Mental retardation affects approximately 1% to 3% of the general population. Defining features of mental retardation include intellectual functioning level (IQ) below 70, significant limitations in two or more adaptive skill areas, and presence from childhood (defined as age 18 or less). Genetic etiologies are found in approximately two thirds of mental retardation cases. An autosomal recessive mode of inheritance may account for nearly a quarter of all individuals with nonsyndromic mental retardation (NSMR). NSMR is the diagnosis of exclusion in mentally retarded individuals who do not have major physical abnormalities, dysmorphism or neurological abnormalities. Biological processes involved in neuronal differentiation, synaptic plasticity, synaptic vesicle cycling and gene expression regulation are considered to be important in the causation of mental retardation.

Although clinical diagnosis of mental retardation can be made using accepted intellectual tests and psychological evaluations, there is a need to develop a conclusive diagnostic test for mental retardation in suspected subjects (e.g., children) and/or for prenatal diagnosis of fetuses in families with affected or unaffected siblings.

While a number of X-linked genes associated with NSMR have been identified, there is a large gap in the knowledge regarding the genetic basis of autosomal mental retardation due to heterogeneity and the absence of clinical criteria for grouping the NSMR families for linkage analysis. Only two autosomal genes, the PRSS12 gene on chromosome 4q26 and the CRBN gene on chromosome 3p26, have been shown to cause autosomal recessive NSMR, each gene in only one family (1, 2). Thus, it is clear that multiple genetic components may play a role in the pathogenesis of NSMR and it is therefore desired to further decipher the entire genetic components causing mental retardation in order to enable accurate diagnosis, prenatal diagnosis and treatment.

In a linkage analysis study performed by Basel-Vanagaite L., et al (3), four consanguineous families with severe autosomal recessive NSMR comprising 10 affected and 24 unaffected individuals were clinically evaluated and the disease locus was mapped on chromosome 19p13.12-p13.2 to an interval of 2.4 Mb, between the loci D19S547 proximally and D19S1165 distally (3). However, to date, no disease-causing mutations were identified in any of the genes reside in this locus. In addition, since the candidate region spans over 2.4 Mb, it was impossible to predict which of the genes in this chromosomal interval might be involved with NSMR.

Infantile bilateral striatal necrosis (IBSN) [MIM 271930] is a neurological disorder characterized by symmetrical degeneration of the caudate nucleus, putamen, and the globus pallidus, with little involvement of the rest of the brain. The clinical features of IBSN include developmental regression, choreoathetosis, dystonia, spasticity, dysphagia, failure to thrive, nystagmus, optic atrophy, and mental retardation. Familial IBSN has been reported, suggesting the presence of an autosomal recessive mode of inheritance. In families with mitochondrial inheritance, mutations in the adenosine triphosphatase 6 gene (complex V) have been described (5, 6).

Straussberg R et al., identified and clinically evaluated six consanguineous families with autosomal recessive IBSN (7). The candidate locus for IBSN was mapped to the chromosomal region 19q13.32-13.41, between the markers D19S596 and D19S867, spanning a 1.2 Mb chromosomal region (8). However, due to the lack of identification of a specific gene causing IBSN, no molecular diagnosis can be performed in suspected individuals or in prenatal diagnosis of fetuses in families with affected or unaffected siblings.

There is thus a widely recognized need for, and it would be highly advantageous to have, a method of diagnosing pathologies associated with mental retardation devoid of the above limitations.

SUMMARY OF THE INVENTION

According to one aspect of the present invention there is provided a method of diagnosing non-syndromic mental retardation (NSMR) in an individual, the method comprising analyzing a sequence of a CC2D1A of the individual, wherein an alteration in the sequence resulting in downregulation of an expression level and/or activity of the CC2D1A is indicative of the non-syndromic mental retardation, thereby diagnosing the non-syndromic mental retardation in the individual.

According to another aspect of the present invention there is provided a method of diagnosing non-syndromic mental retardation (NSMR) in an individual, the method comprising detecting an expression level of a CC2D1A of the individual, wherein a decrease in the expression level compared to the expression level of the CC2D1A of an unaffected individual is indicative of the non-syndromic mental retardation, thereby diagnosing the non-syndromic mental retardation in the individual.

According to yet another aspect of the present invention there is provided an isolated nucleic acid sequence capable of specifically hybridizing to a mutated CC2D1A and not to a wild-type CC2D1A nucleic acid sequence.

According to still another aspect of the present invention there is provided an antibody comprising an antigen recognition region capable of specifically binding to a mutated CC2D1A and not to a wild-type CC2D1A amino acid sequence.

According to an additional aspect of the present invention there is provided a kit for diagnosing non-syndromic mental retardation in an individual, the kit comprising a reagent for analyzing a sequence of a CC2D1A of the individual wherein an alteration in the sequence resulting in downregulation of an expression level and/or activity of the CC2D1A.

According to yet an additional aspect of the present invention there is provided a kit for diagnosing non-syndromic mental retardation in an individual, the kit comprising a reagent for detecting an expression level of a CC2D1A of the individual wherein a decrease in the expression level compared to the expression level of the CC2D1A of an unaffected individual is indicative of the non-syndromic mental retardation.

According to still an additional aspect of the present invention there is provided a method of diagnosing infantile bilateral striatal necrosis (IBSN) in an individual, the method comprising analyzing a sequence of a nup62 of the individual, wherein an alteration in the sequence resulting in downregulation of an expression level and/or activity of the nup62 is indicative of the infantile bilateral striatal necrosis, thereby diagnosing the infantile bilateral striatal necrosis in the individual.

According to a further aspect of the present invention there is provided a method of diagnosing infantile bilateral striatal necrosis (IBSN) in an individual, the method comprising detecting an expression level of a nup62 of the individual, wherein a decrease in the expression level compared to the expression level of the nup62 of an unaffected individual is indicative of the infantile bilateral striatal necrosis, thereby diagnosing the infantile bilateral striatal necrosis in the individual.

According to yet a further aspect of the present invention there is provided an isolated nucleic acid sequence capable of specifically hybridizing to a mutated nup62 and not to a wild-type nup62 nucleic acid sequence.

According to still a further aspect of the present invention there is provided an antibody comprising an antigen recognition region capable of specifically binding to a mutated nup62 and not to a wild-type nup62 amino acid sequence.

According to still a further aspect of the present invention there is provided a kit for diagnosing infantile bilateral striatal necrosis in an individual, the kit comprising a reagent for analyzing a sequence of a nup62 of the individual wherein an alteration in the sequence resulting in downregulation of an expression level and/or activity of the nup62.

According to still a further aspect of the present invention there is provided a kit for diagnosing infantile bilateral striatal necrosis (IBSN) in an individual, the kit comprising a reagent for detecting an expression level of a nup62 of the individual wherein a decrease in the expression level compared to the expression level of the nup62 of an unaffected individual is indicative of the infantile bilateral striatal necrosis.

According to still a further aspect of the present invention there is provided a method of diagnosing a pathology associated with mental retardation in an individual, the method comprising analyzing a sequence of a CC2D1A and/or nup62 of the individual, wherein an alteration in the sequence resulting in downregulation of an expression level and/or activity of the CC2D1A or the nup62 is indicative of the pathology associated with mental retardation, thereby diagnosing the pathology associated with mental retardation in the individual.

According to still a further aspect of the present invention there is provided a method of diagnosing a pathology associated with mental retardation in an individual, the method comprising detecting an expression level of a CC2D1A and/or nup62 of the individual, wherein a decrease in the expression level compared to the expression level of the CC2D1A or the nup62 of an unaffected individual is indicative of the pathology associated with mental retardation, thereby diagnosing the pathology associated with mental retardation in the individual.

According to still a further aspect of the present invention there is provided a method of treating a pathology associated with mental retardation, comprising upregulating in a cell of an individual in need thereof an activity of CC2D1A or nup62, thereby treating the mental retardation.

According to further features in preferred embodiments of the invention described below, analyzing the sequence of the CC2D1A is effected by an isolated nucleic acid sequence capable of specifically hybridizing to a mutated CC2D1A and not to a wild-type CC2D1A nucleic acid sequence.

According to still further features in the described preferred embodiments the mutated CC2D1A nucleic acid sequence comprises a sequence alteration which results in downregulation of an expression level and/or activity of the CC2D1A.

According to still further features in the described preferred embodiments the alteration in the sequence is a deletion of nucleic acids 13891337-13894926 of a genomic sequence of the CC2D1A as set forth by GenBank Accession No. NC_000019.8.

According to still further features in the described preferred embodiments the isolated nucleic acid sequence is bound to a solid support.

According to still further features in the described preferred embodiments the isolated nucleic acid sequence is labeled.

According to still further features in the described preferred embodiments analyzing the sequence of the CC2D1A is effected by an antibody which comprises an antigen recognition region capable of specifically binding to a mutated CC2D1A and not to a wild-type CC2D1A amino acid sequence.

According to still further features in the described preferred embodiments the mutated CC2D1A amino acid sequence comprises an amino acid sequence alteration which results in downregulation of an expression level and/or activity of the CC2D1A.

According to still further features in the described preferred embodiments the mutated CC2D1A is set forth by SEQ ID NO:5.

According to still further features in the described preferred embodiments the antibody is bound to a solid support.

According to still further features in the described preferred embodiments the antibody is labeled.

According to still further features in the described preferred embodiments detecting the expression level of the CC2D1A is effected by an isolated nucleic acid sequence capable of specifically hybridizing to a nucleic acid sequence of the CC2D1A.

According to still further features in the described preferred embodiments detecting the expression level of the CC2D1A is effected by an antibody which comprises an antigen recognition region capable of specifically binding to an amino acid sequence of the CC2D1A.

According to still further features in the described preferred embodiments analyzing the sequence of the nup62 is effected by an isolated nucleic acid sequence capable of specifically hybridizing to a mutated nup62 and not to a wild-type nup62 nucleic acid sequence.

According to still further features in the described preferred embodiments the mutated nup62 nucleic acid sequence comprises a sequence alteration which results in downregulation of an expression level and/or activity of the nup62.

According to still further features in the described preferred embodiments the alteration in the sequence is a missense mutation 1429A→C as set forth by SEQ ID NO:68.

According to still further features in the described preferred embodiments analyzing the sequence of the nup62 is effected by an antibody which comprises an antigen recognition region capable of specifically binding to a mutated nup62 and not to a wild-type nup62 amino acid sequence.

According to still further features in the described preferred embodiments the mutated nup62 amino acid sequence comprises an amino acid sequence alteration which results in downregulation of an expression level and/or activity of the nup62.

According to still further features in the described preferred embodiments the mutated nup62 comprises a proline residue at amino acid 391 as set forth by SEQ ID NO:69.

According to still further features in the described preferred embodiments detecting the expression level of the nup62 is effected by an isolated nucleic acid sequence capable of specifically hybridizing to a nucleic acid sequence of the nup62.

According to still further features in the described preferred embodiments detecting the expression level of the nup62 is effected by an antibody which comprises an antigen recognition region capable of specifically binding to an amino acid sequence of the nup62.

The present invention successfully addresses the shortcomings of the presently known configurations by providing methods and kits for diagnosing and treating mental retardation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figures 1A, 1B:
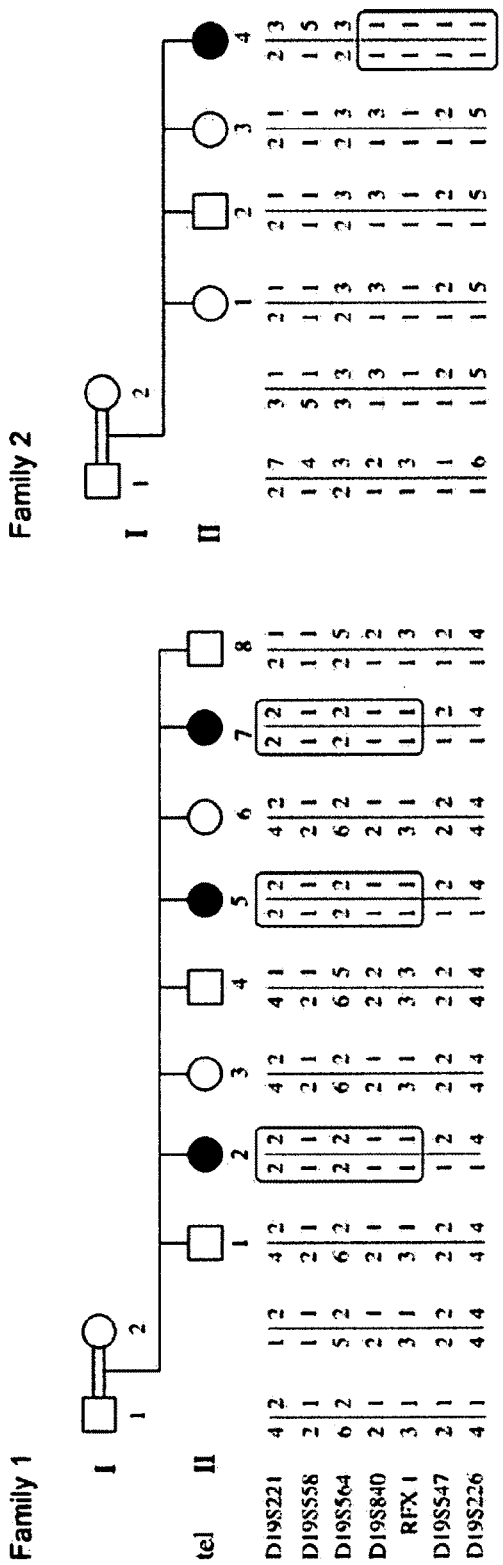
Figure 1C:
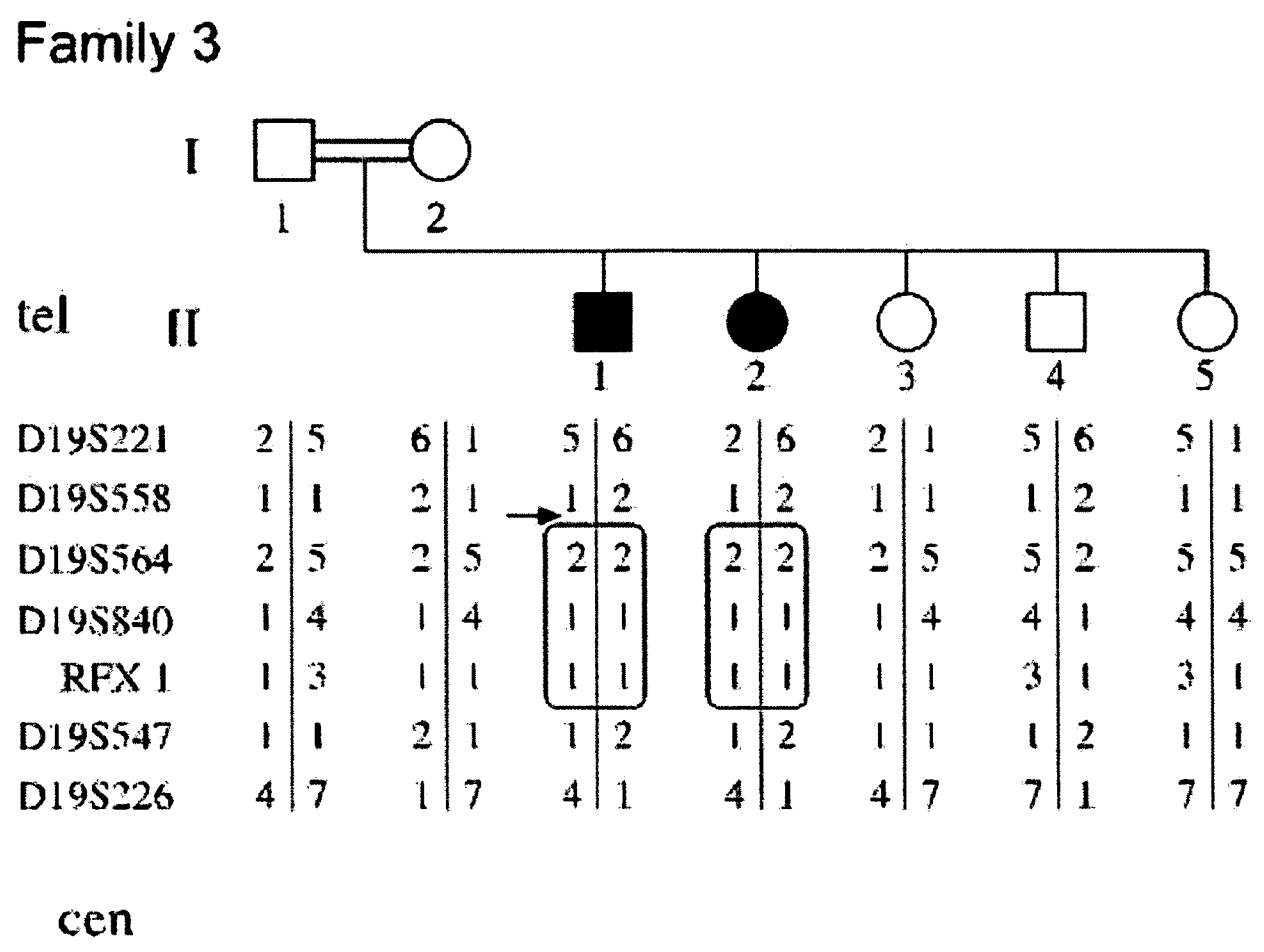
Figure 1D:
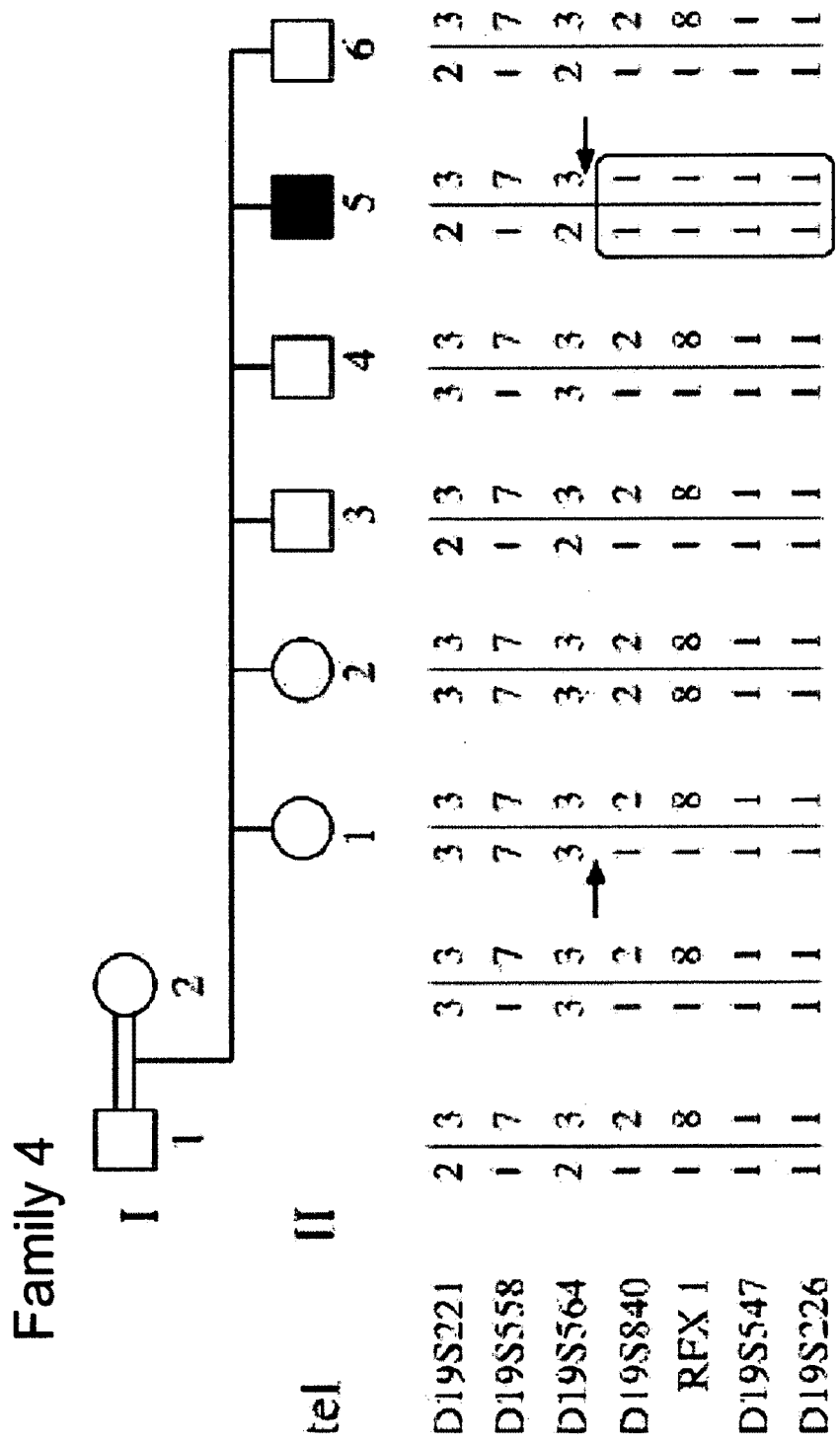
Figure 1E:
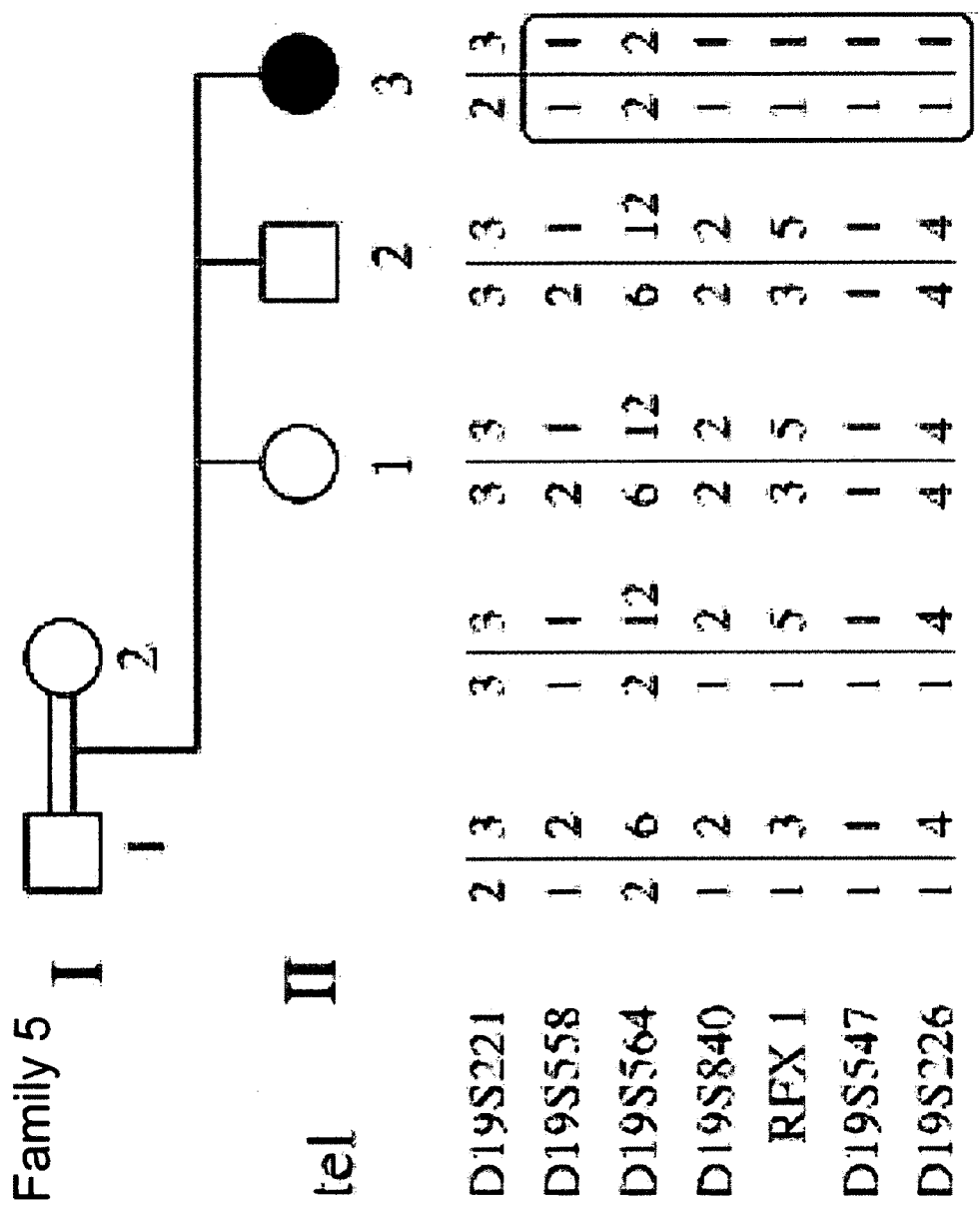
Figure 1F:
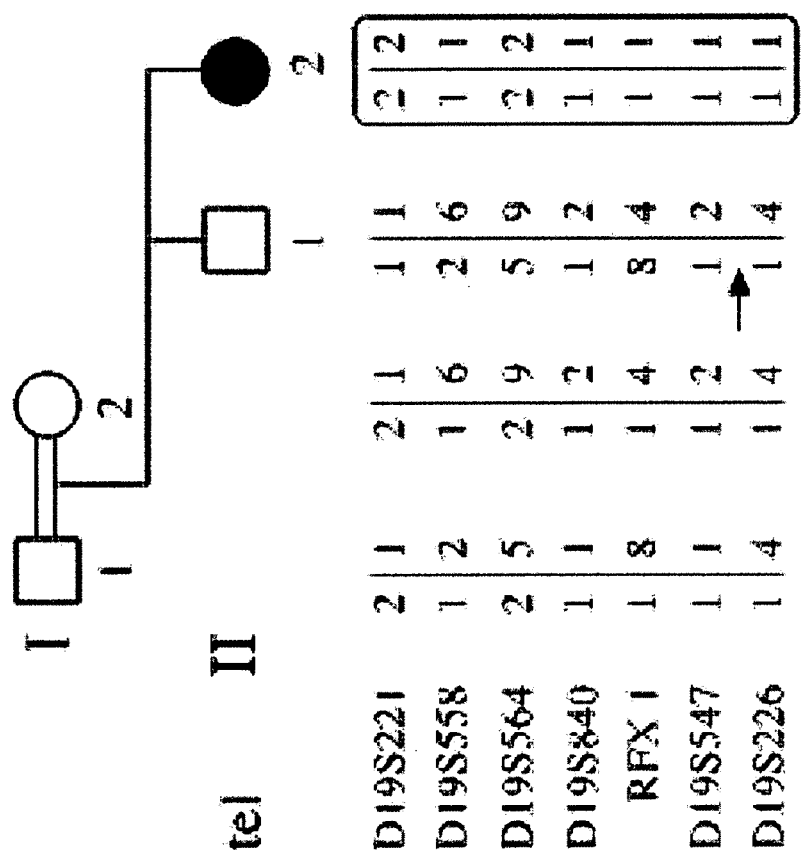
Figure 1G:
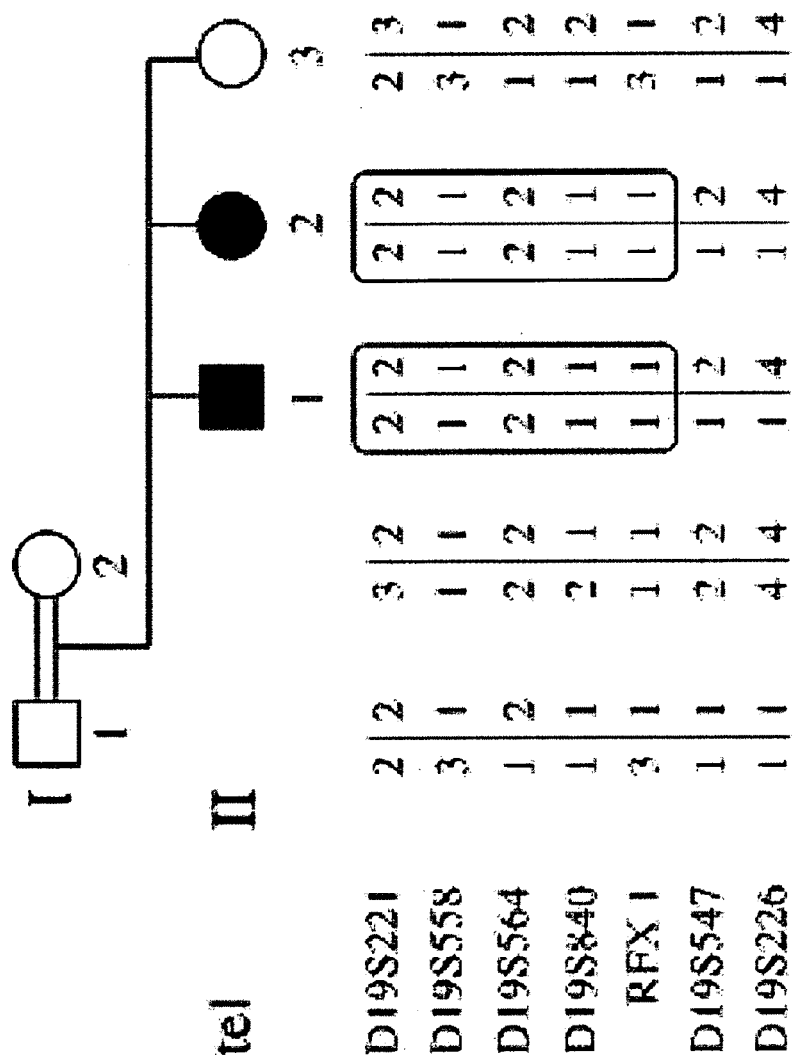
Figure 1H:
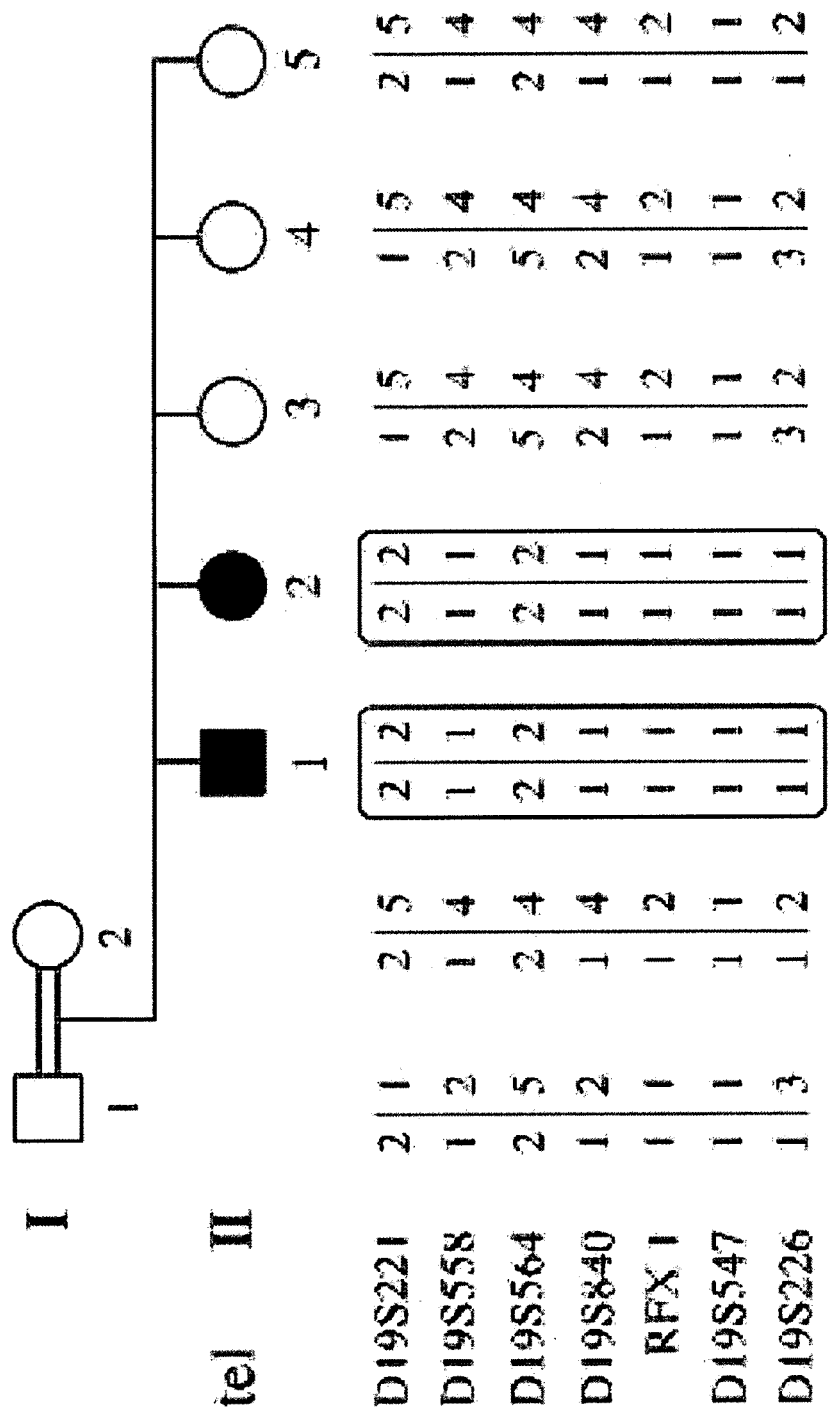
Figure 2:
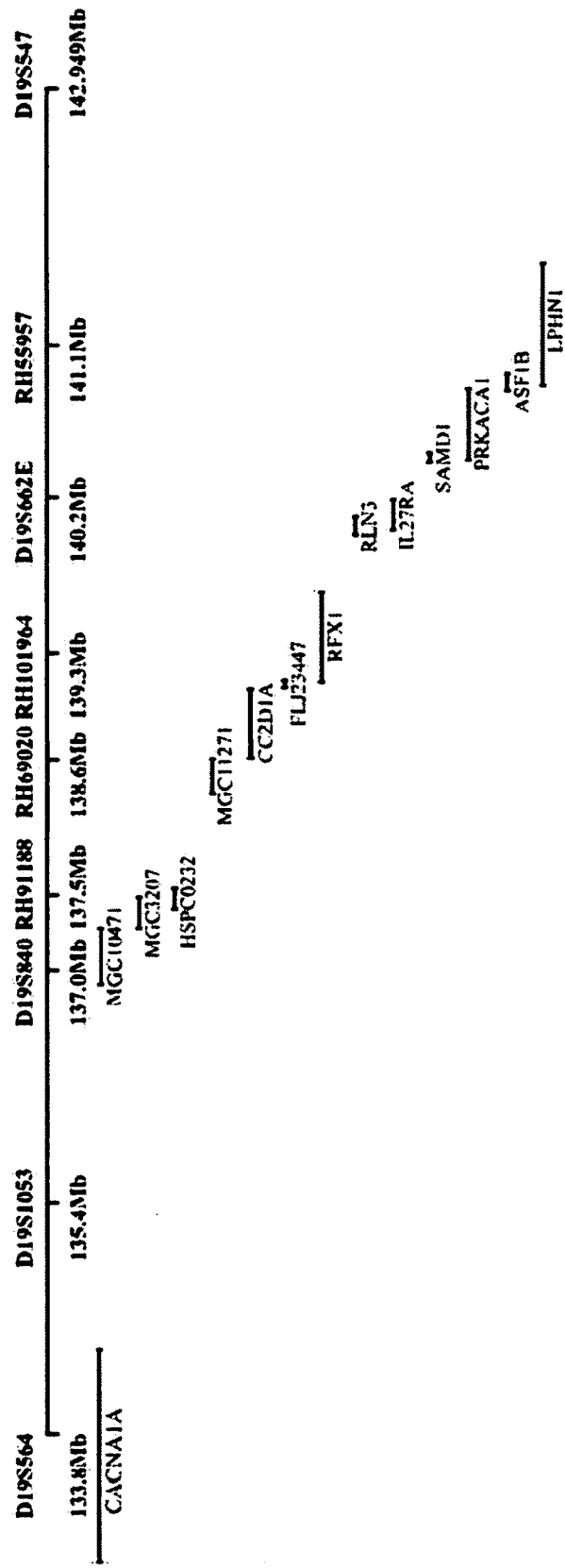

FIGS. 1a-i are schematic presentations of linkage analyses depicting the genotypes of informative markers in 9 consanguinity families (pedigrees) with autosomal recessive non-syndromic mental retardation (NSMR) and demonstrating fine mapping of NSMR critical region on ~900 kb between markers D19S564 and D19S547 on chromosome 19p13.12-p13.2. The candidate region is defined by loss of homozygosity in affected individuals. Black symbols in the pedigree represent affected individuals. The boxed regions indicate the homozygous regions in each affected individual. The polymorphic markers are shown left of each pedigree and are ordered according to their relative position on the chromosome from the telomere (tel) direction to the centromere (cen) direction: D19S221, D19S558, D19S564, D19S840, RFX 1, D19S547, D19S226. Arrows indicate informative recombinations. FIG. 1a—Family 1; FIG. 1b—Family 2; FIG. 1c—Family 3; FIG. 1d—Family 4; FIG. 1e—Family 5; FIG. 1f—Family 6; FIG. 1g—Family 7; FIG. 1h—Family 8 FIG. 1i—Family 9;

FIG. 2 is a diagram depicting the defined critical region of NSMR on chromosome 19 with the relative position of the genes. The polymorphic markers used for analysis are shown on the top (D19S564, D19S1053, D19S840, RH91188, RH69020, RH101964, D19S662E, RH55957 and D19S547) along with their relative distance (in Mb) from the centromere. The genes included in the candidate region are shown underneath the polymorphic markers, along with their relative size and location: MGC10471, MGC3207, HSPC0232, MGC11271, CC2D1A, FLJ23447, RFX1, RLN3, IL27RA, SAMD1, PRKACA1, ASF1B and LPHN1.

Figures 3A, 3B:
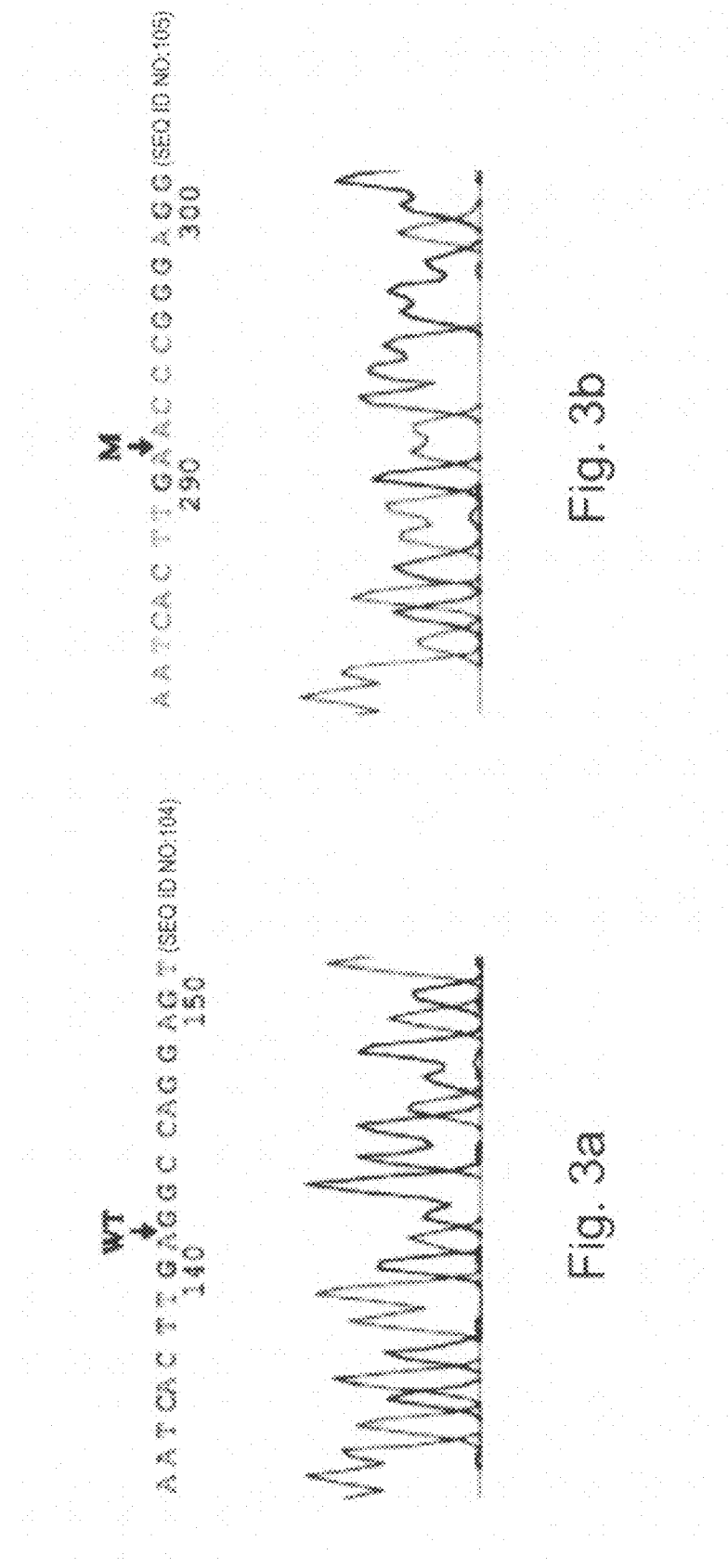

FIGS. 3a-b are sequence analyses chromatograms from a wild-type (WT; FIG. 3a) and disease (M; FIG. 3b) genotypes performed using cDNA from control (i.e., unaffected with NSMR) and NSMR affected individual showing the deletion mutation.

Figures 4A, 4B:
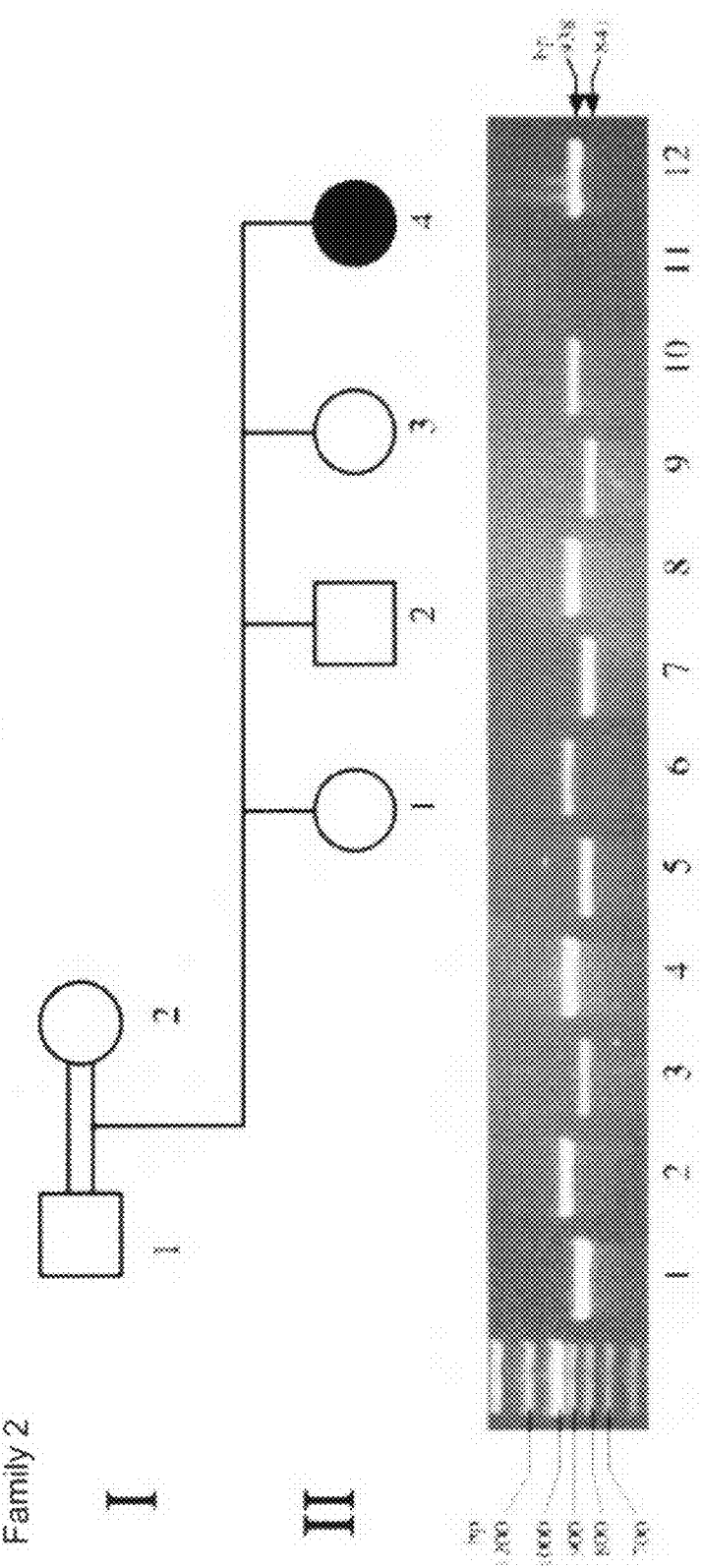

FIGS. 4a-b are a schematic presentation of a pedigree of Family 2 (FIG. 4a) and a PCR analysis (FIG. 4b) depicting the segregation of the deletion mutation in CC2D1A as assayed on the genomic DNA. Two separate PCR reactions with primers A+B (SEQ ID NOs:6 and 7) and A+C (SEQ ID NOs:6 and 8) were performed as described under General Materials and Experimental Methods of the Examples section. Amplification with primers A+B (lanes 1, 3, 5, 7, 9) resulted in the 841 bp PCR product only in normal alleles, while amplification with primers A+C (lanes 2, 4, 6, 8, 10, 12) resulted in the 938 bp PCR product only in alleles carrying the deletion. Primer A was derived from exon 13 (upstream of the deletion), primer B from intron 14 (within the deletion), and primer C from exon 19 (downstream the deletion). Subject I1 (lanes 1+2), subject I2 (lanes 3+4), II1 (lanes 5+6), subject II2 (lanes 7+8), II3 (lanes 9+10) and subject II4 (lanes 11+12). Note that while all family members except the affected individual (subject II4) carry one allele with the deletion (938 bp) and one normal allele (841 bp), i.e., being heterozygote for the deletion, the affected individual (subject II4) carries only the deleted allele, i.e., being homozygote to the deletion.

Figure 5:
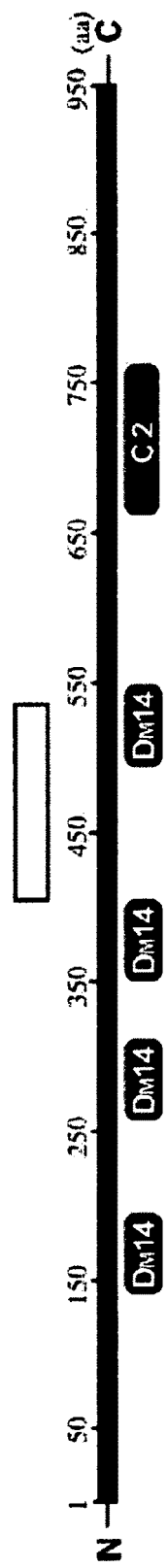

FIG. 5 is a schematic diagram of the CC2D1A gene structure showing the main domains of the protein; white bar depicts the relative position of the deletion mutation. "N" and "C" denote the N-terminal and C-terminal ends, respectively, of the CC2D1A protein (GenBank Accession No. NP_060191); DM14 denotes DM14 domain (or motif); C2 denotes the C2 domain (IPR008973, IPR006608, IPR000008) which participates in the binding pocket of the $Ca^{+2}$ cation and is found in proteins which function in calcium-dependent phospholipid binding (B. A. Davletov, T. C. Suedhof, J. Biol. Chem. 268: 26386, 1993).

FIGS. 6a-b are Western blot analyses depicting CC2D1A expression pattern in NSMR affected or unaffected individuals. Lymphoblast cells from an NSMR affected individual (Patient) or an unaffected individual (Control) were subjected to Western blot analysis using a CC2D1A antibody (FIG. 6a) or a control antibody directed against Emerin (FIG. 6b). A protein band of 104 kDa was observed in the unaffected individual (FIG. 6a, arrow on the right) but not in the NSMR affected individual, demonstrating the absence of a normal CC2D1A protein in the lymphoblasts of affected individuals. On the other hand, a smaller protein of approximately 85 kDa (FIG. 6a, arrowhead on the left) was observed in the patients, demonstrating the presence of a truncated CC2D1A protein in individuals affected with NSMR. A few additional bands at variable intensities were also detected. No difference in the size and/or intensity of a control protein Emerin was detected between the NSMR affected or unaffected individuals (FIG. 6b).

FIG. 7 is a fluorescence immunostaining of CC2D1A in U2OS cells. U2OS cells were fixed, immuno-stained (orange) with rabbit anti-CC2D1A antibodies (Bethyl laboratories), and analyzed by fluorescent microscopy. The nuclei were stained with DAPI (blue). Note that CC2D1A staining is localized to the cytoplasm of U2OS cells.

Figure 8:
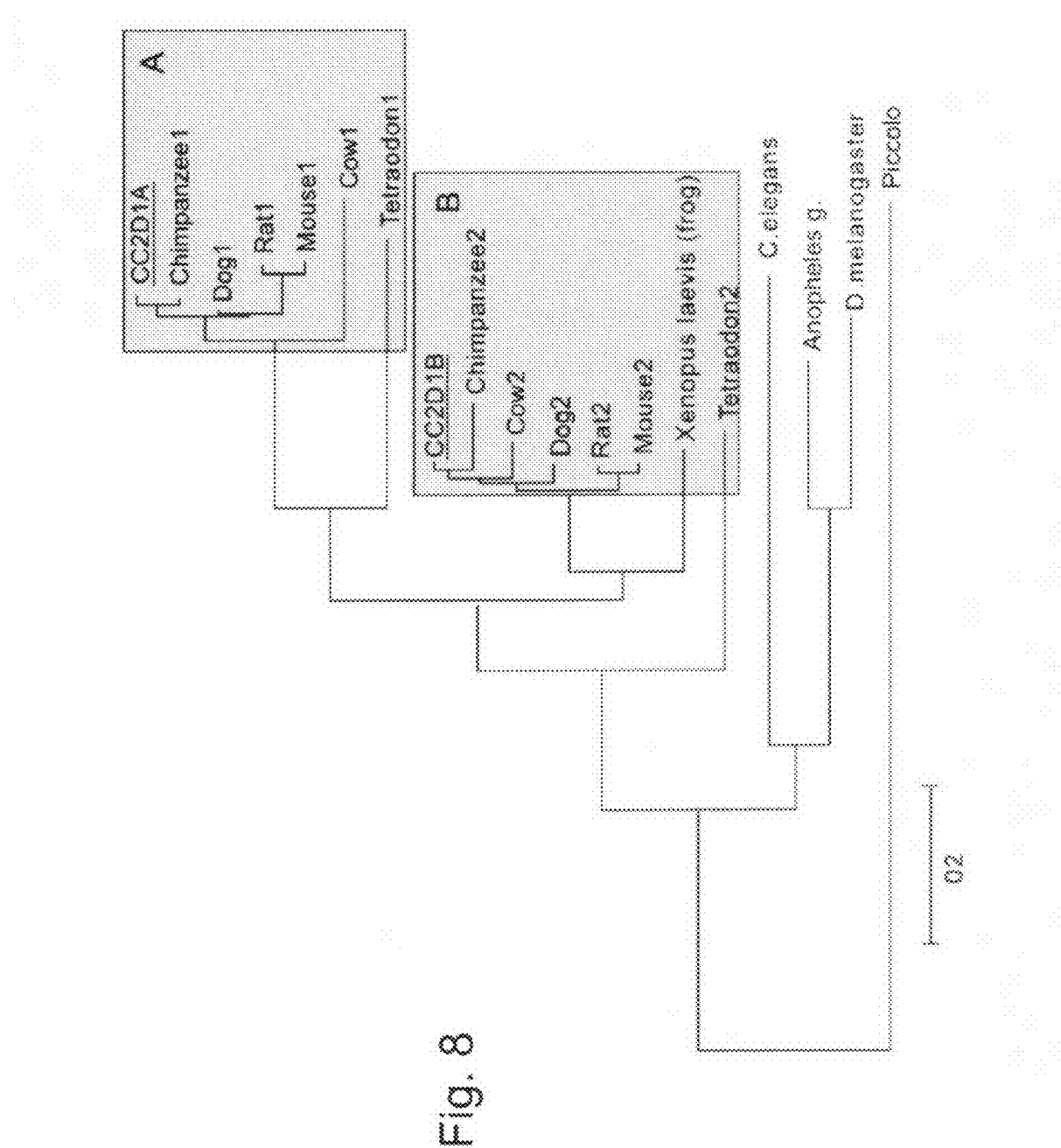

FIG. 8 is a phylogenetic analysis of the CC2D1A protein family. The two invertebrate branches, A and B, are emphasized by the gray boxes. The mouse protein Piccolo (aczonin, presynaptic cytomatrix protein; GenBank Accession No. NP_036125) serves as an out group which allows to determine the direction of evolution in a phylogenetic analysis. GenBank Accession numbers for the family members are: NP_060191 (CC2D1A), XP_542027 (Dog1), NP-001013891 (Rat1), NP_666082 (Mouse1), XP_614352 (Cow1), CAG06037 (Tetraodon1), AAH07912 (CC2D1B) XP_513407 (Chimpanzee2), XP_588670 (Cow2), XP_539614 (Dog2), XP_233342 (Rat2), NP_796019 (Mouse2), CAG07113 (Tetraodon2), AAH57723 (*Xenopus laevis*), CAB63350 (*C. elegans*), EAA09979 (*Anopheles* g.), NP_609488 (*D. melanogaster*). The protein Chimpanzee1 was defined from the chimpanzee genome [chr20: 14509949-14533811 (November 2003)] by aligning the human mRNA using Sim4 (A. L. Pidoux, W. Richardson, R. C. Allshire, J. Cell Biol. 28, 295, 2003) and translation of the prediction (SEQ ID NO:70). Tetraodon2 is a result of Genescan prediction (Burge, C. and Karlin, S. 1997, Prediction of complete gene structures in human genomic DNA. J. Mol. Biol. 268, 78-94) of the genomic sequence of the region chr15_random: 1575804-1583914 (SEQ ID NO:71). The phylogenetic analysis included multiple alignment using ClustalX (J. D. Thompson, T. J. Gibson, F. Plewniak, F. Jeanmougin, D. G. Higgins, Nucl. Ac. Res. 24, 4876, 1997), and dendogram creation with MEGA2 (S. Kumar, K. Tamura, M. Nei, Comput. Appl. Biosc. 10, 189, 1994) using Neighbor-Joining (N. Saitou, M. Nei, Mol. Biol. Evol. 4, 406, 1987).

Figure 9A:
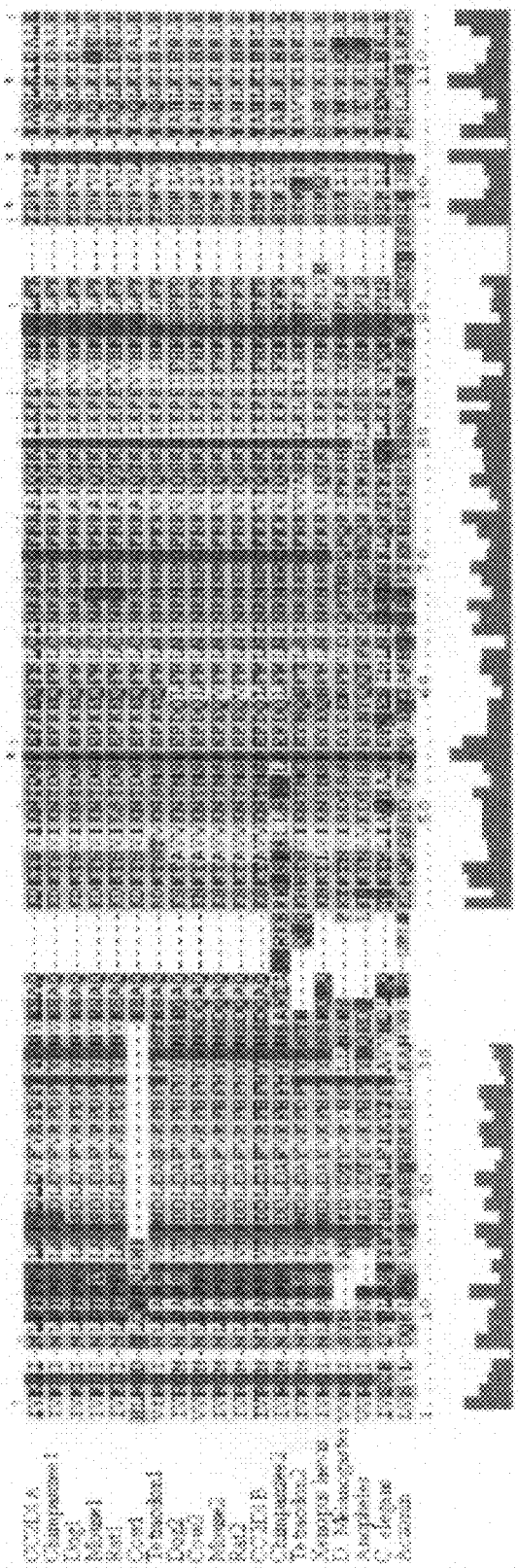
Figure 9B:
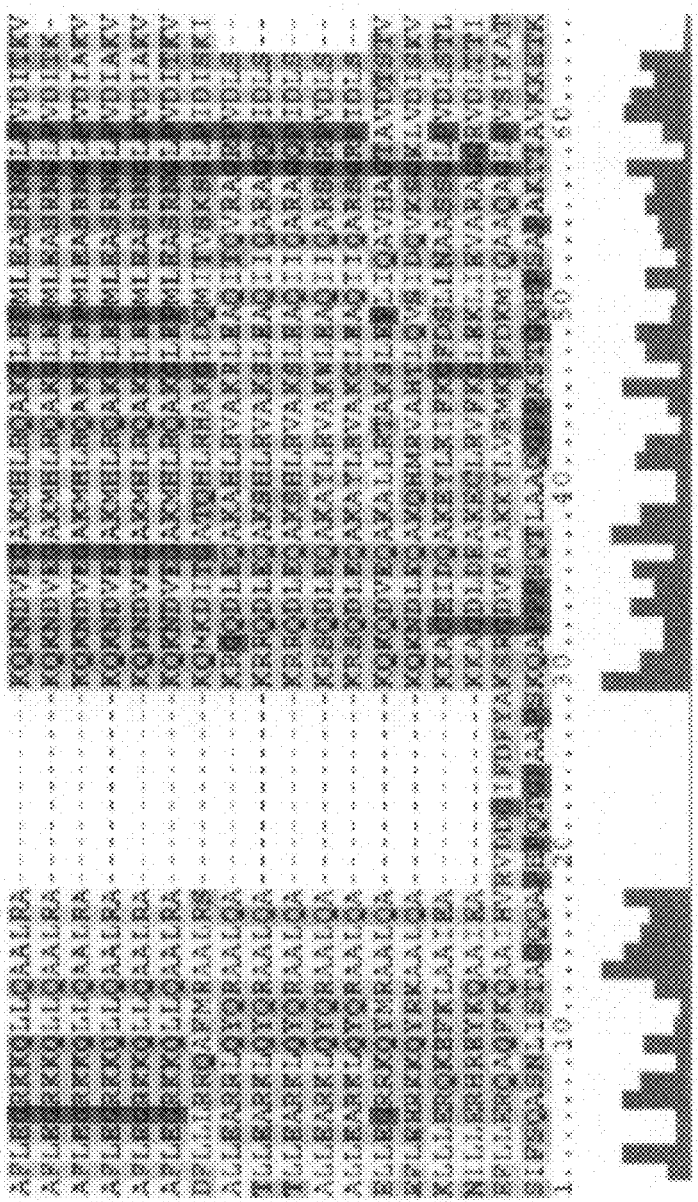

FIGS. 9*a-b* are multiple alignment of the C2 domain (FIG. 9*a*) and one of the DM14 domains (FIG. 9*b*). Shown are partial amino acid sequences of the aligned proteins which share homology and/or similarity with the C2 or DM14 domains of CC2D1A. The complete nucleic acid sequences of the aligned proteins are provided by the following GenBank Accession Nos. and/or SEQ ID NOs: CC2D1A (NP_060191; SEQ ID NO:4), Chimpanzee1 (SEQ ID NO:70, Dog1 (XP_542027), Mouse1 (NP_666082), Rat1 (NP_001013891), Cow1 (XP_614352), Tetradon1 (CAG06037), Dog2 (XP_539614), Cow2 (XP_588670), Mouse2 (NP_796019), Rat2 (XP_233342), CC2D1B (AAH07912), Chimpanzee2 (XP_513407), Tetradon2 (CAG07113), *Xenopus laevis* (AAH57723), *D. Melanogaster* (NP_609488), *Anopheles* (EAA09979), *C. elegans* (CAB63350), Aczonin (NP_036125). The alignment was performed with ClustalX. Strongly conserved positions are marked on top, where '*' indicates positions that are occupied by a single amino-acid, while ':' and '.' are for positions where a conserved substitution has occurred. The conservation graph is shown below. Note that some positions in the aczonin protein were truncated to allow a better alignment of the C2 domain. These are marked by the '~' sign.

Figure 10B:
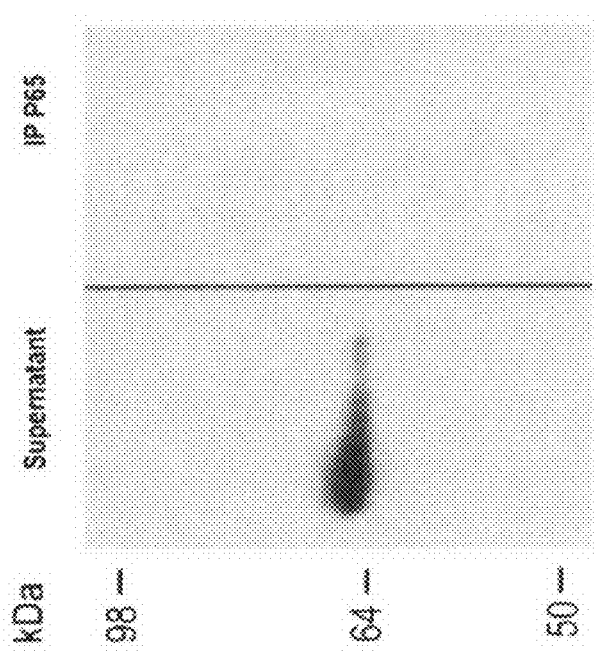
Figure 10A:
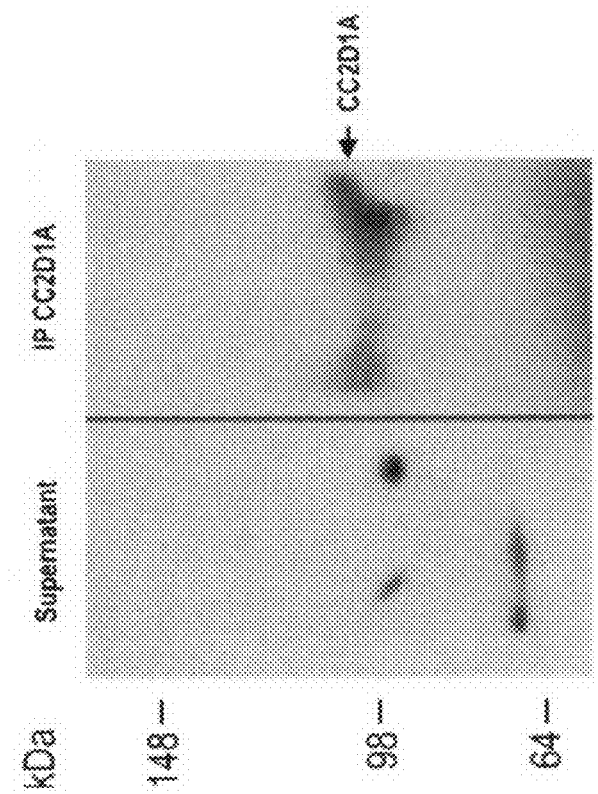

FIGS. 10*a-b* are co-immunoprecipitation analyses of CC2D1A and p65 subunit of NF-κB. Lymphoblastoid cell extracts derived from normal, unaffected individuals were immunoprecipitated with antibodies to CC2D1A. Immunoprecipitates were resolved with SDS-polyacrylamide gel electrophoresis (SDS-PAGE), and associated proteins were identified by Western blot with antibodies directed against to CC2D1A (FIG. 10*a*) or p65 (FIG. 10*b*). Note that while the immunoprecipitated complex included CC2D1A (FIG. 10*a*, arrow on the right), no signal was observed with the p65 antibody (FIG. 10*b*), demonstrating the lack of direct association between CC2D1A and p65.

Figure 11A:
Figure 11B:
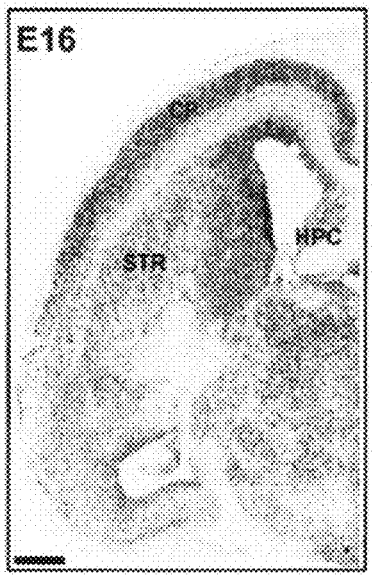
Figure 11C:
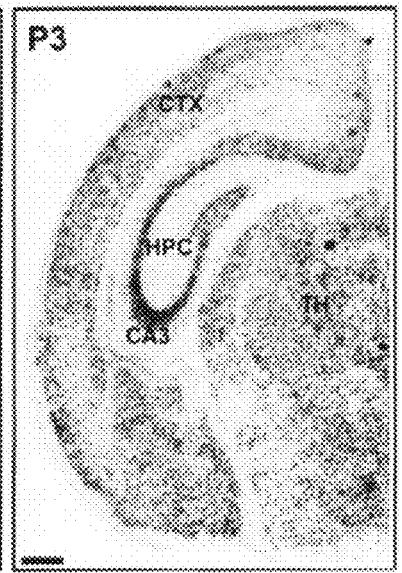

FIGS. 11*a-d* are in situ hybridization analyses of CC2D1A mRNA depicting the expression of CC2D1A in the brain, mainly in the cerebral cortex and hippocampus. Expression of CC2D1A mRNA is seen in murine brain at embryonic day E12 (mouse embryonic date 12) and in adult mice. CC2D1A mRNA expression is found throughout the ventricular zone progenitor cells and developing cortical plate. Later in development at E16 (mouse embryonic date 12), CC2D1A mRNA is found throughout the cortical plate and developing hippocampus. During the postnatal period of brain development (P3; 3 days postnatal), CC2D1A mRNA expression is widely expressed throughout the brain, but particularly in the cerebral cortex and hippocampus, especially CA3 of the hippocampus. In adult brain, the expression of CC2D1A mRNA is widespread but appears restricted mostly to neurons. The scale bar in FIGS. 11*a-c* is 500 µm and the in FIG. 1*d* is 1 mm. CC: corpus callosum; CBL: cerebellum; CP: cortical plate; CTX: cerebral cortex; GE: ganglionic eminences; HPC: hippocampus; OB: olfactory bulb; STR: striatum; TH: thalamus.

FIGS. 12*a-b* are schematic presentations of linkage analyses depicting the genotypes of two critical pedigrees with IBSN and demonstrating fine mapping of the IBSN candidate region. Black symbols in the pedigree represent affected individuals. The boxed regions indicate the homozygous regions in each affected individual. The polymorphic markers are shown on the left. Arrows indicate informative recombinations. Note that in family 1 the two affected individuals (individuals II2 and II3) share homozygosity in markers D19S867, D19S246, GDB:182452 and D19S553 and loss of homozygosity (i.e., heterozygosity) in marker rs8101959, thus defining the centromeric border of the candidate region distally to the SNP rs8101959 in the gene AP2A1 (FIG. 12*a*). On the other hand, in family 2 while the two affected individuals (individuals II4 and II7) share homozygosity in markers GDB:636554, D19S879, HRC.A, D19S604, GDB:181916, rs8101959, one of the affected individuals exhibit loss of homozygosity in marker D19S867, thus defining the telomeric border of the candidate region and placing the disease-causing gene proximal to the polymorphic marker D19S867 (FIG. 12*b*).

Figure 13:
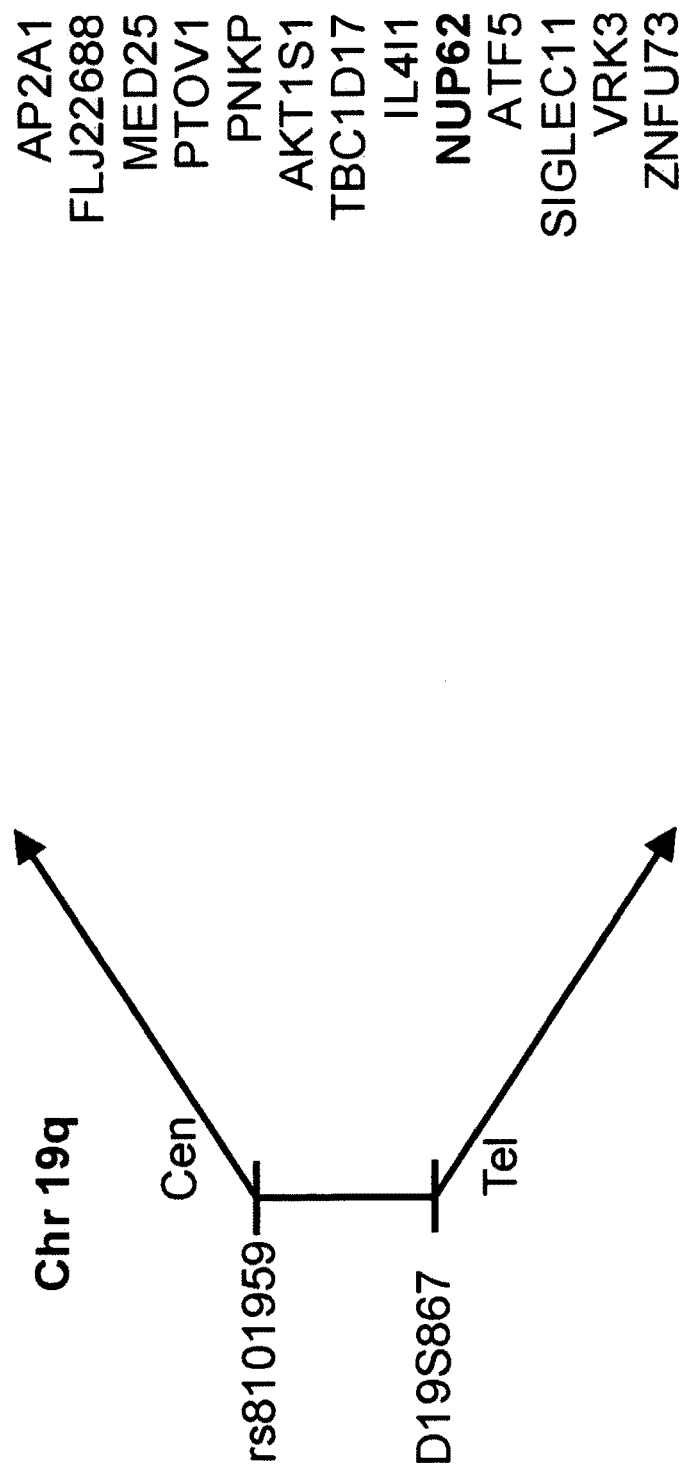

FIG. 13 is a diagram depicting the defined critical region of IBSN between markers rs8101959 and D19S867 on chromosome 19q with the included genes and their relative order: AP2A1 (GenBank Accession No. NM_1303787), FLJ22688 (GenBank Accession No. NM_025129), MED25 (GenBank Accession No. NM_030973), PTOV1 (GenBank Accession No. NP_059128), PNKP (GenBank Accession No. NM_007254), AKT1S1 (GenBank Accession No. NM_032375), TBC1D17 (GenBank Accession No. NM_024682), IL4I1 (GenBank Accession No. NM_172374), NUP62 (GenBank Accession No. NM_153719), ATF5 (GenBank Accession No. NM_012068), SIGLEC11 (GenBank Accession No. NM_052884), VRK3 (GenBank Accession No. NM_016440) and ZNF473 (GenBank Accession No. NM_015428). Cen—centromere; Tel—telomere.

FIGS. 14*a-b* are sequence analyses chromatograms from a wild-type (WT; FIG. 14*a*) and disease (M; FIG. 14*b*) genotypes performed using genomic DNA from control (i.e., unaffected with IBSN) and IBSN affected individual showing the missense mutation.

Figure 15A:
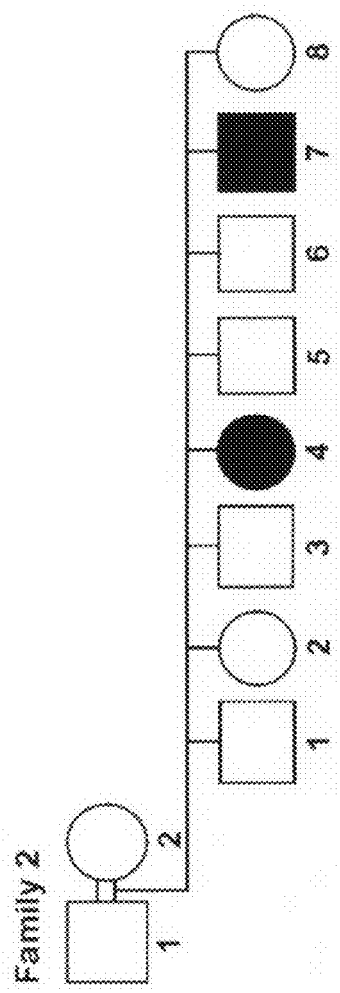
Figure 15B:
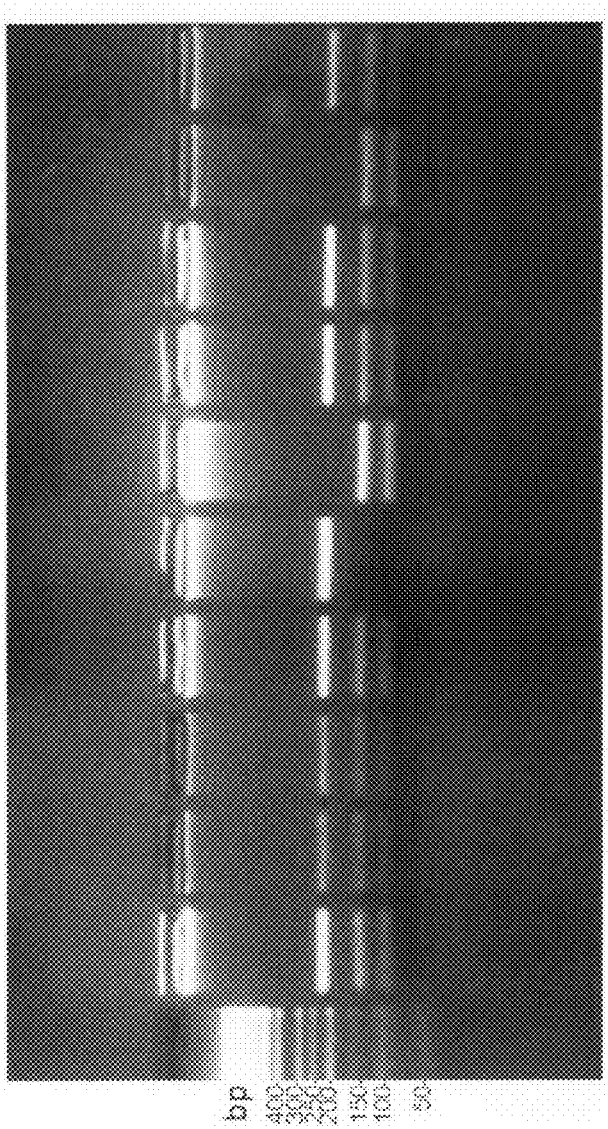

FIGS. 15*a-b* are a schematic presentation of a pedigree of Family 2 (FIG. 15*a*) and a PCR-RFLP analysis (FIG. 15*b*) depicting the segregation of the missense mutation in the nup62 gene in the affected families. Genomic DNA PCR amplification was performed with the forward primer A (SEQ ID NO:58) and reverse primer B (SEQ ID NO:59) PCR primers followed by digestion with the NciI restriction enzyme. Digestion of the PCR product representing the wild-type allele results in an uncut fragment of 208 bp and digestion of the PCR product representing mutant allele results in two fragments of 125 and 83 bp. Note that while the affected individuals (black symbols) are homozygotes to the missense mutation (individuals II4 and II7, lanes 6 and 9, respectively), all other family members, except for individual II3 (lane 5), are heterozygotes to the missense mutations (i.e., unaffected carriers; individuals I1, I2, II1, II2, II5, II6 and II8; lanes 1-4, 7-8 and 10). Individual 113 is unaffected and non-carrier of the missense mutation (lane 5).

Figure 16:
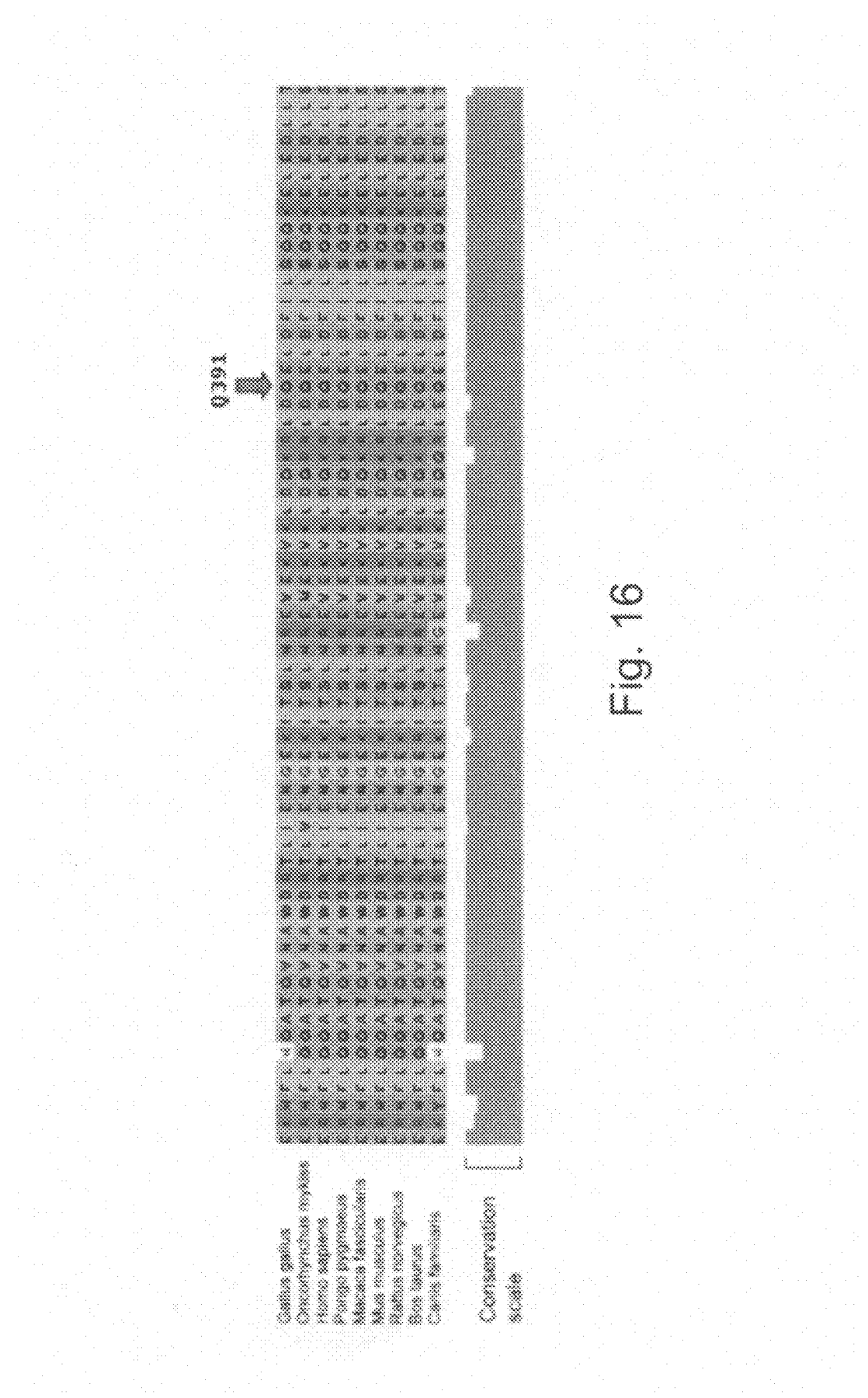

FIG. 16 is a multiple alignment and conservation analysis of human p62 with its orthologues. Multiple sequence alignment was performed by ClustalW, using 9 protein sequences of p62, including vertebrates from fish to human (*Homo sapiens*). *Gallus gallus* (chick; GenBank Accession No. XP_420179), *Oncorhynchus mykiss* (trout; GenBank Accession No. BAA24403), *homo sapiens* (GenBank Accession No. NP_036478), *Pongo pygmaeus* (orangutan; GenBank Accession No. CAH91435), *Macaca fascicularis* (crab-eating macaque; GenBank Accession No. BAE01812), *Mus musculus* (mouse; GenBank Accession No. Q63850), *Rattus norvegicus* (rat; GenBank Accession No. NP_075586); *Bos Taurus* (cow; GenBank Accession No. XP_615109). *Canis familiaris* (dog; GenBank Accession No. XP_852888). An especially conserved region was found between residues 330-459 (348 to 408 shown). Q391 in human is marked with a purple arrow. Residue colors represent amino acid biochemical properties according to Zappo colors. Conservation scale is shown below the alignment (purple).

Figure 17:
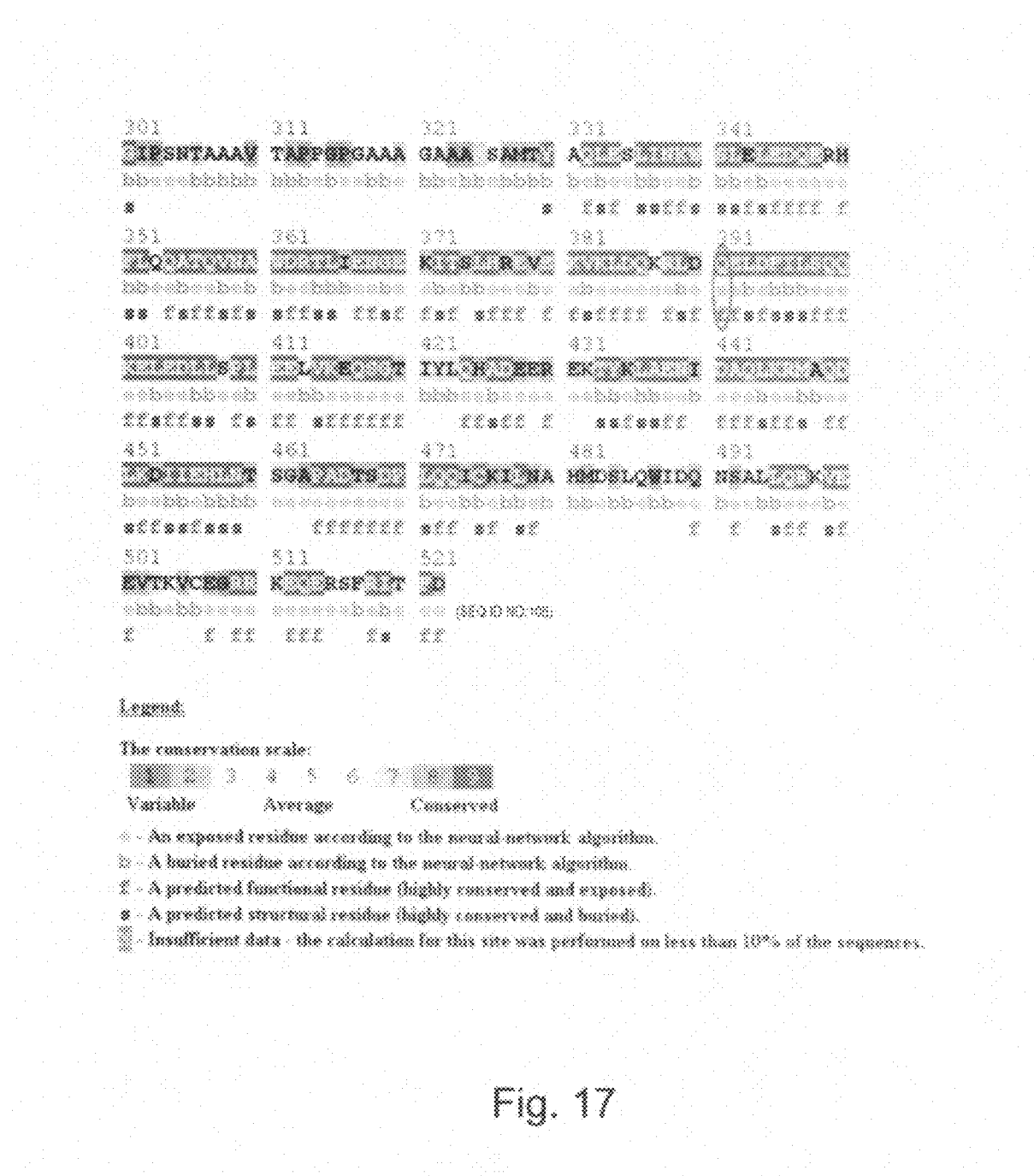

FIG. 17 is a diagram depicting conserved, exposed and functional predicted regions in the nup62 protein. Sequence conservation analysis was performed using ConSeq server. The results of the Multiple Sequence Alignment (MSA) shown in FIG. 16 served as an input. Presented are amino acid residues 301-521 of the MSA results. Results show the region containing the conserved domain (Nsp1_C domain), including residue Q391 (circled with red) that was found to be in the most conserved region. Most conserved regions are marked with dark magenta, and variable regions are marked with green. Exposed (e) and functional (f) predicted regions can be seen. "e"—an exposed residue according to the neural-network algorithm; "b"—a buried residue according to the neural-network algorithm; "f"—a predicted functional residue (highly conserved and exposed); "s"—a predicted structural residue (highly conserved and buried); "X" insufficient data—the calculation for this site was performed on less than 10% of the sequences.

Figures 18A, 18B:
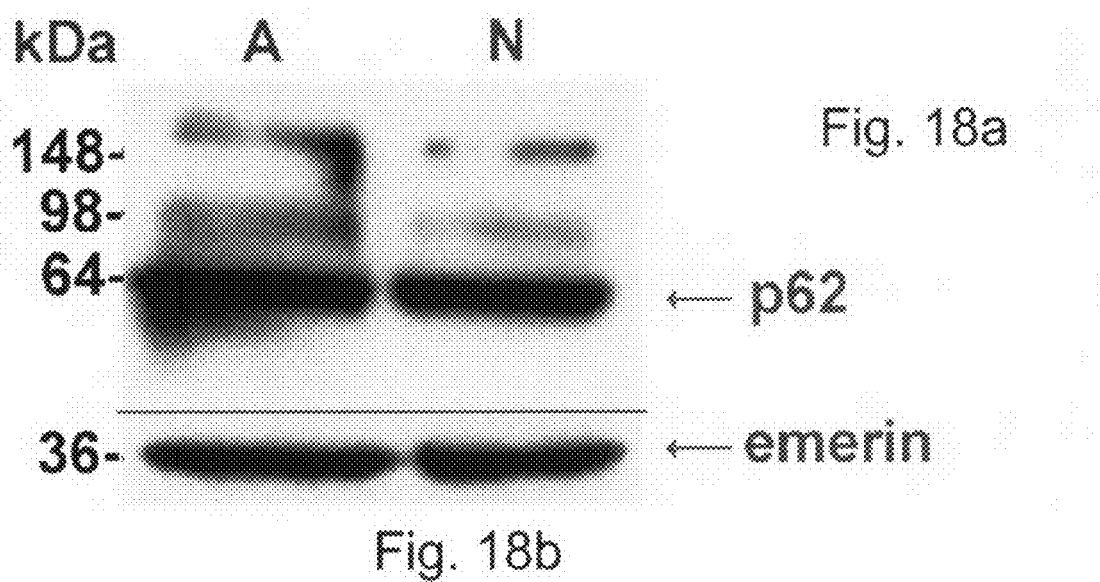

FIGS. 18a-b are Western blot analyses of p62 (FIG. 18a) or emerin (FIG. 18b) in the lymphoblasts of affected (A) and unaffected (normal; N) individuals. Note that no significant change in the expression pattern of p63 (nup62) is observed between the affected and unaffected individuals.

FIGS. 19a-f are immunofluorescence analyses of lymphoblastoid cells with p62 antibody from the affected (FIGS. 19a-c) and unaffected (normal; FIGS. 19d-f) individuals. Cells were stained with primary p62 antibody followed by secondary Cy3-conjugated antibody (red; FIGS. 19a and d). Nuclei were stained with DAPI (blue; FIGS. 19b and e) and merged images were formed (FIGS. 19c and f). Note that no significant difference is observed between lymphoblastoid cells derived from affected or unaffected individuals.

FIGS. 20a-f are confocal images of U2OS cells following transfection with mutated YFP-p62 and normal (wilt-type) YFP-p62 constructs. Cells transfected with mutated YFP-p62 (FIGS. 20a-c) or normal YFP-p62 (FIGS. 20d-f) constructs were stained with primary p62 antibody followed by secondary Cy3-conjugated antibody (red; FIGS. 20a and d). YFP-p62 construct fluorescence analysis was performed (green; FIGS. 20b and e) and merged images of Cy3, YFP and DAPI were formed (FIGS. 20c and f). Note that no significant difference is observed between U2OS cells transfected with mutated or wild-type YFP-p62 constructs.

DESCRIPTION OF THE PREFERRED EMBODIMENTS

The present invention is of methods and kits for diagnosing and treating pathologies associated with metal retardation. More specifically, the present invention relates to methods and kits for analyzing sequence alterations and expression levels of CC2D1A and nup62 for diagnosing and ultimately treating nonsyndromic mental retardation (NSMR) and/or infantile bilateral striatal necrosis (IBSN).

The principles and operation of the methods and kits according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The diagnosis of nonsyndromic mental retardation (NSMR) is currently performed using accepted intellectual tests and psychological evaluations. While a number of X-linked genes associated with NSMR have been identified, only two autosomal genes, the PRSS12 gene (GenBank Accession No. NP_003610) on chromosome 4q26 and the CRBN gene (GenBank Accession No. NP_057386) on chromosome 3p26, have been shown to cause autosomal recessive NSMR, each gene in only one family (1, 2). Thus, it is clear that multiple genetic components may play a role in the pathogenesis of NSMR and it is therefore desired to further decipher the entire genetic components causing mental retardation in order to enable accurate diagnosis, prenatal diagnosis and treatment.

In a linkage analysis study Basel-Vanagaite L., et al (3) mapped a candidate region for NSMR to an interval of 2.4 Mb on chromosome 19p13.12-p13.2. However, due to the relatively large size of the interval, it was difficult to predict which of the multiple genes reside in this interval is involved with NSMR.

Infantile bilateral striatal necrosis (IBSN) is a neurological disorder involved with developmental regression, choreoathetosis, dystonia, spasticity, dysphagia, failure to thrive, nystagmus, optic atrophy, and mental retardation. Familial IBSN has been reported, suggesting the presence of an autosomal recessive mode of inheritance. In families with mitochondrial inheritance, mutations in the adenosine triphosphatase 6 gene (complex V) have been described (5, 6).

Straussberg R et al., mapped a candidate region for autosomal recessive IBSN to an interval of 1.2 Mb chromosomal region on chromosome 19q13.32-13.41 (7, 8). However, to date, no specific gene from this interval has been identified as directly involved in IBSN.

While reducing the present invention to practice, the present inventors have uncovered that autosomal recessive nonsyndromic mental retardation (NSMR) is caused by mutations in a novel gene CC2D1A, a member of a previously uncharacterized gene family, encoding a putative NF-κB activating protein.

As is shown in FIGS. 3a-b, 4a-b, 6a-b and is described in Example 1 of the Examples section which follows, a disease-causing deletion mutation was identified in NSMR affected individuals (which are homozygotes to the deleted allele) and in unaffected carriers (which are heterozygotes to the deleted allele). The deletion mutation encompasses SEQ ID NO:109, (nucleotides 13891337-13894926 of the genomic sequence of CC2D1A as set forth by GenBank Accession No. NC_000019.8) and results in deletion of exons 14, 15 and 16 of wild-type CC2D1A mRNA (GenBank Accession No. NM_017721.3; SEQ ID NO:1) which when translated results in a truncated polypeptide of 85 kDa (as set forth by SEQ ID NO:5) due to a frame shift at amino acid 410 of wild-type CC2D1A (GenBank Accession No. NP_060191) which leads to early termination at amino acid 438. In addition, as is further shown in FIGS. 11a-d and is described in Example 2 of the Examples section which follows, the CC2D1A mRNA is expressed in the embryonic ventricular zone and developing cortical plate, persisting into adulthood with highest expression in the cerebral cortex and hippocampus. This suggests that a previously unknown signal transduction pathway is important in human cognitive development. Altogether, these findings demonstrate, for the first time, that mutations in the CC2D1A are associated with NSMR and suggest using sequence analysis of the CC2D1A gene and/or detection of decreased CC2D1A expression level for the diagnosis of NSMR.

Thus, according to one aspect of the present invention there is provided a method of diagnosing non-syndromic mental retardation (NSMR) in an individual. The method is effected by analyzing a sequence of a CC2D1A of the individual, wherein an alteration in the sequence resulting in downregulation of an expression level and/or activity of the CC2D1A is indicative of the non-syndromic mental retardation, thereby diagnosing the non-syndromic mental retardation in the individual.

As used herein the term "diagnosing" refers to determining presence or absence of a pathology, classifying a pathology or a symptom, determining a severity of the pathology, monitoring pathology progression, forecasting an outcome of a pathology and/or prospects of recovery.

Preferably, the term "diagnosing" further includes determining carrier status of the pathology, i.e., identifying an individual who is at risk of having an affected offspring. The term "detecting" may also optionally encompass any of the above when used in prenatal testing of a conceptus (prenatal diagnosis).

The term "pathology" refers to any deviation from a healthy or normal condition, such as a disease, disorder or any abnormal medical condition. Preferably, the term pathology as used herein refers to a disease, disorder or syndrome associated with mental retardation such as NSMR or IBSN as is further described hereinbelow.

As used herein the phrase "non-syndromic mental retardation (NSMR)" refers to a condition of mental retardation in an individual which do not have major physical abnormalities, dysmorphism or neurological abnormalities. Preferably, the phrase NSMR refers to the autosomal recessive mode of inheritance of NSMR which may account for nearly a quarter of all individuals with NSMR.

The term "individual" (or "subject" which is interchangeably used herein) encompasses a human being of any sex who is at risk of developing the pathology or is affected with the pathology. The term "individual" also encompasses a conceptus, i.e., the product of conception at any point between fertilization and birth. The term "conceptus" includes an embryo, a fetus or an extraembryonic membrane of an ongoing pregnancy as well as of a terminated pregnancy (e.g., following miscarriage, abortion or delivery of a dead fetus). For example, an individual who is at risk of developing NSMR is an offspring of two carriers of either the same or two different NSMR disease-causing-mutations.

The method according to this aspect of the present invention is effected by analyzing the sequence of a CC2D1A of the individual. The phrase "analyzing a sequence" refers to determining a presence, absence or sequence (e.g., order of appearance) of specific nucleic acids or amino acids of the individual. It will be appreciated that sequence analysis can be performed at the genomic level (e.g., using genomic DNA molecules), at the transcript level (e.g., using RNA or mRNA molecules) or at the protein level (e.g., using Edman's degradation). Methods of analyzing sequences are well known in the art and are further described hereinunder.

The term "CC2D1A" refers to the coiled-coil and C2 domain containing 1A protein. CC2D1A belongs to a protein family which carries two conserved motifs: the C2 and DM14 domains (see FIGS. 5, 8, 9a-b and Examples 1 and 2 of the Examples section which follows). The human CC2D1A is set forth by SEQ ID NO:4 (GenBank Accession No. NP_060191) and is encoded by the mRNA sequence set forth by SEQ ID NO:1 (GenBank Accession No. NM_017721.3). CC2D1A was originally identified as a putative signal transducer participating in positive regulation of I-κB kinase/NF-κB cascade (A. Matsuda et al., 2003, Oncogene 22: 3307). The mouse homologue of the CC2D1A protein is the Freud-1 protein (GenBank Accession No. ABC56419) which is known to be a repressor of serotonin 5-HT1A receptor gene (Ou X-M., et al., 2003, J. Neuroscience, 23: 7415-7425).

The phrase "CC2D1A of the individual" refers to the CC2D1A nucleic acid or amino acid sequence which is present in a cell of the individual. Such a cell can be derived from any biological sample obtained from the individual and can also be part of the individual (i.e., in vivo diagnosis). As used herein "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, sputum, milk, blood cells, tumors, neuronal tissue, organs, and also samples of in vivo cell culture constituents.

Thus, identification of a sequence alteration in the CC2D1A nucleic acid sequence (DNA or RNA) and/or amino acid sequence (protein) which results in downregulating of an expression level and/or activity of the CC2D1A is indicative of the diagnosis of NSMR in the individual. Such a sequence alteration, which is also referred to herein as a "disease-causing-mutation" (i.e., a sequence alteration which causes the pathology) can be for example, a missense mutation (i.e., a mutation which results in an amino acid change, a nonsense mutation (i.e., a mutation which introduces a stop codon in a protein), a frameshift mutation [i.e., a mutation, usually, deletion or insertion of nucleic acids which changes the reading frame of the protein, and may result in an early termination or in a longer amino acid sequence], a readthrough mutation (i.e., a mutation which results in an elongated protein due to a change in a coding frame or a modified stop codon), a promoter mutation (i.e., a mutation in a promoter sequence, usually 5' to the transcription start site of a gene, which results in up-regulation or down-regulation of a specific gene product), a regulatory mutation (i.e., a mutation in a region upstream or downstream, or within a gene, which affects the expression of the gene product), a deletion [i.e., a mutation which deletes coding or non-coding nucleic acids in a gene sequence, e.g., deletion of nucleic acids 13891337-13894926 of the genomic sequence of CC2D1A as set forth by GenBank Accession No. NC_000019.8], an insertion (i.e., a mutation which inserts coding or non-coding nucleic acids into a gene sequence), an inversion (i.e., a mutation which results in an inverted coding or non-coding sequence), a splice mutation (i.e., a mutation which results in abnormal splicing or poor splicing) and a duplication (i.e., a mutation which results in a duplicated coding or non-coding sequence).

Any of the abovedescribed sequence alterations can be in a homozygote form (i.e., in this case both CC2D1A alleles of the individual include the same disease-causing-mutation) or in a heterozygote form (i.e., only one CC2D1A allele of the individual carries the disease-causing-mutation). It will be appreciated that since abnormal CC2D1A causes autosomal recessive NSMR, individuals who are homozygote to the same disease-causing-mutation or individuals who exhibit two different disease-causing-mutations, one on each CC2D1A allele (i.e., one inherited from the paternal chromosome and one inherited from the maternal chromosome) will be affected with the NSMR On the other hand, individuals who carry only one disease-causing-mutation on one allele, while the other allele is devoid of any disease-causing-mutation (also referred to as a wild-type allele) are healthy carriers of a pathological mutation in NSMR and thus are at risk of having an affected offspring.

Preferably, sequence analysis of CC2D1A is performed using an isolated nucleic acid sequence capable of specifically hybridizing to a mutated CC2D1A and not to a wild-type CC2D1A nucleic acid sequence.

As used herein the phrase "mutated CC2D1A nucleic acid sequence" refers to a CC2D1A nucleic acid sequence (e.g., DNA or RNA) which includes at least one sequence alteration as described hereinabove. Such a mutated CC2D1A can encode an altered CC2D1A amino acid sequence (e.g., a nonsense mutation or a missense mutation) and/or can result in downregulation of the expression level and/or activity of the CC2D1A in cells of the individual (e.g., in neuronal cells in the brain). Accordingly, the phrase "wild-type nucleic acid sequence" refers to a CC2D1A nucleic acid sequence (e.g., DNA or RNA) which is devoid of any disease-causing-mutation as described hereinabove. Preferably, the wild-type CC2D1A genomic sequence is as set forth by nucleotides 13864993-13902692 of GenBank Accession No. NC_000019.8 and the wild-type CC2D1A mRNA sequence is as set forth by GenBank Accession No. NM_017721.3.

The isolated nucleic acid sequence of the present invention can be any single stranded or double stranded oligomer or polymer of ribonucleic acid (RNA) or deoxyribonucleic acid (DNA) or mimetics thereof capable of specifically hybridizing to a mutated and not to a wild-type CC2D1A nucleic acid sequence. Methods of qualifying such differential hybridization are well known in the art and are further described hereinunder.

The term "isolated nucleic acid sequence" includes oligonucleotides composed of naturally-occurring bases, sugars and covalent internucleoside linkages (e.g., backbone) as well as oligonucleotides having non-naturally-occurring portions which function similarly to respective naturally-occurring portions.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

Specific examples of preferred oligonucleotides useful according to this aspect of the present invention include oligonucleotides containing modified backbones (e.g., those that retain a phosphorus atom in the backbone) or non-natural internucleoside linkages, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C). Further base modifications include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

It will be appreciated that the isolated nucleic acid sequence of the present invention can be of any size, e.g., from 10-40 nucleic acids to about 100-300 nucleic acids or even 1000-3000 nucleic acids in length.

Preferably, for the specific hybridization of the isolated nucleic acid sequence with a mutated and not a wild-type CC2D1A, the isolated nucleic acid sequence is of at least 10, at least 11, at least 12, at least 13, at least 14, at least 15, at least 16, at least 18, at least 19, at least 20, at least 21, at least 22, at least 23, at least 24, at least 25, at least 30 or at least 40, bases specifically hybridizable with a mutated and not a wild-type nucleic acid sequence as described hereinabove.

It will be appreciated that for certain detection methods (e.g., an oligonucleotide microarray as is further described hereinbelow), the isolated nucleic acid sequence of the present invention is preferably bound to a solid support, such as a solid surface (e.g., a glass wafer) as is further described hereinunder. Usually the solid support is a microsphere (bead), a magnetic bead, a nitrocellulose membrane, a nylon membrane, a glass slide, a fused silica (quartz) slide, a gold film, a polypyrrole film, an optical fiber and/or a microplate well.

As is further described hereinunder, the isolated nucleic acid sequence of the present invention can be labeled. Various methods can be used to label the isolated nucleic acid sequence of the present invention. These include fluorescent labeling with a fluorophore conjugated via a linker or a chemical bond to at least one nucleotide, or the use of a covalently conjugated enzyme (e.g., Horse Radish Peroxidase) and a suitable substrate (e.g., o-phenylenediamine) which upon interaction therebetween yields a colorimetric or fluorescent color. Thus, the isolated nucleic acid sequence can be radiolabeled, Digoxigenin labeled and/or biotinylated.

Preferably, sequence analysis of CC2D1A amino acid sequence is performed using an antibody or antibody fragment which comprises an antigen recognition region capable of specifically binding to a mutated CC2D1A and not to a wild-type CC2D1A amino acid sequence.

The phrase "mutated CC2D1A amino acid sequence" refers to a CC2D1A amino acid sequence which includes a sequence alteration resulting, when present in cells of the individual, in downregulated expression level and/or activity of CC2D1A, and/or leading to, in a homozygote or a compound heterozygote form, to NSMR in the individual. A non-limiting example of a mutated CC2D1A amino acid sequence is provide in SEQ ID NO:5, as found in the affected individuals of NSMR families 1-9. Accordingly, the phrase "wild-type amino acid sequence" refers to a CC2D1A amino acid sequence (e.g., protein) which is devoid of any disease-causing-mutation as described hereinabove.

The term "antibody" as used in this invention includes intact antibody molecules as well as functional fragments thereof, such as Fab, F(ab')2, Fv or single domain molecules such as VH and VL to an epitope of an antigen. As used herein, the term "epitope" refers to any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics. The functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; and (6) Single domain antibodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

It will be appreciated that for certain detection methods as described hereinunder, the antibody or antibody fragment is bound to a solid support (such as nylon filters, glass slides or silicon chips) using methods which are well known in the art.

Preferably, for detecting the mutated CC2D1A nucleic acid sequence the antibody or antibody fragment is labeled (e.g., radiolabeled, biotinylated or fluorescent labeling) using methods known in the art.

As is shown in FIGS. 6a-b and is described in Example 1 of the Examples section which follows, the deletion of nucleic acids 13891337-13894926 of CC2D1A as set forth by GenBank Accession No. NC_000019.8 which was found in all NSMR affected individuals of the NSMR Families 1-9 of the present study resulted in a truncated CC2D1A polypeptide as set forth by SEQ ID NO:5. Thus, it will be appreciated that diagnosis of NSMR can be also performed by detecting the expression level of the CC2D1A.

As used herein the phrase "expression level of CC2D1A" refers to the level of the CC2D1A mRNA as set forth by SEQ ID NO:1 and/or the full length CC2D1A protein as set forth by SEQ ID NO:4 (GenBank Accession NO. NP_060191). Preferably, detection of the expression level of CC2D1A also refers to the level of the functional CC2D1A polypeptide which activity involves in positive regulation of the I-κB kinase/NF-κB cascade (A. Matsuda et al., Oncogene 22, 3307, 2003) and/or regulation of transcription of the of serotonin 5-HT1A receptor gene (Ou X-M., et al., 2003, J. Neuroscience, 23: 7415-7425). Methods of detecting the functional activity of CC2D1A include a reporter gene (e.g., luciferase) transcriptional activity assay using the novel DNA repressor element of the 5-HT1A receptor gene essentially as described in Ou X-M., et al., 2003, J. Neuroscience, 23: 7415-7425, which is fully incorporated herein by reference.

Thus, according to the method of this aspect of the present invention a decrease in the expression level of CC2D1A of the individual as compared to that of an unaffected individual [i.e., an individual who is not affected with the pathology (NSMR in this case) and/or is not a carrier of a disease-causing-mutation in the gene causing the pathology (CC2D1A in this case)] is indicative of the diagnosis of NSMR. Methods of detecting the expression level of a protein and comparing such expression level to that of unaffected (control) individuals include, for example, Western blot analysis, immunohistochemistry, immunofluorescence, radio immuno assay and FACS analysis as is further described hereinunder and in the Examples section which follows. Methods of detecting the expression level of RNA (e.g., mRNA) and comparing such expression level to that of unaffected (control) individuals include, for example, Northern blot analysis, RT-PCR, RNA in situ hybridization, in situ RT-PCR and RNA microarrays.

While further reducing the present invention to practice, the present inventors have uncovered that the autosomal recessive infantile bilateral striatal necrosis (IBSN) is caused by mutations in the nup62 gene encoding a nuclear pore complex protein.

As is shown in FIGS. 14a-b and 15a-b and is described in Example 3 of the Examples section which follows, a missense mutation 1429A→C in the mRNA encoding nup62 (as set forth by SEQ ID NO:68; GenBank Accession No. NM_012346) which results in the Q391P amino acid substitution in the nup62 protein (GenBank Accession No. NP_036478; SEQ ID NO:69) was present in IBSN affected individuals but not in healthy, unaffected and non-carrier control individuals. This missense mutation involves a substitution from a polar, hydrophilic residue (Q) to a non-polar, neutral residue (P). As is further shown in FIGS. 16 and 17 and is described in Example 6 of the Examples section which follows, bioinformatics analyses involving comparisons of p62 protein sequences from diverse species indicate that the glutamine residue at position 391 is highly conserved and that the Q391P substitution is likely to hamper the functional activity of the nup62 protein. In addition, as described in Example 4 of the Examples section which follows, identification of the Q391P mutation in the nup62 protein enabled successful prenatal diagnoses of five conceptuses in three at-risk families. Altogether, these findings suggest that p62 has a cell type-specific role and is important in the degeneration of the basal ganglia in humans and suggest sequence analysis for diagnosing IBSN.

Thus, according to another aspect of the present invention there is provided a method of diagnosing infantile bilateral striatal necrosis (IBSN) in an individual. The method is effected by analyzing a sequence of a nup62 of the individual, wherein an alteration in the sequence resulting in downregulation of an expression level and/or activity of the nup62 is indicative of the non-syndromic mental retardation, thereby diagnosing the infantile bilateral striatal necrosis in the individual.

As used herein the phrase "infantile bilateral striatal necrosis" refers to a neurological disorder characterized by symmetrical degeneration of the caudate nucleus, putamen, and occasionally the globus pallidus, with little involvement of the rest of the brain [MIM 271930]. The clinical features of IBSN include developmental regression, choreoathetosis, dystonia, spasticity, dysphagia, failure to thrive, nystagmus, optic atrophy, and mental retardation.

The term "nup62" as used herein refers to the genomic and/or RNA sequence encoding nucleoporin 62 kDa (p62; also known as MGC841; FLJ20822; FLJ43869; DKFZp547L134) which is a member of the FG-repeat containing nucleoporins and is localized to the nuclear pore central plug. The nup62 gene product, p62 protein, associates with the importin alpha/beta complex which is involved in the import of proteins containing nuclear localization signals. Nucleoporins are the main components of the nuclear pore complex in eukaryotic cells which extends across the nuclear envelope, forming a gateway that regulates the flow of macromolecules between the nucleus and the cytoplasm. The human nup62 gene product (p62 protein) is set forth by SEQ ID NO:69 (GenBank Accession No. NP_036478) and is encoded by the nucleic acid sequence set forth by SEQ ID NO:68 (GenBank Accession No. NM_012346).

Thus, the method according to this aspect of the present invention is effected by analyzing the sequence of nup62 using, for example, an isolated nucleic acid sequence capable of specifically hybridizing to a mutated nup62 and not to a wild-type nup62 nucleic acid sequence. A non-limiting example of a mutated nup62 nucleic acid sequence is a nup62 nucleic acid sequence which includes a cytosine nucleotide at position 1429 of the sequence set forth by SEQ ID NO:68.

Alternatively, analyzing the sequence of the nup62 gene product (p62) can be performed using an antibody or antibody fragment capable of specifically binding to a mutated nup62 (p62) and not to a wild-type nup62 (p62) amino acid sequence. A non-limiting example of a mutated nup62 (p62) amino acid sequence is a nup62 (p62) amino acid sequence which includes a proline residue at position 391 of the sequence set forth by SEQ ID NO:69.

It should be noted that certain sequence alterations in the nup62 gene are likely to result in downregulation of the expression level of the nup62 gene product (p62 protein).

Thus, according to one preferred embodiment of the present invention, diagnosing of IBSN is effected by detecting an expression level of a nup62 gene product (p62) of cells of the individual. Non-limiting examples of methods which can be used to detect the expression level of nup62 gene product (p62) include Western blot analysis, immunohistochemistry, immunofluorescence, radio immuno assay and FACS analysis as is further described hereinunder and in the Examples section which follows.

Thus, the teachings of the present invention can be used to diagnose a pathology associated with mental retardation in an individual. As used herein the phrase "pathology associated with mental retardation" refers to any disease, disorder, syndrome or condition which is associated, caused by or resulting in mental retardation. Non-limiting examples for such a pathology include NSMR and IBSN. Diagnosing mental retardation according to the method of this aspect of the present invention can be performed by analyzing the sequence of CC2D1A and/or nup62 of the individual wherein an alteration in the sequence which results in downregulation of an expression level and/or activity of CC2D1A or nup62 gene product (p62) is indicative of a pathology associated with mental retardation. Additionally or alternatively, diagnosis of mental retardation according to the method of this aspect of the present invention can be performed by detecting the expression level of CC2D1A and/or nup62 gene product (p62) in cells of the individual, wherein a decrease in the expression level as compared to the expression level in an unaffected individual is indicative of the pathology associated with mental retardation in the individual.

The present invention further contemplates the generation and use of an addressable DNA chip (microarray) for diagnosing the pathology associated with mental retardation in an individual.

Thus, according to another aspect of the present invention there is provided an addressable oligonucleotide array comprising no more than 5000 oligonucleotides, wherein at least one of the oligonucleotides is capable of specifically hybridizing to a mutated CC2D1A and not to a wild-type CC2D1A nucleic acid sequence and at least a second oligonucleotide of the oligonucleotides is capable of specifically hybridizing to a mutated nup62 and not to a wild-type nup62 nucleic acid sequence.

Preferably, the addressable oligonucleotide array includes at least 2 and no more than 5000 oligonucleotides, at least 3 and no more than 4000 oligonucleotides, at least 4 and no more than 3000 oligonucleotides, at least 6 and no more than 2000 oligonucleotides.

Preferably, each of the oligonucleotides of the addressable oligonucleotide array is of at least 10 and no more than 40 nucleic acids, at least 11 and no more than 35, at least 12 and no more than 30, even more preferably, at least 15 and no more than 25 nucleic acids in length.

The addressable oligonucleotide array can be generated by attaching the oligonucleotides (e.g., the isolated nucleic acids described hereinabove) to a solid support using methods known in the arts (see for example, U.S. Pat. Nos. 5,445,934, 5,744,305, 5,700,637, 5,807,522 and WO Pat No. WO 98/18961). Briefly, the isolated nucleic acid sequence (e.g., oligonucleotide) is synthesized on or spotted and then immobilized to a predefined region of a chip solid phase (substrate). For example, a DNA fragment is physically spotted using a pin tip onto a solid phase substrate such as a slide glass which has been subjected to special processing such as poly-L-lysine-coating or silanization. Prior to application of the isolated nucleic acid sequence to the solid support, the isolated nucleic acid sequence is preferably modified to facilitate fixation to the solid support. Such modifications may encompass homopolymer tailing, coupling with different reactive groups such as aliphatic groups, $NH_2$ groups, SH groups, carboxylic groups, or coupling with biotin, digoxigenin or haptens.

As described hereinabove, the nucleic acid alteration of the present invention can be identified using a variety of approaches. One option is to determine the entire gene sequence of a PCR reaction product. Alternatively, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

Following is a non-limiting list of methods which can be used to identify the nucleic acid alterations in the CC2D1A and/or nup62 genes.

Direct sequencing of a PCR product is based on the amplification of a genomic sequence using specific PCR primers in a PCR reaction following by a sequencing reaction utilizing the sequence of one of the PCR primers as a sequencing primer. Sequencing reaction can be performed using, for example, the Applied Biosystems (Foster City, Calif.) ABI PRISM® BigDye™ Primer or BigDye™ Terminator Cycle Sequencing Kits.

Restriction fragment length polymorphism (RFLP) uses a change in a single nucleotide (the SNP nucleotide) which modifies a recognition site for a restriction enzyme resulting in the creation or destruction of an RFLP.

For example, RFLP can be used to detect the Q391P missense mutation in the nup62 gene product (p62 protein) (SEQ ID NO:69) (A→C substitution at nucleotide 1429 as set forth in SEQ ID NO:68) in a genomic DNA of an individual. Briefly, genomic DNA is amplified using primer A (SEQ ID NO:64) and primer B (SEQ ID NO:65) PCR primers, and the resultant PCR product is subjected to digestion using a restriction enzyme such as NciI (see e.g., FIG. 15b) which is capable of differentially digesting a PCR product containing the C allele (and not the A allele) at position 1429 of SEQ ID NO:68.

Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807-6817, 1990). However, this method requires the use of osmium tetroxide and piperidine, two highly noxious chemicals which are not suited for use in a clinical laboratory.

Differential PCR amplification of a nucleic acid sequence encompassing a large deletion. In this techniques two PCR primers are designed from outside the deletion boundaries such that the predicted PCR product is expected to form only in genomes having the deleted allele (i.e., the allele with the large deletion). On the other hand, due to the size of the deletion (e.g., more than 3000 bp), PCR amplification of a wild-type allele is unfavoured. As a control, one internal primer (from inside of the deletion boundary) is preferably employed along with one external primer (from outside of the deletion boundary). For example, in order to detect the CC2D1A deletion of nucleic acids 13864993-13902692 of GenBank accession No. NC_000019.8, the following primers were designed and successfully used (data not shown). For the mutant allele (carrying the deletion) the forward 5'-gggagcttgacattggacat (SEQ ID NO:100) and reverse 5'-ggggtaaggaggacaagcag (SEQ ID NO:101) PCR primers were employed and resulted in a PCR product of 313 bp. For the normal allele (devoid of the deletion) the forward 5'-ttggtctccatcctgacaca (SEQ ID NO:102) and reverse 5'-tcccaaagtgctgggactac (SEQ ID NO:103) PCR primers were employed and resulted in a PCR product of 240 bp. PCR amplification conditions were essentially as described in Table 1, hereinbelow, except that annealing was at 64° C.-1° C. for 9 cycles (i.e., starting at 64° C., and reducing annealing temperature in 1° C. at each cycle, for a total of 9 cycles, following by 26 cycles with annealing temperature of 55° C.

Allele specific oligonucleotide (ASO) is designed to hybridize in proximity to the polymorphic nucleotide, such that a primer extension or ligation event can be used as the indicator of a match or a mis-match. Hybridization with radioactively labeled allelic specific oligonucleotides (ASO) also has been applied to the detection of specific SNPs (Conner et al., Proc. Natl. Acad. Sci., 80:278-282, 1983). The method is based on the differences in the melting temperature of short DNA fragments differing by a single nucleotide. Stringent hybridization and washing conditions can differentiate between mutant and wild-type alleles.

Denaturing/Temperature Gradient Gel Electrophoresis (DGGE/TGGE): Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of SNPs in the target sequences because of the corresponding changes in their electrophoretic mobilities. The fragments to be analyzed, usually PCR products, are "clamped" at one end by a long stretch of G-C base pairs (30-80) to allow complete denaturation of the sequence of interest without complete dissociation of the strands. The attachment of a GC "clamp" to the DNA fragments increases the fraction of mutations that can be recognized by DGGE (Abrams et al., Genomics 7:463-475, 1990). Attaching a GC clamp to one primer is critical to ensure that the amplified sequence has a low dissociation temperature (Sheffield et al., Proc. Natl. Acad. Sci., 86:232-236, 1989; and Lerman and Silverstein, Meth. Enzymol., 155:482-501, 1987). Modifications of the technique have been developed, using temperature gradients (Wartell et al., Nucl. Acids Res., 18:2699-2701, 1990), and the method can be also applied to RNA:RNA duplexes (Smith et al., Genomics 3:217-223, 1988).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405, 1991). CDGE requires that gels be performed under different denaturant conditions in order to reach high efficiency for the detection of SNPs.

A technique analogous to DGGE, termed temperature gradient gel electrophoresis (TGGE), uses a thermal gradient rather than a chemical denaturant gradient (Scholz, et al., Hum. Mol. Genet. 2:2155, 1993). TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Another common method, called "Single-Strand Conformation Polymorphism" (SSCP) was developed by Hayashi, Sekya and colleagues (reviewed by Hayashi, PCR Meth. Appl., 1:34-38, 1991) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874-879, 1989).

The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

Dideoxy fingerprinting (ddF) is another technique developed to scan genes for the presence of mutations (Liu and Sommer, PCR Methods Appli., 4:97, 1994). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200-300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion sub-cloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

Pyrosequencing™ analysis (Pyrosequencing, Inc. Westborough, Mass., USA) is based on the hybridization of a sequencing primer to a single stranded, PCR-amplified, DNA template in the presence of DNA polymerase, ATP sulfurylase, luciferase and apyrase enzymes and the adenosine 5' phosphosulfate (APS) and luciferin substrates. In the second step the first of four deoxynucleotide triphosphates (dNTP) is added to the reaction and the DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. In the last step the ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a pyrogram™. Each light signal is proportional to the number of nucleotides incorporated.

Acycloprime™ analysis (Perkin Elmer, Boston, Mass., USA) is based on fluorescent polarization (FP) detection. Following PCR amplification of the sequence containing the SNP of interest, excess primer and dNTPs are removed through incubation with shrimp alkaline phosphatase (SAP) and exonuclease I. Once the enzymes are heat inactivated, the Acycloprime-FP process uses a thermostable polymerase to add one of two fluorescent terminators to a primer that ends immediately upstream of the SNP site. The terminator(s) added are identified by their increased FP and represent the allele(s) present in the original DNA sample. The Acycloprime process uses AcycloPol™, a novel mutant thermostable polymerase from the Archeon family, and a pair of AcycloTerminators™ labeled with R110 and TAMRA, representing the possible alleles for the SNP of interest. AcycloTerminator™ non-nucleotide analogs are biologically active with a variety of DNA polymerases. Similarly to 2',3'-dideoxynucleotide-5'-triphosphates, the acyclic analogs function as chain terminators. The analog is incorporated by the DNA polymerase in a base-specific manner onto the 3'-end of the DNA chain, and since there is no 3'-hydroxyl, is unable to function in further chain elongation. It has been found that AcycloPol has a higher affinity and specificity for derivatized AcycloTerminators than various Taq mutant have for derivatized 2',3'-dideoxynucleotide terminators.

Reverse dot blot uses labeled sequence specific oligonucleotide probes and unlabeled nucleic acid samples. Activated primary amine-conjugated oligonucleotides are covalently attached to carboxylated nylon membranes. After hybridization and washing, the labeled probe, or a labeled fragment of the probe, can be released using oligomer restriction, i.e., the digestion of the duplex hybrid with a restriction enzyme. Circular spots or lines are visualized colorimetrically after hybridization through the use of streptavidin horseradish peroxidase incubation followed by development using tetramethylbenzidine and hydrogen peroxide, or via chemiluminescence after incubation with avidin alkaline phosphatase conjugate and a luminous substrate susceptible to enzyme activation, such as CSPD, followed by exposure to x-ray film.

It will be appreciated that advances in the field of SNP detection have provided additional accurate, easy, and inexpensive large-scale SNP genotyping techniques, such as dynamic allele-specific hybridization (DASH, Howell, W. M. et al., 1999. Dynamic allele-specific hybridization (DASH). Nat. Biotechnol. 17: 87-8), microplate array diagonal gel electrophoresis [MADGE, Day, I. N. et al., 1995. High-throughput genotyping using horizontal polyacrylamide gels with wells arranged for microplate array diagonal gel electrophoresis (MADGE). Biotechniques. 19: 830-5], the TaqMan system (Holland, P. M. et al., 1991. Detection of specific polymerase chain reaction product by utilizing the 5'→3' exonuclease activity of *Thermus aquaticus* DNA polymerase. Proc Natl Acad Sci USA. 88: 7276-80), as well as various DNA "chip" technologies such as the GeneChip microarrays (e.g., Affymetrix SNP chips) which are disclosed in U.S. Pat. No. 6,300,063 to Lipshutz, et al. 2001, which is fully incorporated herein by reference, Genetic Bit Analysis (GBA™) which is described by Goelet, P. et al. (PCT Appl. No. 92/15712), peptide nucleic acid (PNA, Ren B, et al., 2004. Nucleic Acids Res. 32: e42) and locked nucleic acids (LNA, Latorra D, et al., 2003. Hum. Mutat. 22: 79-85) probes, Molecular Beacons (Abravaya K, et al., 2003. Clin Chem Lab Med. 41: 468-74), intercalating dye [Germer, S. and Higuchi, R. Single-tube genotyping without oligonucleotide probes. Genome Res. 9:72-78 (1999)], FRET primers (Solinas A et al., 2001. Nucleic Acids Res. 29: E96), AlphaScreen (Beaudet L, et al., Genome Res. 2001, 11(4): 600-8), SNPstream (Bell P A, et al., 2002. Biotechniques. Suppl.: 70-2, 74, 76-7), Multiplex minisequencing (Curcio M, et al., 2002. Electrophoresis. 23: 1467-72), SnaPshot (Turner D, et al., 2002. Hum Immunol. 63: 508-13), MassEXTEND (Cashman J R, et al., 2001. Drug Metab Dispos. 29: 1629-37), GOOD assay (Sauer S, and Gut I G. 2003. Rapid Commun. Mass. Spectrom. 17: 1265-72), Microarray minisequencing (Liljedahl U, et al., 2003. Pharmacogenetics. 13: 7-17), arrayed primer extension (APEX) (Tonisson N, et al., 2000. Clin. Chem. Lab. Med. 38: 165-70), Microarray primer extension (O'Meara D, et al., 2002. Nucleic Acids Res. 30: e75), Tag arrays (Fan J B, et al., 2000. Genome Res. 10: 853-60), Template-directed incorporation (TDI) (Akula N, et al., 2002. Biotechniques. 32: 1072-8), fluorescence polarization (Hsu T M, et al., 2001. Biotechniques. 31: 560, 562, 564-8), Colorimetric oligonucleotide ligation assay (OLA, Nickerson D A, et al., 1990. Proc. Natl. Acad. Sci. USA. 87: 8923-7), Sequence-coded OLA (Gasparini P, et al., 1999. J. Med. Screen. 6: 67-9), Microarray ligation, Ligase chain reaction, Padlock probes, Rolling circle amplification, Invader assay (reviewed in Shi M M. 2001. Enabling large-scale pharmacogenetic studies by high-throughput mutation detection and genotyping technologies. Clin Chem. 47: 164-72), coded microspheres (Rao K V et al., 2003. Nucleic Acids Res. 31: e66) and MassArray (Leushner J, Chiu N H, 2000. Mol Diagn. 5: 341-80).

It will be appreciated that nucleic acid substitutions can be also identified in mRNA molecules derived from the individual. Such mRNA molecules are first subjected to an RT-PCR reaction following which they are either directly sequenced or be subjected to any of the SNP detection methods described hereinabove.

Thus, according to preferred embodiments of the present invention, identifying nucleic acid alteration in the mRNA sequence encoding CC2D1A or nup62 is effected using DNA sequencing of a CC2D1A or nup62 RT-PCR products.

Downregulation (decrease) of the expression level of CC2D1A or nup62 RNA sequences can be determined using molecular methods well known in the art such as Northern Blot analysis, RT-PCR, RNA in situ hybridization stain (using DNA or RNA probes), in situ RT-PCR stain [see description of method in Nuovo G J, et al. Intracellular localization of polymerase chain reaction (PCR)-amplified hepatitis C cDNA. Am J Surg Pathol. 1993, 17: 683-90 and Komminoth P, et al. Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25] using, e.g., an apparatus such as the laser-capture microdissection PixCell I LCM system available from Arcturus Engineering (Mountainview, Calif.).

Another method of detecting a decrease in the expression level of CC2D1A or nup62 RNA sequences is by an oligonucleotide microarray. In this method, oligonucleotide probes capable of specifically hybridizing with the polynucleotides of the present invention are attached to a solid surface (e.g., a glass wafer). Each oligonucleotide probe is of approximately 20-25 nucleic acids in length. To detect the expression pattern of the polynucleotides of the present invention in a specific cell sample (e.g., blood cells), RNA is extracted from the cell sample using methods known in the art (using, e.g., a TRIZOL® solution, Gibco-BRL™, USA). Hybridization can take place using either labeled oligonucleotide probes (e.g., 5'-biotinylated probes) or labeled fragments of complementary DNA (cDNA) or RNA (cRNA). Briefly, double-stranded cDNA is prepared from the RNA using reverse transcriptase (RT) (e.g., Superscript™ II RT), DNA ligase, and DNA polymerase I, all according to the manufacturer's instructions (Invitrogen Life Technologies, Frederick, Md., USA). To prepare labeled cRNA, the double-stranded cDNA is subjected to an in vitro transcription reaction in the presence of biotinylated nucleotides using, e.g., the BioArray™ HighYield™ RNA Transcript Labeling Kit (Enzo Diagnostics, Inc., Farmingdale, N.Y., USA). For efficient hybridization the labeled cRNA can be fragmented by incubating the RNA in 40 mM Tris Acetate (pH 8.1), 100 mM potassium acetate, and 30 mM magnesium acetate, for 35 minutes at 94° C. Following hybridization, the microarray is washed and the hybridization signal is scanned using a confocal laser fluorescence scanner, which measures fluorescence intensity emitted by the labeled cRNA bound to the probe arrays.

For example, in the Affymetrix® GeneChip® Microarray (Affymetrix, Inc., Santa Clara, Calif., USA), each gene on the array is represented by a series of different oligonucleotide probes, of which each probe pair consists of a perfect-match oligonucleotide and a mismatch oligonucleotide. While the perfect-match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent DNA Microarray Scanner™ (Agilent Technologies, USA) and the Microarray Suite™ (MAS) (Affymetrix, Inc.) software subtracts the non-specific signal of the mismatch probe from the signal resulting from the perfect-match probe.

Downregulation of the expression level of CC2D1A or p62 protein sequences can be determined using immunological methods well known in the art such as Enzyme linked immunosorbent assay (ELISA), Western blot analysis, radio-immunoassay (RIA) (using a specific antibody as described hereinabove and radiolabeled antibody binding protein (e.g., protein A labeled with $I^{125}$) immobilized on a precipitable carrier such as agarose beads), fluorescence activated cell sorting (FACS) which detects a substrate (e.g., a mutated CC2D1A or p62 protein) in situ in cells by substrate specific antibodies which are often linked to fluorophores), immunohistochemical analysis on fixed cells or tissue specimens such as paraffin-embedded sections or cryosections, using specific antibodies which are labeled directly (e.g., using a fluorophore) or indirectly (via an enzyme). It will be appreciated that immunohistochemistry is often followed by counterstaining of the cell nuclei using for example Hematoxyline or Giemsa stain.

The agents of the present invention which are described hereinabove for detecting sequence alterations and/or expression of CC2D1A or nup62 genes and.or gene products may be included in a diagnostic kit/article of manufacture preferably along with appropriate instructions for use and labels indicating FDA approval for use in diagnosing and/or assessing a severity of a pathology associated with mental retardation such as NSMR and IBSN.

Such a kit can include, for example, at least one container including at least one of the above described diagnostic agents (e.g., reagents such as the isolated nucleic acid sequence and/or the antibody or antibody fragment) and an imaging reagent packed in another container (e.g., HRP, alkaline phosphatase, fluorescently-labeled secondary antibodies, buffers, chromogenic substrates, fluorogenic material). The kit may also include appropriate buffers and preservatives for improving the shelf-life of the kit. Most preferably, the kit can include the addressable oligonucleotide microarray (DNA chip) described hereinabove.

As described hereinabove and in the Examples section which follows, the present inventors have uncovered that pathologies associated with mental retardation such as NSMR or IBSN are caused by disease-causing-mutations in the CC2D1A or nup62 genes, respectively, which result in downregulation of the expression level and/or activity of the CC2D1A or nup62 gene products (RNA or protein). Since CC2D1A is likely to be part of the NFkB pathway, it is conceivable that activation of the NFkB pathway (i.e., upstream and/or downstream components of the NfkB pathway, including activators and effectors, as well as co-factors of the NFkB pathway, see e.g., Xiao Adv Exp Med Biol. 2005; 560:41-5; Dalhalle A beginner's guide to NF-kappaB signaling pathways. Ann N Y Acad Sci. 2004, 1030:1-13. Review) such as by upregulating the expression level and/or activity of CC2D1A can be used to treat NSMR. In addition, since the mouse CC2D1A homologue, FREUD-1 is known to be a repressor of serotonin 5-HT1A receptor gene (Ou X-M., et al., 2003, J. Neuroscience, 23: 7415-7425), it is conceivable that upregulation of the serotonin receptor repressor pathway can be used to treat NSMR. Similarly, upregulation of the nup62 gene product (p62) can be used to treat IBSN, including both the mental retardation and the neurological symptoms of IBSN which involve e.g., neurodegeneration of the basal ganglia. It will be appreciated that upregulation of the activity of CC2D1A and/or nup62 gene products can be also achieved by downregulation of the expression level and/or activity of dominant negative forms of the CC2D1A or nup62 gene products such as the mutated CC2D1A or nup62 gene products uncovered in the present study.

Thus, according to yet another aspect of the present invention there is provided a method of treating a pathology associated with mental retardation. The method is effected by upregulating in a cell of an individual in need thereof an activity of an NFkB pathway and/or serotonin receptor repressor pathway (e.g., CC2D1A) or nup62 gene product (p62), thereby treating the pathology associated with mental retardation (including the neurodegeneration in IBSN).

The term "treating" refers to inhibiting or arresting the development of a pathology (e.g., pathology associated with mental retardation) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. The term "treating" further includes preventing the development of the pathology.

As used herein, the term "preventing" refers to keeping a pathology from occurring in a subject who may be at risk for the disease, but has not yet been diagnosed as having the disease (for example, if the subject is an unborn conceptus which carry on both of his alleles disease-causing-mutations).

The phrase "individual in need thereof" as used herein refers to an individual who is diagnosed with a mental retardation and/or neurodegeneration associated pathology (e.g., NSMR or IBSN) or who is homozygote or compound heterozygote to CC2D1A or nup62 disease-causing-mutations but does not exhibit clinical manifestation of the pathology (e.g., a conceptus or a newborn baby prior to the clinical manifestation of the pathology).

The phrase "upregulating in a cell of an individual in need thereof an activity" as used herein refers to upregulating in a cell of the individual the activity of the NFkB pathway and/or serotonin receptor repressor pathway (e.g., CC2D1A) or nup62 gene products (proteins). The cell used by the method according to this aspect of the present invention can be any cell of the individual in which modulation of the activity of the NFkB pathway and/or serotonin receptor repressor pathway (e.g., CC2D1A) or nup62 gene products can be used to treat the pathology associated with mental retardation (including neurodegeneration) in the individual. Non-limiting examples of such a cell can be any stem cell (embryonic stem cell or adult or tissue stem cell), a neuronal cell and/or a glial cell.

Upregulation of the activity of the NFkB pathway and/or serotonin receptor repressor pathway (e.g., CC2D1A) or nup62 gene products of the present invention can be effected by increasing the expression level and/or activity of the NFkB pathway and/or serotonin receptor repressor pathway (e.g., CC2D1A) or nup62 gene products, decreasing and/or inhibiting the activity of negative regulator(s) of the NFkB pathway and/or decreasing the expression level and/or activity of a mutated CC2D1A and/or nup62 gene products in the cell of the individual.

Preferably, upregulation of the activity of the NFkB pathway and/or serotonin receptor repressor pathway (e.g., CC2D1A) or nup62 gene products can be effected by contacting the cell with an exogenous polypeptide including at least a functional portion of the NFkB pathway and/or serotonin receptor repressor pathway (e.g., CC2D1A) or nup62 gene products.

As used herein, the phrases "polypeptide" or "peptide" which are interchangeably used herein, encompass a naturally occurring polypeptide which is comprised solely of natural amino acid residues, peptide analogues or mimetics thereof. The term "peptide" preferably refers to short amino acid sequences of at least 2 or 3, preferably at least 4, more preferably, at least 5, more preferably, in the range of 5-30, even more preferably in the range of 5-25 natural or non-natural amino acids which are capable of the biological activity (i.e., upregulating the expression level and/or activity of the NFkB pathway and/or serotonin receptor repressor pathway (e.g., CC2D1A) or nup62 gene products). Further description of natural and non-natural amino acids is provided in PCT Appl. No. IL2004/000744, which is fully incorporated herein by reference.

As used herein the term "mimetics" refers to molecular structures, which serve as substitutes for the peptide of the present invention in performing the biological activity (Morgan et al. (1989) Ann. Reports Med. Chem. 24:243-252 for a review of peptide mimetics). Peptide mimetics, as used herein, include synthetic structures (known and yet unknown), which may or may not contain amino acids and/or peptide bonds, but retain the structural and functional features of the peptide. Types of amino acids which can be utilized to generate mimetics are further described hereinbelow. The term, "peptide mimetics" also includes peptoids and oligopeptoids, which are peptides or oligomers of N-substituted amino acids [Simon et al. (1972) Proc. Natl. Acad. Sci. USA 89:9367-9371]. Further included as peptide mimetics are peptide libraries, which are collections of peptides designed to be of a given amino acid length and representing all conceivable sequences of amino acids corresponding thereto. Methods of producing peptide mimetics are described hereinbelow.

The phrase "functional portion" as used herein refers to at least a portion of the polypeptide of the present invention which is sufficient to treat mental retardation.

The polypeptide of the present invention can be biochemically synthesized such as by using standard solid phase techniques. These methods include exclusive solid phase synthesis, partial solid phase synthesis methods, fragment condensation and classical solution synthesis. These methods are preferably used when the polypeptide is relatively short (i.e., 10 kDa peptide) and/or when it cannot be produced by recombinant techniques (i.e., not encoded by a nucleic acid sequence) and therefore involve different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

It will be appreciated that for large polypeptides (e.g., above 25 amino acids), the exogenous polypeptide is preferably prepared using recombinant techniques.

For example, to generate the NFkB pathway and/or serotonin receptor repressor pathway (e.g., CC2D1A) or nup62 gene products of the present invention (e.g., a recombinant polypeptide such as the human CC2D1A set forth by SEQ ID NO:4 or the human nup62 set forth by SEQ ID NO:69), a polynucleotide sequence encoding the NFkB pathway and/or serotonin receptor repressor pathway (e.g., CC2D1A) or nup62 gene products [e.g., GenBank Accession numbers NM_017721.3 (SEQ ID NO:1) for CC2D1A or NM_012346 (SEQ ID NO:68) for nup62] or a functional portion thereof is preferably ligated into a nucleic acid construct suitable for expression in a host cell. Such a nucleic acid construct includes a promoter sequence for directing transcription of the polynucleotide sequence in the cell in a constitutive or inducible manner.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter [Zabala M, et al., Cancer Res. 2004, 64(8): 2799-804].

The nucleic acid construct (also referred to herein as an "expression vector") of the present invention includes additional sequences which render this vector suitable for replication and integration in prokaryotes, eukaryotes, or preferably both (e.g., shuttle vectors). In addition, a typical expression vector may also contain a transcription and translation initiation sequence, enhancers (e.g., SV40 early gene enhancer; see also Enhancers and Eukaryotic Expression, Cold Spring Harbor Press, Cold Spring Harbor, N.Y. 1983), transcription and translation terminator, and a polyadenylation signal which may increase the efficiency of mRNA translation (e.g., the GU or U rich sequences located downstream from the polyadenylation site and a highly conserved sequence of six nucleotides, AAUAAA, located 11-30 nucleotides upstream). It will be appreciated that in order to secret the recombinant polypeptide from the host cell (i.e., a cell in which the polynucleotide of the present invention is expressed) the expression vector of the present invention typically includes a signal sequence for secretion.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Other than containing the necessary elements for the transcription and translation of the inserted coding sequence, the expression construct of the present invention can also include sequences engineered to enhance stability, production, purification, yield or toxicity of the expressed polypeptide.

As mentioned hereinabove, a variety of cells can be used as host-expression systems to express the recombinant polypeptide of the present invention (e.g., human CC2D1A or human nup62). These include, but are not limited to, microorganisms, such as bacteria transformed with a recombinant bacteriophage DNA, plasmid DNA or cosmid DNA expression vector containing the polypeptide coding sequence, mammalian expression systems, yeast transformed with recombinant yeast expression vectors containing the coding sequence (see for example, U.S. Pat. No. 5,932,447); plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence [for suitable plant expression vectors see for example, Brisson et al. (1984) Nature 310:511-514; Takamatsu et al. (1987) EMBO J. 6:307-311; Coruzzi et al. (1984) EMBO J. 3:1671-1680; Brogli et al., (1984) Science 224:838-843; Gurley et al. (1986) Mol. Cell. Biol. 6:559-565; Weissbach & Weissbach, 1988, Methods for Plant Molecular Biology, Academic Press, NY, Section VIII, pp 421-463]. Bacterial systems are preferably used to produce recombinant polypeptides since they enable a high production volume at low cost.

In bacterial systems, a number of expression vectors can be advantageously selected depending upon the use intended for the polypeptide expressed. For example, when large quantities of polypeptide are desired, vectors that direct the expression of high levels of the protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the polypeptide may also be desirable. Such vectors adaptable to such manipulation include, but are not limited to, the pET series of *E. coli* expression vectors [Studier et al., Methods in Enzymol. 185:60-89 (1990)].

Examples for mammalian expression vectors include, but are not limited to, pcDNA3, pcDNA3.1(+/-), pGL3, pZeoSV2(+/-), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Stratagene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Various methods can be used to introduce the expression vector of the present invention into host cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency and specificity can be obtained due to the infectious nature of viruses.

Transformed cells are cultured under effective conditions, which allow for the expression of high amounts of the recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, resultant polypeptides of the present invention may either remain within the cell, secreted into the fermentation medium, secreted into a space between two cellular membranes, such as the periplasmic space in *E. coli*; or retained on the outer surface of a cell or viral membrane.

Following a predetermined time in culture, recovery of the recombinant polypeptide is effected. The phrase "recovery of the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and a fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The polypeptide of the present invention is preferably retrieved in "substantially pure" form. As used herein, the phrase "substantially pure" refers to a purity that allows for the effective use of the recombinant polypeptide (i.e., the NFkB pathway (e.g., CC2D1A) or nup62 gene products of the present invention) in treating mental retardation.

Another agent capable of upregulating the expression level and/or activity of the NFkB pathway (e.g., CC2D1A) or nup62 gene products of the present invention is an exogenous polynucleotide sequence designed and constructed to express in cells of the individual at least a functional portion of the NFkB pathway (e.g., CC2D1A) or nup62 gene products of the present invention. Accordingly, the exogenous polynucleotide sequence may be a DNA or RNA sequence encoding the NFkB pathway (e.g., CC2D1A) or nup62 gene products of the present invention.

It will be appreciated that for ex vivo or in vivo gene therapy applications which are further described hereinunder the exogenous polynucleotide of the present invention is administered to the cell-of-interest (e.g., brain cells such as neuronal cells or glial cells of the cortex and hippocampus for NSMR and of the basal ganglia for IBSN) to thereby treat the pathology associated with mental retardation (including neurodegeneration). As used herein, the phrase "ex vivo gene therapy" refers to the process of expressing the polypeptide of the present invention in cell cultures derived from a subject (e.g., autologous or allogeneic cells) followed by administration of such cells (which express the recombinant polypeptide of the present invention) back into the subject in need of therapy. The phrase "in vivo gene therapy" refers to the process of expressing the polypeptide of the present invention in cells of the subject in need of therapy.

It will be appreciated that the type of viral vector and the specific promoter used for ex vivo or in vivo gene therapy will depend on the cell type transformed. The ability to select suitable vectors according to the cell type transformed is well within the capabilities of the ordinary skilled artisan and as such no general description of selection consideration is provided herein.

Recombinant viral vectors are useful for in vivo expression of recombinant proteins since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element (s), or other elements that control gene expression by other means such as alternate splicing, nuclear RNA export, or post-translational modification of messenger. Such vector constructs also include a packaging signal, long terminal repeats (LTRS) or portions thereof, and positive and negative strand primer binding sites appropriate to the virus used, unless it is already present in the viral construct. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

As is mentioned hereinabove, upregulation of the NFkB pathway (e.g., CC2D1A) or nup62 gene product can be also effected by downregulating the activity of a mutated CC2D1A or nup62 in a cell of the individual and thus can be used to treat a pathology associated with mental retardation such as NSMR and/or IBSN. Downregulation of a mutated CC2D1A (e.g., a polypeptide as set forth by SEQ ID NO:5) or a mutated nup62 gene product (p62) (e.g., a polypeptide having a proline residue at position 391 of the amino acid sequence set forth in SEQ ID NO:69) which may exert dominant negative effects can be effected on the genomic and/or the transcript level using a variety of molecules that interfere with transcription and/or translation (e.g., antisense, siRNA, Ribozyme, DNAzyme, TFO), or on the protein level using, e.g., neutralizing antibodies, antagonists, enzymes that cleave the polypeptide, and the like.

Following is a list of agents capable of decreasing the expression level and/or activity of the mutated CC2D1A or nup62 gene products of the present invention.

One example of an agent capable of downregulating (or decreasing the expression level of) the mutated CC2D1A or nup62 gene products of the present invention is an antibody or antibody fragment as described hereinabove, which comprises an antigen recognition region capable of specifically binding to the mutated CC2D1A or nup62 gene products.

For example, to downregulate the expression level of a mutated human nup62 gene product (p62) the antibody can be directed against an epitope (e.g., a peptide of 3-8 amino acids) selected from the polypeptide set forth by SEQ ID NO:68, e.g., amino acids 388-393 of SEQ ID NO:68 which encompass the missense mutation (Q391P) causing IBSN.

Humanized forms of non-human (e.g., murine) antibodies are chimeric molecules of immunoglobulins, immunoglobulin chains or fragments thereof (such as Fv, Fab, Fab', F(ab') .sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10,: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

It will be appreciated that targeting of particular compartment within the cell can be achieved using intracellular antibodies (also known as "intrabodies"). These are essentially SCA to which intracellular localization signals have been added (e.g., nuclear, cytoplasmic). This technology has been successfully applied in the art (for review, see Richardson and Marasco, 1995, TIBTECH vol. 13). Intrabodies have been shown to virtually eliminate the expression of otherwise abundant cell surface receptors and to inhibit a protein function within a cell (See, for example, Richardson et al., 1995, Proc. Natl. Acad. Sci. USA 92: 3137-3141; Deshane et al., 1994, Gene Ther. 1: 332-337; Marasco et al., 1998 Human Gene Ther 9: 1627-42; Shaheen et al., 1996 J. Virol. 70: 3392-400; Werge, T. M. et al., 1990, FEBS Letters 274:193-198; Carlson, J. R. 1993 Proc. Natl. Acad. Sci. USA 90:7427-7428; Biocca, S. et al., 1994, Bio/Technology 12: 396-399; Chen, S-Y. et al., 1994, Human Gene Therapy 5:595-601; Duan, L et al., 1994, Proc. Natl. Acad. Sci. USA 91:5075-5079; Chen, S-Y. et al., 1994, Proc. Natl. Acad. Sci. USA 91:5932-5936; Beerli, R. R et al., 1994, J. Biol. Chem. 269: 23931-23936; Mhashilkar, A. M. et al., 1995, EMBO J. 14:1542-1551; PCT Publication No. WO 94/02610 by Marasco et al.; and PCT Publication No. WO 95/03832 by Duan et al.).

To prepare an intracellular antibody expression vector, the cDNA encoding the antibody light and heavy chains specific for the target protein of interest are isolated, typically from a hybridoma that secretes a monoclonal antibody specific for the marker. Hybridomas secreting anti-marker monoclonal antibodies, or recombinant monoclonal antibodies, can be prepared using methods known in the art. Once a monoclonal antibody specific for the marker protein is identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process and the nucleotide sequences of antibody light and heavy chain genes are determined. For example, many such sequences are disclosed in Kabat, E. A., et al. (1991) Sequences of Proteins of Immunological Interest, Fifth Edition, U.S. Department of Health and Human Services, NIH Publication No. 91-3242 and in the "Vbase" human germline sequence database. Once obtained, the antibody light and heavy chain sequences are cloned into a recombinant expression vector using standard methods.

Another agent capable of downregulating the mutated CC2D1A or nup62 gene products of the present invention is a small interfering RNA (siRNA) molecule. RNA interference is a two step process. In the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin. Genetics and Development 12:225-232 (2002); and Bernstein Nature 409:363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the mRNA sequence encoding the mutated CC2D1A or nup62 gene products (e.g., a mutated nup62 mRNA which includes a cytosine nucleotide at position 1429 of the nucleic acid sequence set forth by SEQ ID NO:68) is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (ambiondotcom/techlib/tn/91/912dothtml).

Second, potential target sites are compared to an appropriate genomic database (e.g., human, mouse, rat etc.) using any sequence alignment software, such as the BLAST software available from the NCBI server (ncbidotnlmdotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

The selected siRNAs can be chemically synthesized oligonucleotides (using e.g., solid phase synthesis) or can be encoded from plasmids in order to induce RNAi in cells following transfection (using e.g., the pRETRO-SUPER vector). Recently, retrovirus- or lentivirus-delivered RNAi were developed and were found efficient in long-term gene silencing in vivo [Hao D L., et al., 2005, Acta. Biochim. Biophys. Sin. (Shanghai), 37(11): 779-83].

Another agent capable of downregulating the mutated CC2D1A or nup62 gene products of the present invention is a DNAzyme molecule capable of specifically cleaving an mRNA transcript or DNA sequence of the mutated CC2D1A or nup62 gene products. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther. World Wide Webdotasgtdotorg). In another application, DNAzymes complementary to bcr-abl oncogenes were successful in inhibiting the oncogenes expression in leukemia cells, and lessening relapse rates iii autologous bone marrow transplant in cases of CML and ALL.

Downregulation of the mutated CC2D1A or nup62 gene products of the present invention can also be effected by using an antisense polynucleotide capable of specifically hybridizing with an mRNA transcript encoding the mutated CC2D1A or nup62 gene products (e.g., a mutated nup62 mRNA which includes a cytosine nucleotide at position 1429 of the nucleic acid sequence set forth by SEQ ID NO:68).

Design of antisense molecules which can be used to efficiently down-regulate the mutated CC2D1A or nup62 gene products must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating the expression of the mutated CC2D1A or nup62 gene products is a ribozyme molecule capable of specifically cleaving an mRNA transcript encoding the mutated CC2D1A or nup62 gene products. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Another agent which can be used to downregulate the expression level of the mutated CC2D1A or nup62 gene products of the present invention in cells is a triplex forming oligonucleotide (TFO). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989, 245:725-730; Moser, H. E., et al., Science, 1987, 238:645-630; Beal, P. A., et al, Science, 1992, 251:1360-1363; Cooney, M., et al., Science, 1988, 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo  | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, 3: 27.). The same authors have demonstrated that TFOs designed according to the A-AT and G-GC rule do not form non-specific triplexes, indicating that the triplex formation is indeed sequence specific.

Thus for any given sequence in the mutated CC2D1A or nup62 gene products a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

The upregulating or the downregulating agents described hereinabove (e.g., the polypeptides, nucleic acid constructs, antibodies, antisense, siRNA, DNAZyme, Ribozyme, TFO) of the present invention which are capable of modulating the expression level and/or activity of the NFkB pathway (e.g., CC2D1A) or nup62 gene product can be administered to an organism per se, or in a pharmaceutical composition where it is mixed with suitable carriers or excipients.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the agent accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a pathology (e.g., mental retardation such as NSMR or IBSN) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Mutated CC2D1A Causes Non Syndromic Mental Retardation (NSMR)

Initial clinical evaluation and linkage analysis studies of four consanguineous families with severe autosomal recessive NSMR comprising 10 affected and 24 unaffected individuals enabled the mapping of the NSMR candidate locus on chromosome 19p13.12-p13.2 to an interval of 2.4 Mb, between the loci D19S547 proximally and D19S1165 distally (3). In order to identify the gene causing NSMR, the present inventor has subjected the four original families (3) and five additional families, all of which live in the same village and bear the same family name, with a total of 16 affected and 48 unaffected individuals, to a comprehensive linkage analysis studies, as follows.

Materials and Experimental Methods

Study subjects—The study was reviewed and approved by the Human Subjects Committee of the Rabin Medical Center. The initial clinical presentation in all affected family members was psychomotor developmental delay during early childhood. All affected individuals had no or only single words and were severely mentally retarded, whereas their general physical examination was normal. There were no autistic features or seizures. The general appearance was normal, with no dysmorphic features; height, weight, and head circumference were normal in all except one patient, who had progressive microcephaly (OFC=45 cms [−4 SD] at the age of 2½ years). Neurological examination of the patients was normal. Formal psychological evaluation was carried out on one patient at the age of 8 years. During the examination his hyperactive behavior was notable. His attention span was very short and cooperation partial; he was constantly moving during the examination and refused to obey the commands given during the test. The most prominent feature was his attempt to initiate verbal contact and to try to convey his wishes. It was impossible to understand his speech and consequently he became frustrated. His verbal comprehension was limited to understanding concrete tasks and commands. He was assessed by the Leiter International Performance Scale [M. Batshaw, *Children with disabilities*. (Baltimore: Paul H Brookes Publishing, 1997), pp. 348-349] and was found to function in the severely mentally retarded range.

Microsatellite marker analysis—DNA was isolated from the blood samples by standard methods (J. McLaren, S. E. Bryson, Am. J. Ment. Retard 92, 243, 1987). Four hundred microsatellite markers, spaced at 10-cM intervals, from ABI PRISM linkage-mapping set version 2.5 (Applied Biosystems) were amplified by multiplex PCR, using standard protocols. Amplified markers were electrophoresed on an ABI 3700 DNA capillary sequencer and were analyzed with GENESCAN and GENOTYPER software (Applied Biosystems).

Sequencing of candidate genes—Genes in the candidate locus were identified by means of available databases (NCBI and University of California at Santa Cruz). Sequencing of the candidate genes was performed with primer sets designed using standard software (Primer 3). All exons, including exon-intron junctions, were amplified from genomic DNA with primers designed from the genomic sequences available from NCBI and University of California at Santa Cruz. Both strands of the PCR products were sequenced with BigDye Terminators (Applied Biosystems) on an ABI 3100 sequencer. Sequence chromatograms were analyzed using SeqScape software version 1.1 (Applied Biosystems). Initial test was performed on one affected individual, one heterozygous parent and a noncarrier sibling (as defined by haplotype analysis).

Molecular analysis of the CC2D1A gene—Based on the predicted genomic sequence, 24 PCR primer pairs were used for amplification of exons and splicing junctions. CC2D1A deletion mutation screening was performed on genomic DNA by PCR reactions using the following primers: for normal alleles: primer A (forward): GTGGATGTCGCTGAATTGC (SEQ ID NO:6), primer B (reverse): CAAGCGATCCTC-CCATCTT (SEQ ID NO:7); for mutant alleles: primer A (forward): GTGGATGTCGCTGAATTGC (SEQ ID NO:6), primer C (reverse): TACAGTCCTCCGCCAACTTT (SEQ ID NO:8). For the detection of the deletion mutation the PCR conditions were: Denaturation: 94° C., 3 minutes, 9 cycles of: denaturation at 94° C., 30 seconds, annealing starting at 64° C. and annealing temperature decreases in 1° C. each cycle (i.e., 64° C.-1° C.), 30 seconds and elongation at 72° C., 30 seconds, 26 cycles of: denaturation at 94° C., 30 seconds, annealing at 55° C., 30 seconds and elongation at 72° C., 30 seconds, followed by 10 minutes elongation at 72° C.

TABLE 1

PCR primers for genomic amplification of CC2D1A

| Primer name (SEQ ID NO:) | Sequence from 5' to 3' | PCR conditions (Annealing Temperature and No. of PCR cycles) |
|---|---|---|
| FLJ20241-EX1F (SEQ ID NO:16) | ctttaagggaggcagtggtg | 64° C.-1° C. 9 cycles |
| FLJ20241-EX1R (SEQ ID NO:17) | tcctggcctcggtgatct | 55° C. 26 cycles |
| FLJ20241-EX2F (SEQ ID NO:18) | gccaatccttgcttcctttt | 55° C. 35 cycles |
| FLJ20241-EX2R (SEQ ID NO:19) | atgggctgaggtggaggta | 64° C.-1° C. 9 cycles |
| FLJ20241-EX3F (SEQ ID NO:20) | atgagcgacgcaaacacc | 55° C. 26 cycles |
| FLJ20241-EX3R (SEQ ID NO:21) | tacctgtgggcggagat | 55° C. 35 cycles |
| FLJ20241-EX4F (SEQ ID NO:22) | gggactctctggccatcat | 64° C.-1° C. 9 cycles |

TABLE 1-continued

PCR primers for genomic amplification of CC2D1A

| Primer name (SEQ ID NO:) | Sequence from 5' to 3' | PCR conditions (Annealing Temperature and No. of PCR cycles) |
|---|---|---|
| FLJ20241-EX4R (SEQ ID NO:23) | ctacccagtgcccccagt | 55° C. 35 cycles |
| FLJ20241-EX5 + 6F (SEQ ID NO:24) | gcgagaagtgggatcaccta | 64° C.-1° C. 9 cycles |
| FLJ20241-EX5 + 6R (SEQ ID NO:25) | ggtgacacagcaagactcca | 55° C. 26 cycles |
| FLJ20241-EX7F (SEQ ID NO:26) | atggggccgactgttactg | 64° C.-1° C. 9 cycles |
| FLJ20241-EX7R (SEQ ID NO:27) | gtttgggagaagccaagagc | 55° C. 26 cycles |
| FLJ20241-EX8F (SEQ ID NO:28) | gcagagggcagggtacag | 64° C.-1° C. 9 cycles |
| FLJ20241-EX8R (SEQ ID NO:29) | cccctagagcagcatcc | 55° C. 26 cycles |
| FLJ20241-EX9F (SEQ ID NO:30) | catgggcaacagagtgagg | 64° C.-1° C. 9 cycles |
| FLJ20241-EX9R (SEQ ID NO:31) | gatgcaaatttgggtgcttt | 55° C. 26 cycles |
| FLJ20241-EX10F (SEQ ID NO:32) | aaatggaagggagggagcta | 64° C.-1° C. 9 cycles |
| FLJ20241-EX10R (SEQ ID NO:33) | gtctctgggcctgaccaac | 55° C. 26 cycles |
| FLJ20241-EX11 + 12F (SEQ ID NO:34) | gttggtcaggcccagagac | 64° C.-1° C. 9 cycles |
| FLJ20241-EX11 + 12R (SEQ ID NO:35) | ctcggatggcatcttggtat | 55° C. 26 cycles |
| FLJ20241-EX13F (SEQ ID NO:36) | gaaagctcgaatgcacgag | 64° C.-1° C. 9 cycles |
| FLJ20241-EX13R (SEQ ID NO:37) | gctggaggaacaggagctt | 55° C. 26 cycles |
| FLJ20241-EX14F (SEQ ID NO:38) | ggaatctgcatctccaccat | 64° C.-1° C. 9 cycles |
| FLJ20241-EX14R (SEQ ID NO:39) | caagcgatcctcccatctt | 55° C. 26 cycles |
| FLJ20241-EX15F (SEQ ID NO:40) | accctgatccttggggact | 64° C.-1° C. 9 cycles |
| FLJ20241-EX15R (SEQ ID NO:41) | cttgcggccctctaggaag | 55° C. 26 cycles |
| FLJ20241-EX16F (SEQ ID NO:42) | gtaagccacatccaccagaggta | 64° C.-1° C. 9 cycles |
| FLJ20241-EX16R (SEQ ID NO:43) | acagcagctggaccttgact | 55° C. 26 cycles |
| FLJ20241-EX17 + 18F (SEQ ID NO:44) | ccctcgtcaaggaagaatga | 64° C.-1° C. 9 cycles |
| FLJ20241-EX17 + 18R (SEQ ID NO:45) | tacagtcctccgccaactttt | 55° C. 26 cycles |
| FLJ20241-EX19F (SEQ ID NO:46) | ctgggcaacatcactgaaac | 64° C.-1° C. 9 cycles |

TABLE 1-continued

PCR primers for genomic amplification of CC2D1A

| Primer name (SEQ ID NO:) | Sequence from 5' to 3' | PCR conditions (Annealing Temperature and No. of PCR cycles) |
|---|---|---|
| FLJ20241-EX19R (SEQ ID NO:47) | agagcctttgcatgctctgt | 55° C. 26 cycles |
| FLJ20241-EX20 + 21F (SEQ ID NO:48) | ccactgggggaagagaagg | 64° C.-1° C. 9 cycles |
| FLJ20241-EX20 + 21R (SEQ ID NO:49) | aggaggcaggaaatctaggg | 55° C. 26 cycles |
| FLJ20241-EX22 + 23F (SEQ ID NO:50) | cggtttgacttccccatcc | 64° C.-1° C. 9 cycles |
| FLJ20241-EX22 + 23R (SEQ ID NO:51) | acccggcagcgaacag | 55° C. 26 cycles |
| FLJ20241-EX24F (SEQ ID NO:52) | ggttcacaaggggtgagcta | 64° C.-1° C. 9 cycles |
| FLJ20241-EX24R (SEQ ID NO:53) | acaggctcatagagggctca | 55° C. 26 cycles |
| FLJ20241-EX25 + 26F (SEQ ID NO:54) | cagtcttgttctcccttgtcc | 64° C.-1° C. 9 cycles |
| FLJ20241-EX25 + 26R (SEQ ID NO:55) | gaaagggcagcaggag | 55° C. 26 cycles |
| FLJ20241-EX27 + 28F (SEQ ID NO:56) | cagcccagtgtgtcttttga | 64° C.-1° C. 9 cycles |
| FLJ20241-EX27 + 28R (SEQ ID NO:57) | cagatatgcatccctgagca | 55° C. 26 cycles |
| FLJ20241-EX29 + 30F (SEQ ID NO:58) | cttggggatgggcacagt | 64° C.-1° C. 9 cycles |
| FLJ20241-EX29 + 30R (SEQ ID NO:59) | gtctggttcgtggctgtgt | 55° C. 26 cycles |
| FLJ20241-EX31.1F (SEQ ID NO:60) | cgctctataggcggaatctg | 64° C.-1° C. 9 cycles |
| FLJ20241-EX31.1R (SEQ ID NO:61) | tggggaggaacaggaagtaa | 55° C. 26 cycles |
| FLJ20241-EX31.2F (SEQ ID NO:62) | gggtgttgggaaccatgc | 64° C.-1° C. 9 cycles |
| FLJ20241-EX31.2R (SEQ ID NO:63) | ggggggggaagacc | 55° C. 26 cycles |

PCR primers and reaction conditions used to amplify all 31 exons of the CC2D1A gene. PCR reactions included: denaturation: 94° C., 3 minutes, 9 cycles of: 94° C., 30 seconds, annealing at the specified temperature for 30 seconds and 72° C., 30 seconds, followed by 10 minutes elongation at 72° C.

Human RNA isolation—RNA was extracted from the blood of the affected and unaffected individuals using the Trizol reagent (Gibco BRL, Catalog Number 15592-026) and reverse transcriptase (RT) reactions were performed with both random hexamers and oligo dT primers in order to obtain cDNA. Subsequence PCR reactions (RT-PCR) were performed using the forward primer from exon 13 of CC2D1A (SEQ ID NO:2) and the reverse primer from exon 17 of CC2D1A (SEQ ID NO:3). PCR conditions were essentially as described hereinabove for genomic PCR reactions.

Western blot—Lymphoblast cell proteins were subjected to Western blot analysis using the CC2D1A antibody. Briefly, cells were washed twice with PBS and lysed at 4° C. with lysis buffer (0.6% NP40 and protease inhibitors). After 15 minutes of incubation, cell lysates were centrifuged for 5 minutes at 14,000 rpm and supernatants were collected. Protein concentrations were determined using the BCA Protein Assay Reagent Kit (PIERCE). Whole-cell proteins (approximately 20 μg) were subjected to 7.5% SDS-PAGE and transferred to nitrocellulose membranes. The membranes were blocked for 30 minutes at room temperature with 5% skim milk in Tris-buffer (10 mM Tris, 150 mM NaCl, and 0.1% Tween-20) and subsequently incubated with anti-CC2D1A rabbit polyclonal antibody (BL695, Bethyl laboratories) diluted 1:20000, rabbit polyclonal anti-emerin (sc-15378, Santa Cruz Biotechnology) diluted 1:5000, mouse monoclonal antibody anti-NF-κB p50 (sc-8414, Santa Cruz Biotechnology) diluted 1:1000 or mouse monoclonal antibody p65 (sc-8008, Santa Cruz Biotechnology) diluted 1:5000. After washing and subsequent incubation for 1 hour with horseradish peroxidase coupled to anti-rabbit IgG or mouse IgG respectively (Jackson ImmunoResearch Laboratories, West Grove, Pa.), immunoreactive proteins were visualized by an ECL (enhanced chemiluminescence super signal) Detection Kit (PIERCE). Antibody to Emerin protein (sc-15378, Santa Cruz Biotechnology) was used to demonstrate the loading level.

Experimental Results

Narrowing down of the NSMR locus to 900 kb—As shown in FIGS. 1a-i, genotyping of polymorphic markers in all 9 families resulted in narrowing down of the NSMR critical region to a region of 900 kb between the polymorphic markers D19S564 and D19S547. As is further shown in FIG. 2, this region (minimal candidate region) contains 14 genes: MGC10471 (GenBank Accession No. NM_030818), MGC3207 (GenBank Accession No. NM_001031727), HSPC023 (GenBank Accession No. NM_014047), MGC11271 (GenBank Accession No. XM_929354), CC2D1A (GenBank Accession No. NM_017721.3; SEQ ID NO:1), FLJ23447 (GenBank Accession No. BC057786), RFX1 (GenBank Accession No. NM_002918), RLN3 (GenBank Accession No. NM_080864), IL27RA (GenBank Accession No. NM_004843), SAMD1 (GenBank Accession No. NM_138352), PRKACA1 (GenBank Accession No. NM_207518), ASF1B (GenBank Accession No. NM_018154) and LPHN1 (GenBank Accession Nos. NM_001008701 and NM_014921).

Identification of a deletion in the CC2D1A gene in NSMR affected family members—Sequencing of exons 14, 15 and 16 of the CC2D1A gene demonstrated failure of amplification in all the affected family members as opposed to successful amplification in heterozygous and homozygous normal individuals (data not shown). Sequencing of the cDNA with the primers derived from exons 13 (SEQ ID NO:2; GTGGATGTCGCTGAATTGC) and 17 (SEQ ID NO:3; TACAGTCCTCCGCCAACTTT) confirmed complete deletion of exons 14, 15 and 16; sequencing of the genomic DNA with the primers flanking the exon-intron junctions for exons 13 and 17 (primers A, B and C; SEQ ID NOs:6, 7 and 8, respectively) revealed the deletion of 3589 nucleotides beginning in intron 13 and ending in intron 16. The deletion causes removal of amino acids 408 to 547 and introduces a frameshift of the encoded protein (GenBank Accession No. NP_060191; SEQ ID NO:4) immediately after the deletion, creating a nonsense peptide of 30 amino acids (aa) and a stop codon at position 438 of the mutant protein (SEQ ID NO:5). In each pedigree analyzed, the CC2D1A mutation segregates with the disease; affected patients displayed homozygous CC2D1A deletion mutation, whereas parents who are clinically normal displayed heterozygosity for a normal and a disease allele, consistent with recessive inheritance (FIGS. 3a-b and FIGS. 4a-b). The mutation was not observed in 300 control chromosomes including 100 Jewish and 50 Israeli Arab individuals (data not shown). The protein encoded by CC2D1A was therefore identified as the causative gene leading, when mutated, to NSMR.

The structure of CC2D1A protein—The CC2D1A gene (as set forth by nucleotides 13864993-13902692 of GenBank accession No. NC_000019.8; SEQ ID 110) covers about 37 kb of genomic DNA on 19p13.12. It encodes 3715 bp-long mRNA (GenBank Accession No. NM_017721.3; SEQ ID NO:1), containing 31 exons. At least twelve splice variants have been identified (University of California at Santa Cruz database). The coding sequence is 2853 bp long. The gene is widely expressed in various tissues such as brain, retina, spleen thymus, muscle, kidney, lung, pancreas, prostate, lymphoblastoid cells. The CC2D1A protein (GenBank Accession No. NP_060191; SEQ ID NO:4) contains 951 amino acids, although a shorter isoform of the protein exists, which contains only 388 amino acids. The shorter isoform does not contain exons 14 to 16. Thus, only the long protein isoform seems to carry a central role in disease pathogenesis in the patients. A search against the CDart database (Hypertext Transfer Protocol://World Wide Webdotncbidotnlmdotnihdotgov/Structure/lexington/lexington.cgi) revealed that the protein family carries two conserved motifs. The most conserved motif is a C2 domain (IPR008973, IPR006608, IPR000008). This motif, which is located at the C-terminus of CC2D1A, at positions 661-762, is found in proteins which function in calcium-dependent phospholipid binding (B. A. Davletov, T. C. Suedhof, J. Biol. Chem. 268: 26386, 1993), where the C2 domain itself participates in the binding pocket of the $Ca^{+2}$ cation. Proteins which have a C2 domain include phospholipases, protein kinase C, and also the synaptotagmin protein family. Synaptotagmins are synaptic vesicle membrane-trafficking proteins. The other motif, DM14, is unique to the CC2D1A protein family and its role is unknown. It repeats four times in the human CC2D1A sequence hut only three times in the *Caenorhabditis elegans* orthologue sequence. The DM14 motif also appears only in the long isoform of CC2D1A, while the C2 domain, which is present in both isoforms, probably has a central role in its protein activity. The protein-truncating mutation in the NSMR patients identified in the present study abolishes one of the four DM14 domains and the C2 domain (FIG. 5).

NSMR patients carry a truncated CC2D1A protein—To further substantiate the findings that patients with a deleted allele in the CC2D1A gene express a truncated protein, Western blot analysis was performed on lymphoblast cells derived from a normal, unaffected individual and an affected NSMR subject. As is shown in FIG. 6a, while in unaffected individuals (control), the CC2D1A antibody recognized a clear protein band of about 104 kDa, in the affected NSMR subjects (patient), the protein band representing wild type protein was absent, and a smaller protein band of approximately 85 kDa was observed (FIG. 6a). Since the antibody used to detect the mutated protein was directed against an epitope in the N-terminus of the CC2D1A protein, the recognition of a shorter CC2D1A protein in affected individuals using this antibody indicates that the mutated CC2D1A protein is a truncated protein which includes the N-terminus of CC2D1A. A predicted amino acid sequence of the truncated CC2D1A protein, which is based on the deleted nucleic acid sequence in the affected NSMR individuals, is set forth by SEQ ID NO:5. As a control for the integrity of the protein preparation, an antibody for the Emerin protein (GenBank Accession No. NP_000108) was used. As can be seen in FIG. 6b, no difference was observed in either the intensity or size of the Emerin protein product between NSMR patients of unaffected individuals.

Altogether, these findings demonstrate, for the first time, the identification of a disease-causing-mutation in the CC2D1A gene which results in NSMR. These finding therefore suggest the use of mutational screening in the CC2D1A gene for the diagnosis of NSMR in individual in need thereof, including in prenatal diagnosis.

Example 2

CC2D1A is a Cytoplasmic Protein Expressed in Brain Cells

Matsuda et al. originally identified CC2D1A as a putative signal transducer participating in positive regulation of I-κB kinase/NF-κB cascade (A. Matsuda et al., Oncogene 22: 3307, 2003)). Their large-scale study was designed to identify human genes that activate the NF-κB and MAPK signaling pathways, and they reported that the CC2D1A gene was found to induce at least fourfold the transcription of a luciferase reporter gene driven by a promoter containing the consensus NF-κB binding sites. In order to understand the mechanisms leading to mental retardation as a result of a mutation in CC2D1A, the present inventor has studied the expression pattern of CC2D1A and its possible interaction with the p65 and p50 subunits of the NF-κB complex, as follows.

Materials and Experimental Methods

Immunofluorescence—U2OS cells were grown on cover slips overnight. The cells were fixed for 5 minutes with ice-cold methanol followed by ice-cold acetone (5 minutes), washed with TBS (100 mM Tris-HCl pH 7.5, 150 mM NaCl) and blocked for 30 minutes with 5% skim milk in TBS containing 0.1% Tween-20 (TBS-T). Incubations with primary rabbit polyclonal anti-CCD21A (Bethyl laboratories, 1:100 dilution) and secondary Cy3-conjugated donkey anti-rabbit (Jackson, 1:500 dilution) antibodies were performed in blocking solution for 1 hour each. Between and after the incubation with the antibodies cells were washed 3 times with TBS-Tween. The cover slips were mounted using DAPI containing Fluoromount-G (SouthernBiotech) and the cells photographed after fluorescent microscopy analysis.

Immunoprecipitation—A sample of approximately 200 µg total protein from the lymphoblasts of a patient and a control subject were incubated (while rotating at 4° C.) with rabbit anti-CC2D1A antibody (diluted 1:100) overnight. Subsequently 50 µl anti-rabbit IgG (whole molecule) agarose antibody (SIGMA) was added and the mixture was incubated for 1 hour at room temperature. The agarose beads were washed once with a lysis buffer and three additional times with PBS. Absorbed proteins were solubilized with SDS-PAGE sample buffer and subjected to electrophoresis on 12% polyacrylamide gels and immunoblotted as described hereinbelow for the Western blot analysis.

In situ hybridization—Non-radioactive in situ hybridization (ISH) was performed as previously described in frozen mouse brains, using digoxigenin (DIG)-labeled cRNA probes (3). Briefly, the murine CC2D1A probes were generated by PCR from IMAGE clone 5363547 (GenBank Accession No. BC027028). Probes were generated at the following nucleotide (nt) sequence positions in the CC2D1A cDNA; probes: CC2D1A-1 (nt 38-506; SEQ ID NO:9; 469 bp), and CC2D1A-2 (nt 2657-3021; SEQ ID NO:10; 365 bp; 3'-UTR). All CC2D1A nucleotide probe sequences were from nucleotides downstream of the ATG start site (corresponds to nucleotide 69 at GenBank Accession No. BC027028; SEQ ID NO:11). The probes were made by PCR reactions using primers which contain the T3 promoter sequences on their 5'-ends in order to drive the transcription of the cRNA sense probes (all forward primers) or the T7 promoter sequences on their 5'-ends in order to drive the transcription of the cRNA antisense probes (all reverse primers).

Frozen brains were sectioned (10-20 µm) in a cryostat and placed on Superfrost plus microscope slides. Brain sections were fixed, acetylated, and hybridized at 68° C. (approximate concentration of probe 100 ng/ml). Hybridized probes were visualized using alkaline phosphatase-conjugated anti-DIG Fab fragments (Roche, Indianapolis, Ind.) and 5-Bromo-4-chloro-3-indolyl-phosphate/Nitro blue tetrazolium (BCIP/NBT) substrate (Kierkegard and Perry Laboratories (KPL), Gaithersburg, Md.). Sections were washed and cover slipped with glycerol gelatin (Sigma, St. Louis, Mo.). Both CC2D1A antisense probes yielded comparable expression patterns.

Experimental Results

CC2D1A is localized at the cytoplasm of U2O2 cells—To determine the subcellular localization of CC2D1A, immuno-labeling experiments were performed by using polyclonal antibody on U2OS cells. As is shown in FIG. 7, CC2D1A protein is distributed throughout the cytoplasm; no signal was detected in the nuclei. CC2D1A is a soluble protein, as no transmembrane regions were detected. The absence of signal peptide in the protein sequence suggests that it is not secreted. Sequence similarity searches of the CC2D1A protein, using BLASTP against SWISS-PROT and non-redundant databases, revealed similarity to many potential orthologues in mammals, in other vertebrates (*Xenopus lavis*, tetraodon), as well as in invertebrates (*Drosophila melanogaster* and *Caenorhabditis elegans*) (S. F. Altschul, et al., J. Mol. Biol. 215, 403, 1990). No candidate orthologue was found in the yeast genome. In vertebrates the gene was duplicated, since two paralogs are found in the tetraodon genome and the mammalian genome. Although only one copy was found in the frog genome, this is probably because the full genome sequence was yet not determined. A phylogenetic analysis of the CC2D1A protein family is shown in FIG. 8. All protein family members are predicted and their function is unknown. A multiple alignment of the C2 domain and one of the DM14 domains are shown in FIGS. 9a and b, respectively.

CC2D1A does not directly interact with the p65 and p50 subunits of the NF-κB complex—The possible direct interaction between CC2D1A and the p65 or p50 subunits of the NF-κB complex was examined by using coimmunoprecipitation of the endogenous proteins in control lymphoblastoid cells. The immunoprecipitation analyses demonstrate that CC2D1A does not directly interact in vivo with the NF-κB p65 subunit (FIGS. 10a-b) or the p50 subunit (data not shown).

Figure 11D:
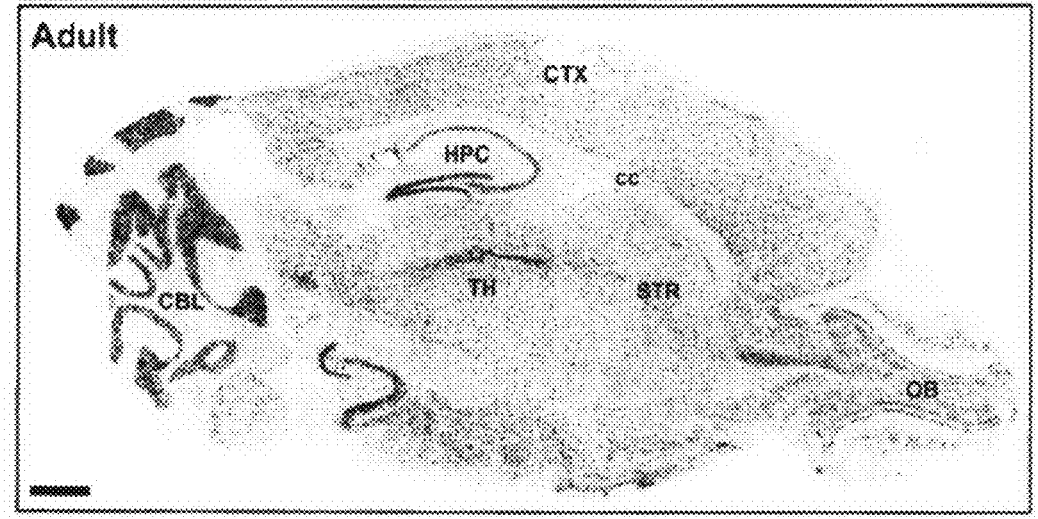

CC2D1A expression is restricted to the ventricular zone progenitors and neurons—To determine the spatial expression patterns of CC2D1A during brain development staged mouse embryos were subjected to in situ hybridization analysis. CC2D1A mRNA was observed at mouse embryonic day 12 (E12) throughout the ventricular zone and developing cortical plate and ganglionic eminences (FIG. 11a). By mouse embryonic day 16 (E16), CC2D1A mRNA is found throughout the mouse brain, but most strongly in the cortical plate (FIG. 11b). At postnatal day 3 (P3), CC2D1A mRNA is still widely expressed with strong expression in the cerebral cortex and hippocampus (particularly in the hippocampal CA3 region; FIG. 11c). Continued expression is observed in the brain into adulthood (FIG. 11d). The expression patterns of the CC2D1A mRNA appear to be restricted mostly to the ventricular zone progenitors and neurons. Given these expression patterns in the cerebral cortex and hippocampus and the cognitive phenotype in patients with CC2D1A mutations, CC2D1A appears to be a critical modulator of some aspects of synaptic plasticity.

Analysis and Discussion

The immunoprecipitation analyses demonstrate that CC2D1A does not directly interact in vivo with the NF-κB p65 or p50 subunits (FIGS. 10a-b and data not shown). These results may suggest that NF-κB expression is regulated by the CC2D1A gene via other signaling proteins that belong to the IKK/IκB-dependent or the IKK/IκB independent pathway. Functional NF-κB complexes are present in all cell types in the nervous system, including neurons, microglia, oligodendrocytes and astrocytes (L. A. O'Neill, C. Kaltschmidt, Trends Neurosci. 20, 252, 1997). Stimulation of glutamate receptors and membrane depolarization stimulate NF-κB activation in neurons, probably via a calcium-mediated mechanism. NF-κB is also activated in association with long-term potentiation (LTP) of synaptic transmission, a process believed to be related to learning and memory (P. J. Meberg, et al., Brain Res. Mol. Brain Res. 38, 179, 1996). Electrophysiological measurements of synaptic plasticity in hippocampal cells from mice lacking TNF-α receptors suggest an important function of NF-κB in the long-term depression (LTD) of synaptic transmission (B. C. Albensi, M. P. Mattson, Synapse 35, 151, 2000). Along with the potential role of NF-κB in neuronal function in the brain, there is an indication that NF-κB might be important for neuronal development based on the pattern of NF-κB activity in the brain during mouse development (R. Schmidt-Ullrich, et al., Development 122, 2117, 1996). Basal synaptic input in mature mouse hippocampal neurons activates the NF-κB transcription factor and induces κB DNA-binding activity consisting of p50:p65 and p50:p50 dimers. Mice lacking p65 show a selective learning deficit in the spatial version of the radial arm maze. These observations suggest that long-term changes to adult neuronal function caused by synaptic stimulation can be regulated by NF-κB nuclear translocation and gene activation (M. K. Meffert, J. M. Chang, B. J. Wiltgen, M. S. Fanselow, D. Baltimore, Nat. Neurosci. 6, 1072, 2003).

Altogether, the expression pattern of CC2D1A in the cerebral cortex and hippocampus demonstrates its significant involvement in the cognitive phenotype observed in NSMR patients with CC2D1A mutations and suggests that CC2D1A is a critical modulator of synaptic plasticity.

Example 3

Mutated nup62 Causes Autosomal Recessive Infantile Bilateral Striatal Necrosis (IBSN)

Materials and Experimental Methods

IBSN study subjects—A total of eight Israeli Bedouin families with IBSN with 12 affected and 39 unaffected individuals, including six interrelated families who were described elsewhere (7, 8) and two new families identified during this study were clinically ascertained. All the families bear the same family name. The exact relationships between five of the families are known (7) while those of the three remaining families to the other five are not known. The clinical manifestations, radiological evolution, and neuropathological characteristics of the disease in the original family have been described by Straussberg et al. (7). The age of onset of the disease in the affected individuals ranged from 7 to 15 months. The most prominent neurological findings were choreoathetoid movements of the face, trunk and extremities, dystonia, horizontal pendular nystagmus, optic atrophy and spastic quadriparesis. Gradual disappearance of the basal ganglia was evident on serial brain MRI scans. Initial MRI scans, performed on three symptomatic patients at 11, 12, and 15 months, revealed no abnormalities. At the age of 20-21 months, they showed caudate nuclei and putamen of normal size, but on T2-weighted images, bilateral, symmetric, hyperintense signals were visible in the putamen. Follow-up at 6 years revealed further changes. The caudate nucleus and the putamen were atrophic, and the putamen showed a low signal on T1-weighted images and a high signal on T2-weighted images. At the age of 10-11 years, MRI scans showed a small, residual caudate nucleus and putamen with abnormal signals. Diffuse parenchymal loss was evident.

Extensive metabolic workup was normal. Informed consents were obtained from either the family members who agreed to participate in the study or from their legal guardians. The research study was reviewed and approved by the Human Subjects Committee of the Rabin Medical Center.

Microsatellite Marker Analysis—DNA was isolated from the blood samples by standard methods (Sambrook J, Fritsch E, Maniatis T. Molecular cloning: a laboratory manual 2nd ed. New York: Cold Spring Harbor Laboratory Press, —1989). Microsatellite markers were amplified by multiplex PCR, using standard protocols. Amplified markers were electrophoresed on an ABI 3700 DNA capillary sequencer and were analyzed with GENESCAN and GENOTYPER software (Applied Biosystems).

SNP analysis—Sequencing of the single nucleotide polymorphisms (SNPs) was performed with primer sets designed using the Primer 3 program. The genomic sequence was taken from the UCSC Genome Browser.

Sequencing of candidate genes—Sequencing of the candidate genes was performed with primer sets designed using the Primer 3 program. All exons including exon-intron junctions, 5'-UTRs and 3'-UTRs were amplified from genomic DNA with primers designed from the genomic sequences available from UCSC Genome Browser. Both strands of the PCR products were sequenced with BigDye Terminators (Applied Biosystems) on an ABI 3100 sequencer. Sequence chromatograms were analyzed using SeqScape software version 1.1 (Applied Biosystems). Initial testing was of one affected individual, one heterozygous parent and a noncarrier sibling (as defined by haplotype analysis).

Molecular analysis of the nup62 gene—Based on the predicted genomic sequence, 16 primer pairs were used for PCR amplification of exons and exon-intron junctions (primer sequences available on request). Nup62 mutation screening was performed on genomic DNA by PCR amplification using the following primers: primer A (forward): ACGCTGATC-GAGAATGGAGA (SEQ ID NO:64), primer B (reverse): TTTTCTCACGCTCCTCATCC (SEQ ID NO:65); the PCR product was digested with the NCiI restriction enzyme (New England Biolabs). The normal allele produced an uncut fragment of 208 bp, and the abnormal allele (encoding the disease-causing-mutation Q391P) produced two fragments of 125 bp and 83 bp.

Mutational screening of the nup62 in individuals unrelated to the above described Bedouin family—For mutational screening, the genomic DNA encoding nup2 is amplified using the following primer pairs, and amplified fragments are subjected to DNA sequencing using e.g., the DyeTerminator sequence analysis kit.

TABLE 2

PCR primers for genomic amplification of nup62

| PCR product Number | Exon Number | Primer Sequence from 5' to 3' (SEQ ID NO:) | |
|---|---|---|---|
| 1 | 1 | Forward: CCAGGGCTCCCTAAAGAGG | (SEQ ID NO:73) |
|   |   | Reverse: CATGGCTCTGTAGCCTCGAC | (SEQ ID NO:74) |
| 2 | 2 | Forward: GAGGTGGATGTCCGTCTTTT | (SEQ ID NO:75) |
|   |   | Reverse: CAGCTACTCTGGCTCCCAAA | (SEQ ID NO:76) |
| 3 | 3 | Forward: CCAAAACTGCCATCTGACAA | (SEQ ID NO:77) |
|   |   | Reverse: TAAACCCTCCAGTGCCAGAG | (SEQ ID NO:78) |
| 4 | 3 | Forward: ACTGCAAAGACGGCAACAAC | (SEQ ID NO:79) |
|   |   | Reverse: GCAGCTGTGTTGCTCAAGTT | (SEQ ID NO:80) |
| 5 | 3 | Forward: ATATCGAGCACCGTCACCTC | (SEQ ID NO:81) |
|   |   | Reverse: CTGCTGAGCCAATGTTGAAA | (SEQ ID NO:82) |
| 6 | 3 | Forward: AACCCTCCGGTTTCAACATT | (SEQ ID NO:83) |
|   |   | Reverse: CTCCAGGTGCCTTTAAGCTG | (SEQ ID NO:84) |
| 7 | 3 | Forward: CACCTCCACAACAACATCCA | (SEQ ID NO:85) |
|   |   | Reverse: GTCCCAGGCGTTGACCTG | (SEQ ID NO:86) |
| 8 | 3 | Forward: ACGCTGATCGAGAATGGAGA | (SEQ ID NO:87) |
|   |   | Reverse: TTTTCTCACGCTCCTCATCC | (SEQ ID NO:88) |
| 9 | 3 | Forward: ACATCGATGCACAGCTCAAG | (SEQ ID NO:89) |
|   |   | Reverse: AAAGGTGATCCGGAAGCTG | (SEQ ID NO:90) |
| 10 | 3 | Forward: CCCTAGGGAGTTCATGAGG | (SEQ ID NO:91) |
|   |   | Reverse: GGTCGCAGTAGGTGAAAAGG | (SEQ ID NO:92) |
| 11 | 3 | Forward: TTGGCCCCTTTTCACCTACT | (SEQ ID NO:93) |
|   |   | Reverse: TCCTGACCTCAAGTCATCTGC | (SEQ ID NO:94) |
| 12 | 3 | Forward: CGGGCAGATGACTTGAGGT | (SEQ ID NO:95) |
|   |   | Reverse: CCTTGGTGGTTAGCATGGTT | (SEQ ID NO:96) |
| 13 | 3 | Forward: GCTAACCATGCTAACCACCAA | (SEQ ID NO:97) |
|   |   | Reverse: CCCATGGGAACTCACAATCT | (SEQ ID NO:98) |
| 14 | 3 | Forward: TAGCACCCTGAGCCTGTACC | (SEQ ID NO:99) |
|   |   | Reverse: CCACTGGAAGCTGTGGCTAT | (SEQ ID NO:72) |

TABLE 2-continued

PCR primers for genomic amplification of nup62

| PCR product Number | Exon Number | Primer Sequence from 5' to 3' (SEQ ID NO:) | |
|---|---|---|---|
| 15 | 3 | Forward: ACTGTCGTTCCCCGTGTGT | (SEQ ID NO:12) |
| | | Reverse: TTCAGCAAAGTATAAAGACAAATACAA | (SEQ ID NO:13) |
| 16 | 3 | Forward: TGTGTGGAAGGCAGAAGCTA | (SEQ ID NO:14) |
| | | Reverse: GCTTTCTCCTCCTAACATTTATCC | (SEQ ID NO:15) |

PCR primers and reaction conditions used to amplify all 3 exons of the nup62 gene (primer sequences were derived from GenBank Accession No. NM_153719). PCR reactions included: denaturation: 95° C., 5 minutes, 25 cycles of: denaturation at 95° C. for 30 seconds, annealing at 57° C. for 30 seconds and elongation 72° C. for 30 seconds, followed by 7 minutes elongation at 72° C.

Experimental Results

Linkage analysis—To refine the boundaries of the candidate region as defined he markers D19S596 and D19S867 in the previous study (8) publicly available sequence databases (USCS Genome Browser, GDB) were searched to identify six additional microsatellite markers and one SNP, which were used to genotype all the family members in the two critical pedigrees (FIGS. 12a-b). Loss of homozygosity in family 1 (individuals II-2 and II-3 in FIG. 12a) defined the centromeric border of the candidate region distally to the SNP rs8101959 in the AP2A1 gene (FIG. 13). A recombination event was observed in family 2 (FIG. 12b), individual II-4, defining the telomeric border of the candidate region and placing the disease-causing gene proximal to the polymorphic marker D19S867 (FIG. 12b). Informative recombinations and the presence of a common haplotype indicated a minimal candidate interval of 230 kb between markers rs8101959 and D19S867 (FIGS. 12a-b). As is shown in FIG. 13, the minimal candidate region contains 13 candidate genes.

Mutation analysis—Sequencing of the nup62 gene [GenBank Accession No. NM_012346 (SEQ ID NO:68) for mRNA, NC_000019.8 from nucleic acid 55124598-55101894 for genomic sequence] in the minimal region of linkage revealed a missense mutation (1429A→C as set forth by SEQ ID NO:68), located 1,172 bps downstream from the ATG translation initiation codon found in exon 3 (according to: Recommendations for the description of DNA sequence variants; Ensembl genome browser) (FIGS. 14a-b). The mutation causes a change from glutamine to proline at amino acid residue 391 (Q391P) as set forth by SEQ ID NO:69 (GenBank Accession No. NP_036478 for the nup62 gene product, p62 polypeptide). In each pedigree analyzed, the nup62 mutation segregated with the disease: affected individuals (patients) displayed homozygous mutations, whereas parents who were clinically normal displayed heterozygosity for a normal and a disease allele (carrier of disease-allele), consistent with recessive inheritance (FIGS. 15a-b). The mutation was not observed in 620 chromosomes from unrelated control individuals of Jewish and Arab origin as determined by NciI restriction enzyme assay using the primers set forth by SEQ ID NOs:64 and 65. However, this mutation has a frequency of 0.04 (12 heterozygotes in 280 chromosomes) in ethnically matched (Bedouin) controls living in the same village as the original family and the neighboring villages. All the heterozygous individuals also carried alleles corresponding to the alleles present in the disease-related haplotype in the several polymorphic markers adjacent to the mutation, indicating the same origin of the mutated allele.

All the other genes in the candidate region, including AP2A1, MED25, PTOV, PNKP, AKT1S1, TBC1D17, IL4I1, ATF5, SIGLEC11, VRK3, FLJ22688 (GenBank Accession No. NM_025129) and the first two exons of ZNF473, were sequenced, and no pathogenic sequence changes were found.

Altogether, these results demonstrate the identification of the gene causing IBSN. This gene encodes the nuclear protein p62 protein and is located on chromosome 19q between markers rs8101959 and D19S867. As described hereinabove, a missense mutation Q391P in the p62 protein (nup62 gene) is the causative mutation resulting in IBSN in several families of the analyzed Bedouin population.

Example 4

Prenatal Diagnosis of Fetus for the Diagnosis of IBSN

The teachings of the present invention were employed in order to perform prenatal diagnosing for IBSN in suspected families. The presence or absence of the Q391P mutation (encoded by a 1429A→C substitution as set forth by SEQ ID NO:68) was tested using the NciI restriction enzyme assay described in Example 3, hereinabove.

Materials and Experimental Methods—as in Example 3, hereinabove

Experimental Results

Identification of the new families and prenatal diagnosis—Two additional families bearing the same family name, including two affected and 11 unaffected individuals, were identified while this study was ongoing. The affected individuals were homozygous for the nup62 mutation (Q391P as set forth by SEQ ID NO:69; 1429A→C as set forth by SEQ ID NO:68).

Five prenatal diagnoses were performed in three at-risk families. Two affected fetuses were found to be homozygous for the nup62 mutation in two subsequent pregnancies in the same family. The first pregnancy was terminated, but the family decided to continue the second pregnancy, and the child exhibited clinical signs of the disease at the age of 8 months. In the other families, the fetuses were found to be unaffected, and three healthy children were born, all of whom are currently developing normally.

Thus, the present invention provides, for the first time a genetic tool for prenatal diagnosis of IBSN. It should be noted, that prenatal diagnosis in families unrelated to the abovedescribed Bedouin families should be performed by mutational screening (e.g., by sequence analysis) of the gemonic sequence encoding nup62.

Example 5

Mutated Q391P nup62 Exhibits Normal Expression Level and Cellular Localization

Materials and Experimental Methods

Western blot—The lymphoblastoid cell proteins were prepared. Cells were washed twice with PBS and lysed at 4° C. with lysis buffer. After incubation, cell lysates were centrifuged and the supernatants collected. The pellet fraction was vortexed at 4° C. and the proteins were collected. Proteins from the two fractions were determined using the BCA Protein Assay Reagent Kit (PIERCE). Whole-cell proteins were subjected to 12% SDS-PAGE and transferred to nitrocellulose membranes. The membranes were blocked for 30 minutes at room temperature with 5% skim milk in TBS-Tween buffer and subsequently incubated with primary monoclonal mouse Mab414 anti p62 antibodies (kindly provided by Dr. Amnon Harel, Technion, Israel, and Douglass J. Forbes, UCSD, USA, Abcam) at a dilution of 1:2500. After washing with TBS-Tween, further incubation for 1 hour with peroxidase-conjugated goat anti mouse IgG (Jackson ImmunoResearch Laboratories, West Grove, Pa.) at a dilution of 1:5000 was carried out. Immunoreactive proteins were visualized by an ECL (enhanced chemiluminescence super signal) Detection Kit (PIERCE). Rabbit polyclonal antibodies to Emerin (Santa Cruz Biotechnology) were used to demonstrate equal loading levels.

Immunofluorescence of lymphoblastoids—Human lymphoblastoid (LB) cells were cytospun onto slides. The cells were fixed for 5 minutes with ice-cold methanol and ice-cold acetone for a further 5 minutes, washed with TBS and blocked for 30 minutes using 5% skim milk in TBS containing 0.1% Tween 20 (TBS-T). Incubations with primary mouse monoclonal p62 antibodies (BD Transduction Laboratories) in a 1:100 dilution and secondary Cy3-conjugated goat anti-mouse antibodies in a 1:500 dilution were performed in blocking solution for 1 hour each. Between and after the incubation with the antibodies cells were washed 3 times with TBS-Tween. The slides were mounted using DAPI containing Fluoromount-G (SouthernBiotech) and the cells were photographed using the Improvision (Improvision, UK) optic grid confocal fluorescent microscope (Olympus).

Generation of YFP-p62 fused constructs—RNA was extracted from the patient's and control's lymphoblastoid cell lines using RNeasy® Mini Kit (Qiagen) according to the manufacturer's protocol. cDNA was synthesized by RT-PCR using the EZ-First strand cDNA synthesis Kit manufactured by Biological industries according to the manufacturer's protocol. To prepare normal and mutated YFP-p62 fusion constructs the control and mutated nup62 cDNAs were amplified using the following PCR primers: Forward (incorporating the XhoI restriction site in the YFP gene): 5'-GCCTCGAGC-CATGAGCGGGTTTAATTTTGGAG-3' (SEQ ID NO:66); Reverse (incorporating the XbaI restriction site downstream to the YFP gene's stop codon): 5'-GCTCTAGAGTCGCT-CAGTCAAAGGTGATCCGG-3' (SEQ ID NO:67). The amplified cDNAs of both normal and mutant nup62 were ligated using T4 ligase (Promega) to the YFP-plasmid digested with the XhoI and XbaI restriction enzymes.

Transfection and Immunofluorescence analysis—Human osteosarcoma cell line U2OS was cultured in Dulbecco's modified Eagle's medium (DMEM) (Gibco, BRL) supplemented with 10% fetal calf serum (FCS), 2 mM glutamine, 100 mg/ml streptomycin and 100 units/ml penicillin (Gibco, BRL, Paisley, Scotland), at 37° C. in a humidified incubator with 5% $CO_2$. U2OS cells were plated 24 hours before transfection at $2 \times 10^5$ cells per well in a six-well plate on coverslips and transiently transfected with YFP-p62 or YFP-mutant p62. Transfections were performed using the Jet PEI™ transfection reagent (poly plus). DNA amounts were kept constant by adding vector DNA (pCDNA3) when required. Twenty-four hours after transfection the cells were fixed for 30 minutes with ice-cold 4% PFA (paraformaldehyde) and washed 3 times with TBS containing 0.1% Tween 20. The immunofluorescence procedure was performed using mouse monoclonal anti-p62 antibody as described above.

Confocal microscopy—Cells were analyzed using a 410 Zeiss confocal laser scan microscope (CLSM) (Zeiss, Oberkochen, Germany). The Zeiss LSM 410 is equipped with a U.V. laser (Coherent Inc. Lazer Group, Santa Clara, Calif., USA) and with a 25 mW krypton-argon laser and a 10 mW helium-neon laser (488, 543 and 633 maximum lines). A 63× numeric aperture/1.2 C Apochromat water-immersion lens (Axiovert 135M, Zeiss) was used for all imaging. Series of 10-15 optical sections 2 microns apart were obtained.

Experimental Results

No reduction in the expression level of nup62 is observed in the mutant Q391P protein—Western blot analysis was used to examine the expression level of nup62 in lymphoblastoid cell line from each of the patient and control individuals. As is shown in FIGS. 17a-b, no reduction in the level of the mutated protein was observed in the patient's cell line as compared to the normal individual's.

No visible difference was observed in the localization of nup62 in the nuclear membrane—The effect of the mutation on the localization of the p62 protein in the nuclear membrane was examined by immunofluorescent staining of normal and patient lymphoblastoids. As shown in FIGS. 18a-f, no differences were observed between the patient and control lymphoblastoid cells. Further analysis using transfected U2OS cells overexpressing normal and mutant YFP-p62 fusion protein were employed in order to follow the pattern of transfection. As is shown in FIGS. 19a-f, observation of the fluorescent signal revealed diverse patterns of expression, including (i) staining of the nuclear envelope with a fine punctuate pattern consistent with pore binding, (ii) phase-dense cytoplasmic aggregates, and (iii) diffuse cytoplasmic staining. These three staining patterns were in agreement with the previous rat p62 expression studies (Starr C M, et al., 1990, Primary sequence and heterologous expression of nuclear pore glycoprotein p62. J. Cell Biol. 110: 1861-1871). No differences between the normal and the mutated fusion protein signal were observed (FIGS. 19a-f).

Altogether, no detectable difference in the expression level and/or nuclear localization was observed in the mutant 391P polypeptide.

Example 6

The Q391P Mutation in the nup62 Protein is Predicted to Hamper the Functional Activity of the nup62 Protein Bioinformatics Methods—Gene and protein descriptions were performed using UCSC and Ensembl genome browsers [assembly of May 2004] and bioinformatics servers. The best nine vertebrate (from fish to human) sequence homologues to human p62 protein were collected using BLink ("BLAST Link"). Comparative sequence analysis (multiple sequence analysis; MSA) was carried out by ClustaW with a Java viewer, as described by Higgins et al. (Higgins D, Thompson J, Gibson T, et al. CLUSTAL W: improving the sensitivity of progressive multiple sequence alignment through sequence weighting, position-specific gap penalties and weight matrix choice. Nucleic Acids Res 1994; 22:4673-4680) and Clamp et al. (Clamp M, Cuff J, Searle S M, Barton G J. The Jalview Java Alignment Editor. Bioinformatics 2004; 20:426-427) ConSeq server was used to validate sequence conservation and predict functionality (Berezin C, Glaser F, Rosenberg J, et al. ConSeq: The identification of functionally and structurally important residues in protein sequences. Bioinformatics 2004; 20:1322-1324). The SIFT server sorts intolerant from tolerant amino acid substitutions and predicts phenotypic variations, as described by Ng and Henikoff (Ng P C, Henikoff S. Accounting for human polymorphisms predicted to affect protein function. Genome Research 2002; 12:436-446).

Bioinformatics Results

Gene and protein description using bioinformatics tools—Nup62 gene (RefSec constructed genomic contigs GenBank Accession Nos. NT_011109.15 and NT_086906.1) covers 22,705 bp of genomic DNA. The nup62 gene consists of a single promoter with a CpG island and three transcribed exons. The second exon is prone to alternative splicing (Wiemann S, Kolb-Kokocinski A, Poustka A. Alternative pre-mRNA processing regulates cell-type specific expression of the IL411 and NUP62 genes. BMC Biol 2005; 3:16). The protein encoded by nup62, nuclear pore glycoprotein p62, is ubiquitously expressed in various tissues [Wiemann, 2005 (Supra) and GeneCards database]. All transcript variants encode a protein of 522 residues [NCBI: NP_036478; SEQ ID NO:69; UniProt/Swiss-Prot: P37198; 53269 Da (GeneCards)]. Nup62 is embedded in intron 8-9 of the IL411 gene (Ensembl OTTHUMG00000070945). It was recently shown by Wiemann, 2005 (Supra) that the IL4I1 gene is specifically transcribed from the apparent promoter of the upstream nup62 gene in testis (Sertoli cells) and in the brain (e.g., Purkinje cells); the first two exons of nup62 are also contained in this novel IL4I1 variant. However, since the first two exons are non-coding, and the protein is encoded exclusively by the terminal 3rd exon, it is not expect the mutation found in the present study (Q391P) affects the function of the protein encoded by this transcript. A single conserved domain Nsp1_C (Nsp1-like, C-terminal) has been identified in the Pfam and InterPro databases (PF05064; residues 307-429; IPR007758; residues 310-432, respectively).

Multiple alignment (MSA), ConSeq and SIFT results—Multiple alignment (MSA) was performed using nine protein sequence homologues of p62 (nup62), including vertebrates from fish to human. MSA of amino acids 348 to 408 is shown in FIG. 16. An especially conserved region was found to be present at the C-terminal region of the protein, harboring the Nsp1-like C-terminal domain, which includes the Q391 residue of the human protein. Examination of amino acid conservation in the Pfam database also revealed distant relatives of the family, including the yeast protein (C. cerevisiae; Baker's yeast) that was shown to be highly conserved for glutamine at this position. However, C. elegans and S. pombe showed variations of the glutamine residue to R (arginine) and D (aspartic acid), respectively. Amino acid residues R, D and Q are known to be hydrophilic and polar amino acids, with relatively similar characteristics. To conclude, the region harboring Q391 in the human protein is most conserved in evolution, from yeast to mammals, and therefore a variation at this point is predicted to lead to a severe change in protein function.

ConSeq server was applied to further support this conservation notion, using the same sequences as in MSA above. Nsp1-like C-terminal domain is shown (FIG. 17). Again, the Q391 position in the human protein was found to be the most conserved. In addition, this region was predicted to be an exposed and a functional region of the protein, supporting the hypothesized importance of it.

SIFT is a sequence homology-based tool that sorts intolerant from tolerant amino acid substitutions and predicts whether an amino acid substitution in a protein will result in a phenotypic effect (Ng P C, Henikoff S. Accounting for human polymorphisms predicted to affect protein function. Genome Research 2002, 12: 436-446). Predicted results for residue Q391 in the human protein showed that the only tolerated changes in this amino acid may be to E (glutamic acid) or R (arginine), both of which are hydrophilic-polar amino acids, while a change to any other amino acid is predicted to be not tolerated, i.e., to result in a protein with an abnormal, deficient functional activity.

Altogether, these results demonstrate that the Q391P mutation is predicted to affect the functional activity of p62.

Analysis and Discussion

Evidence that a nup62 mutation causes IBSN—There is much evidence that supports the role of the Q391P mutation in nup62 as the cause of IBSN. First of all, sequencing of all the other genes in the candidate region revealed no pathogenic mutations. In addition, the Q391P mutation was not found in 620 control chromosomes from ethnically unrelated individuals, and it was found only in the heterozygous state in 280 control chromosomes from members of the Bedouin population originating in the same geographic area as the original families. The presence of such heterozygous individuals was expected because of the high frequency of carriers within this Bedouin population. Furthermore, the Q391P mutation produces a substitution that results in a change from a polar, hydrophilic residue (acquired by the amide group) to a non-polar, neutral residue. Glutamine plays an important structural role inside proteins by providing hydrogen bonding. Proline markedly influences protein architecture because its ring structure makes it more conformationally restricted, with a strong influence on protein folding, than all the other amino acids (Berg J M, Tymoczko J L, Stryer L. Biochemistry (5th edition), W.H. Freeman, New York, 2002). In addition, comparisons of p62 protein sequences from diverse species indicate that glutamine at position 391 is highly conserved. The region of Nsp1-like C-terminal (amino acids 307-429) is almost completely identical in human, mouse and rat, and mostly similar in all vertebrates (FIGS. 16 and 17). In addition, it is homologous to the essential yeast NSP1 carboxy-terminal domain, and therefore is presumably highly important in determining p62 function. Finally, four patients in two new families identified during this study were found to be homozygous for the same nup62 mutation.

The disease-causing mechanism does not involve abnormal p62 targeting or anchoring to the nuclear pore complex—The protein encoded by nup62 belongs to the class of nucleoporins and is an essential part of the nuclear pore complex (NPC) (Finlay D R, et al. A complex of nuclear pore proteins required for pore function. J Cell Biol 1991, 114:169-183; Hetzer M W, et al., Pushing the envelope: structure, function, and dynamics of the nuclear periphery. Annu Rev Cell Dev Biol 2005, 21:347-380). The nuclear pore complex is a massive structure that extends across the nuclear envelope, forming a gateway that regulates the flow of mRNA and proteins between the nucleus and the cytoplasm (Dargemont C, et al., Direct interaction of nucleoporin p62 with mRNA during its export from the nucleus. J Cell Sci 1995, 108:257-263; Allen T D, et al., The nuclear pore complex: mediator of translocation between nucleus and cytoplasm. J Cell Sci 2000, 113: 1651-1659; Cronshaw J M, et al., Proteomic analysis of the mammalian nuclear pore complex. J Cell Biol 2002, 158:915-927). The p62 protein encoded by nup62 is a member of the phenylalanine-glycine (FG) repeats-containing nucleoporins (Ryan K J, Wente S R. The nuclear pore complex: a protein machine bridging the nucleus and cytoplasm. Curr Opin Cell Biol 2000, 12:361-371). This protein associates with the importin alpha/beta complex, which is involved in the import of proteins containing nuclear localization signals (Percipalle P, et al. Molecular interactions between the importin alpha/beta heterodimer and proteins involved in vertebrate nuclear protein import. J Mol Biol 1997, 266:722-732). The p62 protein appears to exist as a tight complex with at least two other proteins, p58 and p54 [Finlay D R, 1991 (Supra); Kita K, et al., Purification and characterization of a nuclear pore glycoprotein complex containing p62. J Biochem 1993, 113: 377-382). Rat p62 protein concentrates at the spindle poles during mitosis and in telophase is found in the region of condensed chromatin (Starr C M, et al., Primary sequence and heterologous expression of nuclear pore glycoprotein p62. J Cell Biol 1990, 110:1861-1871). Its N-terminus is believed to be involved in nucleocytoplasmic transport, while the C-terminal end, which reveals a hydrophobic heptad repeat organization similar to that found in lamins and other intermediate filament proteins, contains a coiled-coil structure aiding in protein-protein interactions, and may function in anchorage of the protein in the pore complex (Carmo-Fonseca M, et al., Human nucleoporin p62 and the essential yeast nuclear pore protein NSP1 show sequence homology and a similar domain organization. Eur J Cell Biol 1991, 55:17-30). Moreover, it was shown that the yeast Nsp1p coil 2 region, which is homologous to the region containing the mutation in our patients, has a role in both nuclear import and mRNA export, most likely because this region organizes two different heterodimeric subcomplexes, Nsp1p-Nup57p-Nup49-Nic96p and Nsp1p-Nup82p-Nup159p, respectively (Bailer S M, et al., The Nsp1p carboxy-terminal domain is organized into functionally distinct coiled-coil regions required for assembly of nucleoporin subcomplexes and nucleocytoplasmic transport. Mol Cell Biol 2001, 21:7944-7955). Normal immunostaining of the overexpressed YFP-p62 mutated protein in the U2OS cell line points to the fact that p62 in the affected individuals of the present invention is normally targeted and anchored to the nuclear pore complex.

Nucleoporins and Mendelian human diseases—Only one gene encoding a protein localizing to a nuclear pore complex that causes human Mendelian disease has been described before. Mutations in the WD repeat nucleoporin called ALADIN cause Allgrove (triple A) syndrome (Tullio-Pelet A, et al. Mutant WD-repeat protein in triple-A syndrome. Nat Genet 2000, 26:332-335). Triple A syndrome is characterized by adrenal insufficiency, abnormal development of the autonomic nervous system causing achalasia of the esophagus and alacrima, and late-onset progressive neurological symptoms (including cerebellar ataxia, peripheral neuropathy and mild dementia). Characterization of mutant ALADIN proteins from triple A syndrome patients revealed defective NPC targeting (Cronshaw J M, Matunis M J. The nuclear pore complex protein ALADIN is mislocalized in triple A syndrome. Proc Natl Acad Sci USA 2003, 100:5823-5827). Mutant protein failed to localize to NPCs and was found predominantly in the cytoplasm. The mutation in nup62 described in this study is the second example of a nuclear pore complex protein causing Mendelian disease in humans. Both diseases share central nervous system involvement. The Q391P mutation does not affect localization of the mutant protein to NPCs, suggesting another, as yet unknown, biological cell-type specific mechanism or mechanisms that cause basal ganglia disease in the affected IBSN patients of the present study. Numerous possible models can be hypothesized, including very delicate changes in the NPC structure or the abnormal transport pathway of a specific, as yet unknown protein in neuronal cells in basal ganglia. Alternatively, the mutation might affect chromatin organization in the specific cell type in the CNS. The identification of proteins that can no longer interrelate properly with the mutant protein would be a future goal.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Additional References are Cited in Text

1. F. Molinari et al., *Science* 298, 1779 (2002).
2. J. J. Higgins, J. Pucilowska, R. Q. Lombardi, J. P. Rooney, *Neurology* 63, 1927 (2004).
3. L. Basel-Vanagaite et al., *J. Med. Genet.* 40, 729 (2003).
4. B. A. Davletov, T. C. Suedhof, *J. Biol. Chem.* 268, 26386 (1993).
5. De Meirleir L, Seneca S, Lissens W, et al. Bilateral striatal necrosis with a novel point mutation in the mitochondrial ATPase 6 gene. Pediatr Neurol 1995, 13:242-246.
6. Thyagarajan D, Shanske S, Vazquez-Memije M, et al. A novel mitochondrial ATPase 6 point mutation in familial bilateral striatal necrosis. Ann Neurol 1995, 38:468-472.
7. Straussberg R, Shorer Z, Weitz R, et al. Familial infantile bilateral striatal necrosis: clinical features and response to biotin treatment. Neurology 2002, 59:983-989.
8. Basel-Vanagaite L, Straussberg R, Ovadia H, et al. Infantile bilateral striatal necrosis maps to chromosome 19q. Neurology 2004, 62:87-90.

What is claimed is:

1. A method of diagnosing non-syndromic mental retardation (NSMR) associated with psychomotor developmental delay in an individual, the method comprising analyzing a sequence of a coiled-coil and C2 domain containing 1A (CC2D1A) as set forth by SEQ ID NO:1 or SEQ ID NO:110 of the individual for a presence of a disease causing mutation in said sequence, wherein said disease-causing mutation is the deletion of the genomic nucleic acid sequence as set forth by SEQ ID NO:109, wherein said presence of said disease-causing mutation in said sequence is indicative of the non-syndromic mental retardation associated with psychomotor developmental delay, thereby diagnosing the non-syndromic mental retardation associated with psychomotor developmental delay in the individual.

2. The method of claim 1, wherein said analyzing said sequence of said CC2D1A as set forth by SEQ ID NO:1 or SEQ ID NO:110 is performed using an isolated nucleic acid sequence capable of specifically hybridizing to a mutated CC2D1A nucleic acid sequence encoding the mutated CC2D1A sequence of SEQ ID NO:5 and not to a wild-type CC2D1A nucleic acid sequence.

3. The method of claim 2, wherein said isolated nucleic acid sequence is bound to a solid support.

4. The method of claim 2, wherein said isolated nucleic acid sequence is labeled.

5. The method of claim 1, further comprising selecting an individual suspected or at risk of having mental retardation prior to said analyzing said sequence.

* * * * *